US012098227B2

(12) United States Patent
Dorfinger et al.

(10) Patent No.: US 12,098,227 B2
(45) Date of Patent: Sep. 24, 2024

(54) 3D PRINTED COMPOSITES FROM PHASE SEPARATED MATERIALS

(71) Applicant: Align Technology, Inc., San Jose, CA (US)

(72) Inventors: Peter Dorfinger, Woodside, CA (US); Michael Christopher Cole, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 195 days.

(21) Appl. No.: 17/462,884

(22) Filed: Aug. 31, 2021

(65) Prior Publication Data

US 2022/0162362 A1 May 26, 2022

Related U.S. Application Data

(60) Provisional application No. 63/072,804, filed on Aug. 31, 2020.

(51) Int. Cl.
| | |
|---|---|
| *C08F 2/46* | (2006.01) |
| *A61C 7/08* | (2006.01) |
| *B33Y 10/00* | (2015.01) |
| *B33Y 70/00* | (2020.01) |
| *B33Y 80/00* | (2015.01) |
| *C08F 2/50* | (2006.01) |
| *C08F 220/30* | (2006.01) |
| *C08G 61/04* | (2006.01) |
| *C08L 33/14* | (2006.01) |

(52) U.S. Cl.
CPC ............ *C08F 220/303* (2020.02); *A61C 7/08* (2013.01); *B33Y 10/00* (2014.12); *B33Y 70/00* (2014.12); *B33Y 80/00* (2014.12); *C08L 33/14* (2013.01)

(58) Field of Classification Search
CPC ........ G16H 20/40; G16H 20/30; G16H 50/50; B33Y 10/00; B33Y 80/00; B33Y 70/00; B29C 64/129; B29C 2071/0027; A61C 7/08; A61C 7/002; C08F 220/303; C08F 220/36; C08F 2/48; C08F 222/1065; C08L 33/14
USPC ............... 522/111, 1, 71, 189, 184, 6; 520/1
See application file for complete search history.

(56) References Cited

U.S. PATENT DOCUMENTS

| | | |
|---|---|---|
| 5,820,368 A | 10/1998 | Wolk |
| 5,975,893 A | 11/1999 | Chishti et al. |
| 6,183,248 B1 | 2/2001 | Chishti et al. |
| 6,309,215 B1 | 10/2001 | Phan et al. |
| 6,386,864 B1 | 5/2002 | Kuo |
| 6,450,807 B1 | 9/2002 | Chishti et al. |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,749,414 B1 | 6/2004 | Hanson et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |

(Continued)

FOREIGN PATENT DOCUMENTS

| | | |
|---|---|---|
| CN | 105943406 A | 9/2016 |
| WO | WO-9962460 A1 | 12/1999 |

(Continued)

OTHER PUBLICATIONS

Kwei T.K., "Introduction to Physical Polymer Science," Second Edition, by L. H. Sperling, Wiley, New York, 1992.

(Continued)

*Primary Examiner* — Jessica Whiteley

(74) *Attorney, Agent, or Firm* — Seed IP Law Group LLP

(57) ABSTRACT

The present disclosure provides methods, systems, devices, and kits for creating composite materials from a single resin, the composite materials having multiple continuous phases. The disclosure includes a process to three-dimensionally print objects (e.g., orthodontic appliances) with composite properties. In some aspects, the composite properties are formed from a single formulation with components that, when processed, have hard and soft continuous phases. In some aspects, the composite properties are formed by separately processing the hard phase components and the soft phase components. In some aspects, the composite materials and devices are three-dimensionally printed using the processed material.

25 Claims, 8 Drawing Sheets

(56) References Cited

U.S. PATENT DOCUMENTS

| | | |
|---|---|---|
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,892,474 B2 | 2/2011 | Shkolnik et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0061974 A1 | 3/2014 | Tyler |
| 2014/0067334 A1 | 3/2014 | Kuo |
| 2014/0265034 A1 | 9/2014 | Dudley |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0265376 A1 | 9/2015 | Kopelman |
| 2015/0366638 A1 | 12/2015 | Kopelman et al. |
| 2016/0193014 A1 | 7/2016 | Morton et al. |
| 2016/0242870 A1 | 8/2016 | Matov et al. |
| 2016/0242871 A1 | 8/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007366 A1 | 1/2017 | Kopelman et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2018/0153648 A1 | 6/2018 | Shanjani et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0029775 A1 | 1/2019 | Morton et al. |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0337117 A1 | 11/2019 | Ganapathiappan et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |

FOREIGN PATENT DOCUMENTS

| | | |
|---|---|---|
| WO | WO-2015075094 A1 | 5/2015 |
| WO | WO-2016078838 A1 | 5/2016 |
| WO | WO-2018032022 A1 | 2/2018 |

(56) References Cited

FOREIGN PATENT DOCUMENTS

| WO | WO-2019006409 A1 | * | 1/2019 | ............... A61C 7/08 |
| WO | WO-2019213585 A1 | * | 11/2019 | ........... A61C 19/003 |
| WO | WO-2020013765 A1 | | 1/2020 | |

OTHER PUBLICATIONS

Odian, G., "Principles of Polymerization," 4th Edition, Wiley Online Books, 2004.
Tumbleston J.R., et al., "Continuous Liquid Interface Production of 3D Objects," Science (Mar. 2015), vol. 347.6228: pp. 1349-1352.

* cited by examiner

150 ⟶

```
┌─────────────────────────────────────┐
│ Apply a first orthodontic appliance to a │
│ patient's teeth to reposition the teeth │──160
│ from a first tooth arrangement to a │
│ second tooth arrangement │
└─────────────────────────────────────┘
                    │
                    ▼
┌─────────────────────────────────────┐
│ Apply a second orthodontic appliance to the │
│ patient's teeth to reposition the teeth │──170
│ from the second tooth arrangement to a │
│ third tooth arrangement │
└─────────────────────────────────────┘
```

FIG. 1C

Vertical Dimension

Lateral Dimensions

3D PRINTED COMPOSITES FROM PHASE SEPARATED MATERIALS

CROSS-REFERENCE

This application claims the benefit of U.S. Provisional Application No. 63/072,804, filed Aug. 31, 2020, which application is incorporated herein by reference in its entirety for all purposes.

BACKGROUND OF THE INVENTION

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner and/or a patient. The appliance is configured to exert force on one or more teeth in order to effect desired tooth movements. The application of force can be periodically adjusted (e.g., by altering the appliance or using different types of appliances) in order to incrementally reposition the teeth to a desired arrangement. Polymeric materials can be used to fabricate appliances to be used to reposition a patient's teeth.

SUMMARY OF THE INVENTION

Polymeric materials that have dual characteristics of stiffness and elasticity are desirable, as are 3D printable resins that can form such polymeric materials. The present disclosure provides methods, systems, and devices for the generation of composite materials from a single resin using phase separation.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Provided herein are methods, systems, devices, and kits for creating composite materials from a single resin. In some embodiments, the resin comprises a first continuous phase comprising a component having a first reactivity; and a second continuous phase comprising a component having a second reactivity, the first reactivity is greater than the second reactivity, and the resin is capable of being a 3D printable resin. Also provided herein are methods for creating composite materials by using a resin comprises a first continuous phase comprising a component having a first reactivity; and a second continuous phase comprising a component having a second reactivity, the first reactivity is greater than the second reactivity, and the resin is capable of being a 3D printable resin and initiating a polymerization reaction by curing the resin. Also provided herein are orthodontic appliance using composite materials or compositions as disclosed herein.

In various aspects, provided herein is a curable resin, comprising: a first continuous phase comprising a first polymerizable component having a first polymerization rate; and a second continuous phase comprising a second polymerizable component having a second polymerization rate, wherein the first polymerization rate and the second polymerization rate are determined at conditions sufficient for 3D printing.

In various aspects, provided herein is a curable resin, comprising: a first continuous phase comprising a first polymerizable component and a second polymerizable component, wherein the first polymerizable component is present at a higher concentration than the second polymerizable component; and a second continuous phase comprising the first polymerizable component and the second polymerizable component, wherein the first polymerizable component is present at a lower concentration than the second polymerizable component.

In various aspects, provided herein is a curable resin, comprising: a first continuous phase comprising a first polymerizable component; a second continuous phase comprising a second polymerizable component; and a third continuous phase comprising a third polymerizable component.

In various aspects, provided herein is a curable resin, comprising: a first continuous phase comprising a free-radically polymerizable component; and a second continuous phase comprising an ionically polymerizable component, wherein the free-radically polymerizable component has a higher polymerization rate than the ionically polymerizable component.

In some embodiments, the first continuous phase, upon curing, comprises a first polymer region having a first hardness from 60 Shore A to 85 Shore D; the second continuous phase, upon curing, comprises a second polymer region having a second hardness from 60 Shore A to 85 Shore D, wherein the first hardness is less than the second hardness as determined after 24 hours in an aqueous environment at 37° C. In some aspects, the first polymerizable components comprises a methacrylate moiety and the second polymerizable component comprises an acrylate moiety. In some aspects, the first polymerization rate has a rate constant of at least $3.5 \times 10^3$ s$^{-1}$ and not more than $5 \times 10^3$ s$^{-1}$, and the second polymerization rate has a rate constant of at least $1.8 \times 10^3$ s$^{-1}$ and not more than $2.5 \times 10^3$ s$^{-1}$. In some aspects, the component having the first polymerization rate is an acrylate and the component having the second polymerization rate is a methacrylate. In some aspects, the acrylate is difunctional and the methacrylate is monofunctional. In some aspects, the acrylate is difunctional, the methacrylate is difunctional, and the methacrylate is sterically larger than the acrylate. In some aspects, the component having the second polymerization rate is a vinyl ester. In some aspects, the component having the first polymerization rate is an acrylate or a methacrylate. In some aspects, the component having the first polymerization rate is free radically polymerizable. In some aspects, the component having the first polymerization rate is a free radically polymerizable monomer. In some aspects, the component having the first polymerization rate comprises an acrylate, a methacrylate monomer, or a combination thereof. In some aspects, the component having the second polymerization rate is ionically polymerizable. In some aspects, the component having the second polymerization rate is an ionically polymerizable monomer. In some aspects, the component having the second polymerization rate comprises an epoxide. In some aspects, the epoxide is a cationically-curable epoxide. In some aspects, a resin herein can further comprise a third phase, a fourth phase, or more than four phases. In some aspects, the third phase comprises a filler. In some aspects, the third phase comprises a polymer. In some aspects, the polymer comprises a thermoplastic. In some aspects, the polymer is selected from the group consisting of a polyolefin, a polyester, a polyacrylate, polymethacrylates, polystyrenes, polypropylenes, polyethylenes, polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers. In some aspects, the component having the first polymerization rate comprises a polymer and the component having the polymerization rate comprises a polymerizable monomer; or the component having the first polymerization rate comprises a polymerizable monomer and the component having the second polymerization rate comprises a polymer. In some aspects, the polymer is a thermoplastic. In some aspects, the polymer is miscible with the polymerizable monomer. In some aspects, the polymer is partially or fully immiscible with the polymerizable monomer. In some aspects, upon polymerization of the polymerizable monomer, the polymer is partially or fully insoluble in the resin. In some aspects, the polymer is partially or fully insoluble in the resin. In some aspects, the polymer comprises one or more reactive functional groups. In some aspects, a resin herein can further comprise a filler. In some aspects, a resin herein can further comprise a discontinuous phase comprising the filler. In some aspects, a resin herein can further comprise a continuous phase comprising the filler. In some aspects, the filler is functionalized, comprises a fiber, or a combination thereof. In some aspects, a resin herein can further comprise 3, 4, 5, 6, or more than 6 phases. In some aspects, a resin herein can further comprise a plurality of hard phases. In some aspects, a resin herein can further comprise a plurality of soft phases.

In various aspects, provided herein is a method of producing a composite polymer composition, the method comprising: providing a resin described herein; and initiating a polymerization reaction by curing the resin.

In various aspects, provided herein is a method comprising: curing a resin comprising a first continuous phase and a second continuous phase to produce a composite material comprising a soft region having a first hardness and a hard region having a second hardness, wherein the first hardness is less than the second hardness; fabricating an orthodontic appliance using the composite material; and analyzing the orthodontic appliance to identify the soft region and the hard region of the composite material. In some instances, the analyzing comprises using a microscopy technique.

In various aspects, provided herein is a method of generating a composite material, comprising: subjecting a curable resin comprising a first polymerizable component and a second polymerizable component to conditions sufficient to initiate polymerization; polymerizing the first polymerizable component faster than the second polymerizable component to generate the composite material comprising a soft polymer region having a first hardness and comprising, in a polymerized form, the first polymerizable component, and a hard polymer region having a second hardness and comprising, in a polymerized form, the second polymerizable component.

In various aspects, provided herein is a method of generating a composite material, comprising: subjecting a first polymerizable component of a resin to a first set of conditions sufficient to initiate polymerization of the first polymerizable component; and subjecting a second polymerizable component of the resin to a second set of conditions sufficient to initiate polymerization of the second polymerizable component, wherein the first and second sets of conditions are different, and wherein the first set of conditions comprises one or more of a first light wavelength and a first temperature, and the second set of conditions comprises one or more of a second light wavelength and a second temperature. In some aspects, curing the resin comprises photocuring the resin, thermal curing the resin, or a combination thereof. In some aspects, the polymerization conditions comprise one or more steps of photocuring, one or more steps of thermal curing, or a combination thereof. In some aspects, the photocuring comprises two or more photocuring steps. In some aspects, the thermal curing comprises two or more thermal curing steps. In some aspects, such method can further comprise fabricating an object with the cured polymeric material. In some aspects, the fabricating comprises printing with a 3D printer. In some aspects, the object is an orthodontic appliance. In some aspects, the orthodontic appliance is an aligner, an expander or a spacer. In some aspects, the orthodontic appliance comprises a plurality of tooth receiving cavities configured to reposition teeth from a first configuration toward a second configuration. In some aspects, the orthodontic appliance is one of a plurality of orthodontic appliances configured to reposition the teeth from an initial configuration toward a target configuration. In some aspects, the orthodontic appliance is one of a plurality of orthodontic appliances configured to reposition the teeth from an initial configuration toward a target configuration according to a treatment plan. In some aspects, the orthodontic appliance is an aligner.

In various aspects, further provided herein is a composite material made by any one or more of the resins and/or methods described herein.

In various aspects, further provided herein is a composite material comprising: a first continuous phase comprising a first polymer region, comprising, a first polymerizable component in a polymerized form, and having a first hardness from 60 Shore A to 85 Shore D; and a second continuous phase comprising a second polymer region, comprising a second polymerizable component in a polymerized form, and having a second hardness from 60 Shore A to 85 Shore D, wherein the first polymerizable component polymerized faster than the second polymerizable component, and wherein the first hardness is less than the second hardness as determined after 24 hours in an aqueous environment at 37° C. In some aspects, the first polymerizable component comprises a methacrylate. In some aspects, the second polymerizable component comprises an acrylate. In some aspects, the first polymerizable component comprises a methacrylate and the second polymerizable component comprises an acrylate. In some aspects, the first polymerizable component has a higher molecular weight than the second polymerizable component. In some aspects, the first polymerizable component comprises a methacrylate or an acrylate moiety and the second polymerizable component comprises a vinyl ester. In some aspects, the composite material comprises an interpenetrated network. In some aspects, the second polymer region comprises an epoxide. In some aspects, the epoxide is a cationically cured epoxide. In some aspects, the first continuous phase comprises a vertical dimension less than 100 nm, a lateral dimension less than 100 nm, or a combination thereof. In some aspects, the second continuous phase comprises a vertical dimension less than 100 nm, a lateral dimension less than 100 nm, or a combination thereof (see, e.g., FIG. 5). In some aspects, a composite material described herein can further comprise a gradient between the first continuous phase and the second continuous phase. In some aspects, the composite material is characterized by one or more of: an elongation at break greater than or equal to 5%; a storage modulus greater than or equal to 500 MPa; a tensile modulus greater than or equal to 500 MPa; and a stress remaining greater than or equal to 0.01 MPa. In some aspects, the first continuous phase is characterized by one or more of: an elongation at break greater than or equal to 5%; a storage modulus greater than or equal to 500 MPa; a tensile modulus greater than or equal to 500 MPa; and a stress remaining greater than or equal to 0.01 MPa. In some aspects, the second continuous phase is characterized by one or more of: an elongation at break greater than or equal to 5%; a storage modulus greater than or equal to 500 MPa; a tensile modulus greater than or equal to 500 MPa; and a stress remaining greater than or equal to 0.01 MPa. In some aspects, the composite material, the first continuous phase, the second continuous phase, or a combination thereof is characterized by a stress remaining of 5% to 45% of the initial load, or a stress remaining of 20% to 45% of the initial load. In some aspects, the composite material, the first continuous phase, the second continuous phase, or a combination thereof is characterized by a tensile modulus from 500 MPa to 2000 MPa or a tensile modulus from 800 MPa to 2000 MPa. In some aspects, the composite material is characterized by: an elongation at break greater than or equal to 5%; a storage modulus greater than or equal to 500 MPa; a tensile modulus greater than or equal to 500 MPa; and a stress remaining greater than or equal to 0.01 MPa. In some aspects, the composite material, the first continuous phase, the second continuous phase, or a combination thereof is characterized by an elongation at break greater than 10%, an elongation at break greater than 20%, an elongation at break greater than 30%, an elongation at break of 5% to 250%, an elongation at break of 20% to 250%, or an elongation at break value between 40% and 250%. In some aspects, the composite material, the first continuous phase, the second continuous phase, or a combination thereof is characterized by a storage modulus of 0.1 MPa to 4000 MPa, a storage modulus of 300 MPa to 3000 MPa, or a storage modulus of 750 MPa to 3000 MPa. In some aspects, the composite material, the first continuous phase, the second continuous phase, or a combination thereof is characterized by a stress remaining of 0.01 MPa to 15 MPa, or a stress remaining of 2 MPa to 15 MPa. In some aspects, greater than 70% of visible light passes through the composite material, the first continuous phase, the second continuous phase, or a combination thereof. In some aspects, the composite material, the first continuous phase, the second continuous phase, or a combination thereof is biocompatible, bioinert, or a combination thereof.

Further provided herein is an orthodontic appliance comprising one or more composite material(s) of the present disclosure. In some aspects, the orthodontic appliance is an aligner, an expander, or a spacer. In some aspects, the orthodontic appliance comprises a plurality of tooth receiving cavities configured to reposition teeth from a first configuration toward a second configuration. In some aspects, the orthodontic appliance is one of a plurality of orthodontic appliances configured to reposition the teeth from an initial configuration toward a target configuration. In some aspects, the orthodontic appliance is one of a plurality of orthodontic appliances configured to reposition the teeth from an initial configuration toward a target configuration according to a treatment plan. In some aspects, the orthodontic appliance is an aligner.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 1C illustrates a method of orthodontic treatment using a plurality of appliances, in accordance with embodiments.

DETAILED DESCRIPTION OF THE INVENTION

Figure 1A:
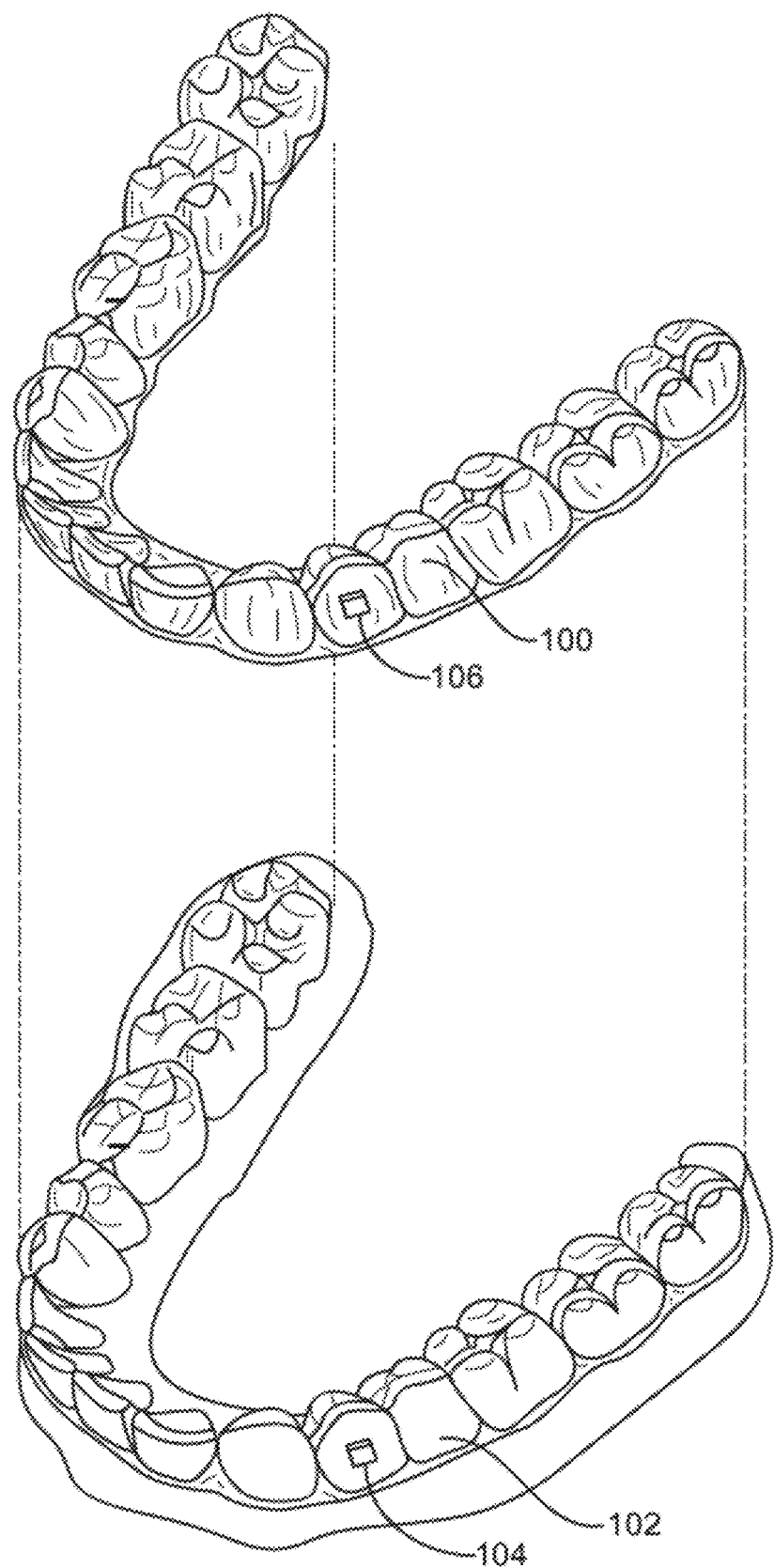
FIG. 1A illustrates a tooth repositioning appliance, in accordance with embodiments.

This disclosure provides compositions, methods, systems, devices, and kits for creating composite materials from a single resin. More specifically, in some aspects, the present disclosure relates to methods, systems, devices, and kits for forming composite materials having multiple continuous phases, wherein the multiple phases are generated from a single formulation resin. In certain aspects, the disclosure includes a process to three-dimensionally print objects (e.g., orthodontic appliances) with composite properties. In some aspects, the composite properties are formed from a single formulation with components that, when processed, have hard and soft continuous phases. In some aspects, the composite properties are formed by separately processing the hard phase components and the soft phase components. In some aspects, the devices are three-dimensionally printed using the processed material.

Composite Components

The present disclosure provides in part composite materials comprising at least two continuous phases formed from a single resin. In embodiments described herein, the composite materials (also referred to herein as polymer composites) comprise a first continuous phase and a second continuous phase. In some embodiments, the first continuous phase comprises a soft polymer region (i.e., soft phase). In certain embodiments, the first continuous phase is a soft polymer region (i.e., soft phase). In some embodiments, the second continuous phase comprises a hard polymer region (i.e., hard phase). In some embodiments, the second continuous phase is a hard polymer region (i.e., hard phase). In some embodiments described herein, the composite materials are formed from a single polymerizable resin. In certain embodiments, photopolymerization is used to polymerize the resin, forming the composite material.

In some aspects, the present disclosure provides a resin that can form multi-composite materials. In some embodiments, the disclosure provides a resin comprising a first continuous phase comprising a component having a first reactivity (i.e., a first component) and a second continuous phase comprising a component having a second reactivity (i.e., a second component). In some embodiments, the first reactivity is greater than the second reactivity. In some embodiments, the resin is capable of being 3D printed (i.e., is a 3D printable resin).

In some embodiments, the soft phase is characterized by the presence of a more reactive component (e.g., comprising the first component when the first component has higher reactivity). In some embodiments, the hard phase is characterized by the presence of a less reactive component (e.g., comprising the second component when the second component has lower reactivity). In some embodiments, the higher reactivity components of the resins described herein are polymerized, thereby forming the soft phase (i.e., soft region) of a composite material. In some embodiments, the lower reactivity components of the resins described herein are polymerized, thereby forming the hard phase (i.e., hard region) of a composite material. As a non-limiting example, a resin comprising a highly reactive component corresponding with a soft phase and a less reactive component corresponding with a hard phase, when polymerized, forms a composite material comprising the hard phase and the soft phase. In some embodiments, it is preferable that the soft phase is processed (e.g., polymerized) before the hard phase. In some embodiments, it is preferable that the soft phase comprises components having higher reactivity than the components of the hard phase (e.g., such that the soft phase is processed, or polymerized, first). In certain embodiments, the soft phase forms prior to the formation of the hard phase. In some embodiments, the soft phase is substantially polymerized (e.g., greater than 90% polymerized, e.g., as determined by FTIR analyzing double bond to single bond conversion) prior to the hard phase being substantially polymerized. In some embodiments, the soft phase is substantially polymerized (e.g., greater than 90% polymerized) prior to 5%, 10%, or 15% of the hard phase being polymerized.

In some embodiments, the first continuous phase, upon curing, comprises a first polymer region. As a non-limiting example, a first continuous phase comprising a first component having a first reactivity (also referred to herein as a first component, a first polymerizable component, and component 1) is polymerized upon curing and forms a first polymer (also referred to herein as polymer 1) in a first polymer region. In some embodiments, the first component is a polymerizable monomer (also referred to herein as a first polymerizable monomer, and monomer 1). In some embodiments, the second continuous phase, upon curing, comprises a second polymer region. As a non-limiting example, a second continuous phase comprising a second component having a second reactivity (also referred to herein as a second component, a second polymerizable component, and component 2) is polymerized upon curing and forms a second polymer (also referred to herein as polymer 2) in a second polymer region. In some embodiments, the second component is a polymerizable monomer (also referred to herein as a second polymerizable monomer, and monomer 2).

A monomer, as used herein, can refer to a reagent which can undergo polymerization under one or more specified conditions. A monomer reagent may comprise at least one monomer molecule, where a monomer molecule is a molecule which can undergo polymerization, thereby contributing constitutional units to the structure of a macromolecule or oligomer or polymer. In an embodiment, a monomer reagent may be represented by an average or dominant chemical structure and comprise a plurality of monomer molecules having that chemical structure but may also contain components with other chemical structures. For example, a monomer reagent may comprise impurities having chemical structures other than the average or dominant structure of the reagent. An oligomer or oligomeric reagent is also a reagent which can undergo polymerization under appropriate conditions. An oligomeric reagent comprises an oligomer molecule, the oligomer molecule comprising a small plurality of units derived from molecules of lower relative molecular mass. In an embodiment, hyperbranched crosslinking reagents suitable for use with the invention may be regarded as oligomeric reagents.

In some embodiments, it is favorable that a curable resin comprises a combination of polymeric components (e.g., oligomer and/or polymers) and monomeric components (e.g., reactive monomers such as reactive diluents). In some embodiments, the first component and/or the second component is a polymer. In some embodiments, the polymer is a reactive polymer (i.e., can undergo further reactions), such as a functionalized or telechelic polymer capable of undergoing further polymerization reactions. In some embodiments, the first component is a polymer and the second component is a polymerizable monomer. In other embodiments, the first component comprises a polymerizable monomer and the second component comprises a polymer. In some embodiments, the first component is a polymerizable monomer and the second component is a polymer.

In some embodiments, the polymer is a thermoplastic, a plastic, and/or a thermoset. In some embodiments, the polymer is a thermoplastic. In some embodiments, the polymer is a plastic as further described herein. In some embodiments, the polymer is miscible with the polymerizable monomer (e.g., wherein the first component is a polymer and the second component is a polymerizable monomer, and the polymer is miscible with the polymerizable monomer). In certain embodiments, the polymer is partially immiscible with the polymerizable monomer. In some embodiments, the polymer is fully immiscible with the polymerizable monomer.

In some embodiments, differences in density and/or immiscibility cause separation of phases or of polymerizable components into sections, wherein one localized point of the resin can comprise a liquid ratio that is different from the liquid ratio of a different localized point within the resin. As a non-limiting example, polymerization induced phase separation (PIPS) can facilitate the separation of continuous phases by changing miscibility of a polymer component in the resin. PIPS can, for example, increase the molecular weight of a first component, decreasing miscibility of the components and resulting in phase separation. In some embodiments, the second component is partially immiscible with the polymer formed from the first component during polymerization (e.g., a first polymer). In some embodiments, the first component is partially immiscible with the polymer formed from the second component during polymerization (e.g., a second polymer). In some embodiments, the second component is fully immiscible with the first polymer. In some embodiments, the first component is fully immiscible with the second polymer.

In some embodiments, a formed polymer is insoluble in the resin. In some embodiments, upon polymerization of the polymerizable monomer in the resin (e.g., polymerization of the first and/or second polymerizable monomer, thereby forming the corresponding polymer), the polymer is partially insoluble in the resin. In some embodiments, upon polymerization of the polymerizable monomer in the resin, the polymer is fully insoluble in the resin. In some embodiments, the polymers formed herein are partially insoluble in the resin. In some embodiments, the polymers formed herein are fully insoluble in the resin. In certain embodiments, the polymer comprises one or more reactive functional groups. Reactive functional groups are further described herein.

In embodiments described herein, the first polymer region (e.g., first continuous phase) has distinct mechanical and/or polymer properties from the second polymer region (e.g., second continuous phase). In some embodiments, the first polymer region has distinct mechanical properties from the second polymer region. In some embodiments, the first polymer region comprises a hardness less than the hardness of the second polymer region. In some embodiments, the first continuous phase is at least 5%, at least 10%, at least 20%, at least 30%, at least 40%, at least 50%, at least 75%, at least 100%, at least 200%, at least 300%, at least 400%, at least 500%, at least 600%, at least 700%, at least 800%, at least 900%, or at least 1000% softer than the second continuous phase. In some embodiments, the first polymer (e.g., formed upon polymerization of the first polymerizable monomer) has distinct mechanical properties from the second polymer (e.g., formed upon polymerization of the second polymerizable monomer). In some embodiments, the first polymer comprises a hardness less than the hardness of the second polymer.

Polymer composites and composite materials described herein may have enhanced physical properties when compared with homopolymers of similar monomer species and/or when compared with homogenously formed materials (e.g., not including the first and second continuous phases described herein). For example, a composite with a first polymer having high strength (e.g., storage modulus) and a second polymer having high flexibility can result in a composite with higher toughness than a homopolymer of either monomer species.

In some embodiments, the polymer is a molecule composed of repeating structural units (e.g., monomers) connected by covalent chemical bonds and characterized by a substantial number of repeating units. In some embodiments, a polymer comprises equal to or greater than 10 repeating units. In certain embodiments, a polymer comprises equal to or greater than 50 repeating units. In some embodiments, a polymer comprises equal to or greater than 100 repeating units. In some embodiments, a polymer has a high molecular weight (e.g., greater than or equal to 5,000 Da). Polymers are commonly the polymerization product of one or more species of monomer precursors. In certain embodiments, a polymer is a homopolymer consisting a single species of repeating monomer subunit. In some embodiments, a polymer is a copolymer comprising two or more different species of monomers linked in the same polymer. Copolymers may comprise two or more monomer subunits, and include random, block, alternating, segmented, grafted, tapered, and other copolymers. The term polymer also includes dendrimers, branched polymers, and cross-linked polymers. The term polymer can refer to inorganic polymers, organic polymers, or hybrid polymers. Useful polymers include organic polymers or inorganic polymers. In some embodiments, the polymer comprises a homopolymer, a linear copolymer, a block copolymer, an alternating copolymer, a periodic copolymer, a statistical copolymer, a random copolymer, a gradient copolymer, a branched copolymer, a brush copolymer, a comb copolymer, a dendrimer, or any combination thereof. In some embodiments, polymers disclosed herein are crosslinked.

In some embodiments, a plurality of monomeric units form an oligomer, and the oligomer is composed of repeating structural units connected by covalent chemical bonds which can be characterized by a number of repeating units less than that of a polymer (e.g., equal to or less than 20, 10 repeating units) and/or a lower molecular weights (e.g., less than or equal to 5,000 Da) than polymers. In some embodiments, oligomers are the polymerization product of one or more species of monomer precursors.

In certain embodiments, a polymer is formed via a polymerization reaction of polymer precursors. In some embodiments, a resin is a viscous substance comprising polymer precursors. In some embodiments, a resin can comprise a plurality of components, such as monomer components which can be selectively activated to form polymers (e.g., they are polymerizable components, such as the first polymerizable monomer and the second polymerizable components described herein). The monomer components within the resin may undergo polymerization to form a polymer. In some embodiments, a resin comprises more than one type or species of monomer component. In some embodiments, a resin herein comprises a first monomer component that has a different reactivity than a second monomer component. In certain embodiments, the resin comprises a first monomer component that is more reactive than the second monomer component. Differences in reactivity can be due to, as non-limiting examples, differences in reactivity at a given photopolymerization wavelength, differences in reactivity at a given temperature (e.g., during thermal curing), and/or differences in chemical rates of reactivity. In some embodiments, the resin comprises a third monomer component that can undergo polymerization. In some embodiments, the resin comprises more than three monomer components, each of which can undergo polymerization.

In some embodiments, differences in reactivity between the first polymerizable component and the second polymerizable component are due to differences in chemical reactivity rate. In some embodiments, the component having the first reactivity is a methacrylate and the component having the second reactivity is an acrylate. In some embodiments, the methacrylate component is more reactive than the acrylate component. In embodiments wherein the first polymerizable component is a methacrylate and the second polymerizable component is an acrylate, the resin comprises a soft methacrylate phase and a hard, less reactive acrylate phase. In some embodiments, the component having the first reactivity rate is an acrylate and the component having the second reactivity rate is a methacrylate. In embodiments wherein the first polymerizable component is an acrylate and the second polymerizable component is a methacrylate, the resin comprises a soft acrylate phase and a hard, less reactive methacrylate phase.

In some embodiments, the resin comprises at least two components having distinct reactivities (e.g., one polymerizing at a faster rate than the other). In some embodiments, it is preferential that the component corresponding with the soft phase (i.e., the soft continuous phase) is polymerized prior to the component corresponding with the hard phase (i.e., the hard continuous phase). In some embodiments, it is preferable that the soft phase of the resin is cured before the hard phase. As a non-limiting example, a resin comprising a methacrylate component corresponding to the soft phase and an acrylate component corresponding to the hard phase is preferentially cured such that the soft phase (methacrylate component) polymerizes prior to (and/or faster than) the curing of the hard phase (acrylate component). Such curing of the soft phase prior to the hard phase can, for example, can improve material properties such as increased modulus and longer elongation properties. In some embodiments, improved material properties of the formed material are observed when applying an acrylate component in the formation of the hard phase and a methacrylate component in the formation of the soft phase when the composite material is compared to traditional materials (e.g., applying the methacrylate component (having higher modulus) in the hard phase and the acrylate component in the soft phase).

In various instances, methacrylates have a higher glass transition temperature ($T_g$) in comparison to corresponding acrylates and thus are typically preferred during the production of hard materials, such as the production of a hard phase. In contrast, in some embodiments disclosed herein, an acrylate is applied for the production of the hard phase and a methacrylate is applied for the production of the soft phase. By forming a hard phase from acrylate components, there can be a small reduction in glass transition temperature but a better separation of the phases, which can improve overall toughness of the produced composite material. Thus, in certain embodiments, the resin disclosed herein comprises an acrylate component and a methacrylate component, wherein upon polymerization the resulting composite material includes a hard phase comprising the acrylate component and a soft phase comprising the methacrylate component. In some embodiments, such composite materials have increased overall toughness when compared to materials having a hard phase comprising the methacrylate component and a soft phase comprising the acrylate component.

In some embodiments, the first component or the second component comprises a vinyl ester. In some embodiments, it is favorable to use a component comprising a vinyl ester as the less-reactive component. In some embodiments, the component having the second reactivity (e.g., the second component corresponding with the hard phase) is a vinyl ester. In some embodiments, the component having the first reactivity rate (e.g., the first polymerizable monomer) is an acrylate. In some embodiments, the first polymerizable component is a methacrylate. In certain embodiments, the first polymerizable component is an acrylate and the second polymerizable component is a vinyl ester. In certain embodiments, the first polymerizable component is a methacrylate and the second polymerizable component is a vinyl ester. In some embodiments, the second polymerizable component—vinyl ester—when cured forms a relatively hard polymer (i.e., has a higher hardness than the polymer formed from the first polymerizable component). In some embodiments, the second polymerizable component—vinyl ester—when cured forms the hard continuous phase.

In some embodiments, the resin comprises 3, 4, 5, 6, or more than 6 phases. In some embodiments, the resin comprises 3, 4, 5, 6, or more than 6 continuous phases. In some embodiments, the resin comprises a plurality of hard phases. In certain embodiments, the resin comprises a plurality of hard continuous phases. In some embodiments, the resin comprises a plurality of soft phases. In certain embodiments, the resin comprises a plurality of soft continuous phases.

In some embodiments, the resin further comprises a third phase, a fourth phase, or more than four phases. In some embodiments, the third phase comprises a filler, a polymer, or an unreactive component. In some embodiments, the third phase is a filler. In some embodiments, the third phase is an unreactive component. In some embodiments, the third phase is a polymer. In some embodiments, the polymer is a thermoplastic. In certain embodiments, the polymer comprises polystyrene and/or copolymers containing polystyrene blocks.

In some embodiments, a thermoplastic, plastic, or thermoset is dissolved in the resin (e.g., as a third phase). In some embodiments, the added component (e.g., thermoplastic, plastic, or thermoset) is mixed homogenously into the resin, and during or following polymerization, the added component precipitates out as its own phase. In some embodiments, the added component precipitates out as its own continuous phase. In some embodiments, the added component (e.g., thermoplastic, plastic, or thermoset) forms an emulsion in the resin (i.e., is phase-separated prior to polymerization) and following polymerization, the added component forms its own continuous phase. In certain embodiments, the continuous phase is interpenetrated into the polymer network of the hard and soft phases.

In some embodiments, the third phase comprises a plastic, a thermoset, and/or a thermoplastic. Examples of plastics include, but are not limited to, a plastic or mixtures of plastics selected from the group consisting of: a polyolefin, a polyester, a polyacrylate, polymethacrylates, polystyrenes, polypropylenes, polyethylenes, polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers. In some embodiments, the plastic, thermoset, and/or thermoplastic component has a reactive functionality of at least one. In some embodiments, the plastic, thermoset, and/or thermoplastic component has a reactive functionality of more than one (e.g., thermosets having more than one reactive functional group). In such embodiments, the added third phase can form its own phase as described herein but can be chemically connected to another phase (e.g., the soft and/or hard phase). In some embodiments, the third phase comprises a styrenic block copolymer, a silicone rubber, an elastomeric alloy, a thermoplastic elastomer, a thermoplastic vulcanizate elastomer, a polyurethane elastomer, a block copolymer elastomer, a polyolefin blend elastomer, a thermoplastic co-polyester elastomer, or a thermoplastic polyamide elastomer.

In some embodiments, the resin further comprises a thermal initiator, a polymerization catalyst, a polymerization inhibitor, a light blocker, a plasticizer, a solvent, a surface energy modifier (e.g., a mold releasing agent), a pigment, a dye, a filler, a crystallization seed, a crystallization catalyst, a biologically significant chemical, or any combination thereof.

In some embodiments, the resin comprises a filler. In some embodiments, the filler has a glass transition temperature ($T_g$) respective of the resin formulation. In certain embodiments, the resin comprises a discontinuous phase comprising the filler, as further described herein (e.g., as a third phase). In some embodiments, the resin comprises a continuous phase comprising the filler (e.g., a filler comprising fibers, or functionalized fillers). In certain embodiments, the filler comprises a fiber. In some embodiments, the filler is functionalized. In some embodiments, the filler is functionalized with a reactive functional group as described herein. In certain embodiments, the filler comprises a functionalized fiber. In some embodiments, the filler comprises calcium carbonate (i.e., chalk), kaolin, metakaolinite, a kaolinite derivative, magnesium hydroxide (i.e., talc), calcium silicate (i.e., wollastonite), a glass filler (e.g., glass beads, short glass fibers, or long glass fibers), a nanofiller (e.g., nanoplates, nanofibers, or nanoparticles), a silica filler (e.g., a mica, silica gel, fumed silica, or precipitated silica), carbon black, dolomite, barium sulfate, ATH Al(OH)$_3$, MDH Mg(OH)$_2$, diatomaceous earth, magnetite, halloysite, zinc oxide, titanium dioxide, cellulose, lignin, a carbon filler (e.g., chopped carbon fiber or carbon fiber), a derivative thereof, or a combination thereof.

In some embodiments, the resin comprises a thermal initiator. In some embodiments, the thermal initiator comprises an azo compound, an inorganic peroxide, an organic peroxide, or any combination thereof. In some embodiments, the thermal initiator is selected from the group consisting of tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis(tert-butyl-peroxy-2,5-dimethylhexane, 2,5-bis(tert-butylperoxy)-2,5-dimethyl-3-hexyne, bis(1-(tert-butylperoxy)-3,3,5-trimethylcyclohexane, tert-butyl hydroxyperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, potassium persulfate, a derivative thereof, and a combination thereof. In some embodiments, the thermal initiator comprises a thermal acid generator or a thermal base generator.

In some embodiments, the resin comprises a polymerization catalyst. In some embodiments, the polymerization catalyst comprises a tin catalyst, a platinum catalyst, a rhodium catalyst, a titanium catalyst, a silicon catalyst, a palladium catalyst, a metal triflate catalyst, a boron catalyst, a bismuth catalyst, or any combination thereof. Non-limiting examples of a titanium catalyst include di-n-butylbutoxychlorotin, di-n-butyldiacetoxytin, di-n-butyldilauryltin, dimethyldineodecanoatetin, dioctyldilauryltin, tetramethyltin, and dioctylbis(2-ethylhexylmaleate)tin. Non-limiting examples of a platinum catalyst include platinum-divinyltetramethyl-disiloxane complex, platinum-cyclovinylmethyl-siloxane complex, platinum-octanal complex, and platinum carbonyl cyclovinylmethylsiloxane complex. A non-limiting example of a rhodium catalyst includes tris(dibutylsulfide) rhodium trichloride. Non-limiting examples of a titanium catalyst includes titanium isopropoxide, titanium 2-ethylhexoxide, titanium chloride triisopropoxide, titanium ethoxide, and titanium diisopropoxide bis(ethylacetoacetate). Non-limiting examples of a silicon catalyst include tetramethylammonium siloxanolate and tetramethylsilylmethyltrifluoromethanesulfonate. A non-limiting example of a palladium catalyst includes tetrakis(triphenylphosphine)palladium(0). Non-limiting examples of a metal triflate catalyst include scandium trifluoromethanesulfonate, lanthanum trifluoromethanesulfonate, and ytterbium trifluoromethanesulfonate. A non-limiting example of a boron catalyst includes tris(pentafluorophenyl)boron. Non-limiting examples of a bismuth catalyst include bismuth-zinc neodecanoate, bismuth 2-ethylhexanoate, a metal carboxylate of bismuth and zinc, and a metal carboxylate of bismuth and zirconium.

In some embodiments, the resin comprises a polymerization inhibitor in order to stabilize the composition and prevent premature polymerization. In some embodiments, the polymerization inhibitor is a photopolymerization inhibitor (e.g., oxygen). In some embodiments, the polymerization inhibitor is a phenolic compound (e.g., BHT). In some embodiments, the polymerization inhibitor is a stable radical (e.g., 2,2,4,4-tetramethylpiperidinyl-1-oxy radical, 2,2-diphenyl-1-picrylhydrazyl radical, galvinoxyl radical, or triphenylmethyl radical). In some embodiments, more than one polymerization inhibitor is present in the resin. In some embodiments, the polymerization inhibitor acts as a radical scavenger. In certain embodiments, the polymerization inhibitor is an antioxidant, a hindered amine light stabilizer (HAL), a hindered phenol, or a deactivated radical (e.g., a peroxy compound). In some embodiments, the polymerization inhibitor is selected from the group consisting of 4-tert-butylpyrocatechol, tert-butylhydroquinone, 1,4-benzoquinone, 6-tert-butyl-2,4-xylenol, 2-tert-butyl-1,4-benzoquinone, 2,6-di-tert-butyl-p-cresol, 2,6-di-tert-butylphenol, 1,1-diphenyl-2-picrylhydrazyl free radical, hydroquinone, 4-methoxyphenol, phenothiazine, any derivative thereof, and any combination thereof.

In some embodiments, the resin comprises a light blocker in order to dissipate UV radiation. In some embodiments, the light blocker absorbs a specific UV energy value and/or range. In some embodiments, the light blocker is a UV light absorber, a pigment, a color concentrate, or an IR light absorber. In some embodiments, the light blocker comprises a benzotriazole (e.g., 2-(2'-hydroxy-phenyl benzotriazole), a hydroxyphenyltriazine, an oxanilide, a benzophenone, or a combination thereof.

In some embodiments, the resin comprises a pigment, a dye, or a combination thereof. A pigment can be a suspended solid that may be insoluble in the resin. A dye can be dissolved in the resin. In some embodiments, the pigment comprises an inorganic pigment. In some embodiments, the inorganic pigment comprises an iron oxide, barium sulfide, zinc oxide, antimony trioxide, a yellow iron oxide, a red iron oxide, ferric ammonium ferrocyanide, chrome yellow, carbon black, or aluminum flake. In some embodiments, the pigment comprises an organic pigment. In some embodiments, the organic pigment comprises an azo pigment, an anthraquinone pigment, a copper phthalocyanine (CPC) pigment (e.g., phthalo blue or phthalo green) or a combination thereof. In some embodiments, the dye comprises an azo dye (e.g., a diarylide or Sudan stain), an anthraquinone (e.g., Oil Blue A or Disperse Red 11), or a combination thereof.

In some embodiments, the resin comprises a surface energy modifier. In some embodiments, the surface energy modifier can aid the process of releasing a polymer from a mold. In some embodiments, the surface energy modifier can act as an antifoaming agent. In some embodiments, the surface energy modifier comprises a defoaming agent, a deairation agent, a hydrophobization agent, a leveling agent, a wetting agent, an emulsion stabilizer, an emulsion destabilizer, or an agent to adjust the flow properties of the resin. In some embodiments, the surface energy modifier comprises an aloxylated surfactant, a silicone surfactant, a sulfosuccinate, a fluorinated polyacrylate, a fluoropolymer, a silicone, a star-shaped polymer, an organomodified silicone, or any combination thereof.

In some embodiments, the resin comprises a plasticizer. A plasticizer can be a nonvolatile material that can reduce interactions between polymer chains, which can decrease glass transition temperature, melt viscosity, and elastic modulus. In some embodiments, the plasticizer comprises a dicarboxylic ester plasticizer, a tricarboxylic ester plasticizer, a trimellitate, an adipate, a sebacate, a maleate, or a bio-based plasticizer. In some embodiments, the plasticizer comprises a dicarboxylic ester or a tricarboxylic ester comprising a dibasic ester, a phthalate, bis(2-ethylhexyl) phthalate (DEHP), bis(2-propylheptyl) phthalate (DPHP), diisononyl phthalate (DINP), di-n-butyl phthalate (DBP), butyl benzyl phthalate (BBzP), diisodecyl phthalate (DIDP), dioctyl phthalate (DOP), diisooctyl phthalate (DIOP), diethyl phthalate (DEP), diisobutyl phthalate (DIBP), di-n-hexyl phthalate, a derivative thereof, or a combination thereof. In some embodiments, the plasticizer comprises a trimellitate comprising trimethyl trimellitate (TMTM), tri-(2-ethylhexyl) trimellitate (TEHTM), tri-(n-octyl,n-decyl) trimellitate (ATM), tri-(heptyl,nonyl) trimellitate (LTM), n-octyl trimellitate (OTM), trioctyl trimellitate, a derivative thereof, or a combination thereof. In some embodiments, the plasticizer comprises an adipate comprising bis(2-ethylhexyl) adipate (DEHA), dimethyl adipate (DMAD), monomethyl adipate (MMAD), dioctyl adipate (DOA), Bis[2-(2-butoxyethoxy)ethyl] adipate, dibutyl adipate, diisobutyl adipate, diisodecyl adipate, a derivative thereof, or a combination thereof. In some embodiments, the plasticizer comprises a sebacate comprising dibutyl sebacate (DBS), Bis(2-ethylhexyl) sebacate, diethyl sebacate, dimethyl sebacate, a derivative thereof, or a combination thereof. In some embodiments, the plasticizer comprises a maleate comprising Bis(2-ethylhexyl) maleate, dibutyl maleate, diisobutyl maleate, a derivative thereof, or a combination thereof. In some embodiments, the plasticizer comprises a bio-based plasticizer comprising an acetylated monoglyceride, an alkyl citrate, a methyl ricinoleate, or a green plasticizer. In some embodiments, the alkyl citrate is selected from the group consisting of triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, a derivative thereof, or a combination thereof. In some embodiments, the green plasticizer is selected from the group consisting of epoxidized soybean oil, epoxidized vegetable oil, epoxidized esters of soybean oil, a derivative thereof, or a combination thereof. In some embodiments, the plasticizer comprises an azelate, a benzoate (e.g., sucrose benzoate), a terephthalate (e.g., dioctyl terephthalate), 1,2-cyclohexane dicarboxylic acid diisononyl ester, alkyl sulphonic acid phenyl ester, a sulfonamide (e.g., N-ethyl toluene sulfonamide, N-(2-hydroxypropyl) benzene sulfonamide, N-(n-butyl) benzene sulfonamaide), an organophosphate (e.g., tricresyl phosphate or tributyl phosphate), a glycol (e.g., triethylene glycol dihexanoate or tetraethylene glycol diheptanoate), a polyether, a polymeric plasticizer, polybutene, a derivative thereof, or a combination thereof.

In some embodiments, the resin comprises a solvent. In some embodiments, the solvent comprises a nonpolar solvent. In certain embodiments, the nonpolar solvent comprises pentane, cyclopentane, hexane, cyclohexane, benzene, toluene, 1,4-dioxane, chloroform, diethyl ether, dichloromethane, a derivative thereof, or a combination thereof. In some embodiments, the solvent comprises a polar aprotic solvent. In certain embodiments, the polar aprotic solvent comprises tetrahydrofuran, ethyl acetate, acetone, dimethylformamide, acetonitrile, DMSO, propylene carbonate, a derivative thereof, or a combination thereof. In some embodiments, the solvent comprises a polar protic solvent. In certain embodiments, the polar protic solvent comprises formic acid, n-butanol, isopropyl alcohol, n-propanol, t-butanol, ethanol, methanol, acetic acid, water, a derivative thereof, or a combination thereof.

In some embodiments, the resin comprises a biologically significant chemical. In some embodiments, the biologically significant chemical comprises a hormone, an enzyme, an active pharmaceutical ingredient, an antibody, a protein, a drug, or any combination thereof. In some embodiments, the biologically significant chemical comprises a pharmaceutical composition, a chemical, a gene, a polypeptide, an enzyme, a biomarker, a dye, a compliance indicator, an antibiotic, an analgesic, a medical grade drug, a chemical agent, a bioactive agent, an antibacterial, an antibiotic, an anti-inflammatory agent, an immune-suppressive agent, an immune-stimulatory agent, a dentinal desensitizer, an odor masking agent, an immune reagent, an anesthetic, a nutritional agent, an antioxidant, a lipopolysaccharide complexing agent or a peroxide.

In some embodiments, the first component and/or the second component comprises at least one reactive functional group. In certain embodiments, the reactive functional groups allow for further modification of the polymeric material, such as additional polymerization. In some embodiments, the first polymerizable component and/or the second polymerizable component comprises 1, 2, 3, 4, 5, 6, 7, 8, 9, 10, or more than 10 reactive functional groups. The reactive functional groups can be the same, or they can be of different functionality. In some embodiments, the one or more functional groups are at the terminal end(s) of the first polymerizable component and/or the second polymerizable component (e.g., wherein the first polymerizable component and/or the second polymerizable component are components of first and second polymerizable oligomers). In some embodiments, the plurality of reactive functional groups are the same. In other embodiments, the plurality of reactive functional groups are different from one another. In some embodiments, the plurality of reactive functional groups comprises at least two functional groups that are the same.

Non-limiting examples of reactive functional groups include free radically polymerizable functionalities, photoactive groups, groups facilitating step growth polymerization, thermally reactive groups, and/or groups that facilitate bond formation (e.g., covalent bond formation). In some embodiments, the functional groups comprise an acrylate, a methacrylate, an acrylamide, a vinyl group, a vinyl ether, a thiol, an allyl ether, a norbornene, a vinyl acetate, a maleate, a fumarate, a maleimide, an epoxide, a ring-strained cyclic ether, a ring-strained thioether, a cyclic ester, a cyclic carbonate, a cyclic silane, a cyclic siloxane, a hydroxyl, an amine, an isocyanate, a blocked isocyanate, an acid chloride, an activated ester, a Diels-Alder reactive group, a furan, a cyclopentadiene, an anhydride, a group favorable toward photodimerization (e.g., an anthracene, an acenaphthalene, and/or a coumarin), a group that photodegrades into a reactive species (e.g., Norrish Type 1 and 2 materials), an azide, a derivative thereof, or a combination thereof.

In some embodiments, the first polymerizable component comprises more functional groups (also referred to herein as reactive functional groups) than the second polymerizable component. In some embodiments, the first component is difunctional, trifunctional, or comprises more than 3 functional groups, and the second component comprises fewer functional groups. In some embodiments, the first component is difunctional and the second component is monofunctional. In some embodiments, the first polymerizable component is a difunctional acrylate and the second polymerizable component is a monofunctional methacrylate.

In some embodiments, the resin forms an interpenetrating network of polymers (IPN) upon polymerization. In some embodiments, at least one of the phases of the resin comprises an interpenetrating network of polymers. In certain embodiments, one of the phases of the resin comprises an interpenetrating network of polymers. In certain embodiments, the resin comprises an interpenetrating network of polymers and the IPN forms the first phase and the second phase upon curing (i.e., in some embodiments the multiphase resins described herein comprise a singular IPN formulation prior to polymerization and form multiphase composite materials as described herein following polymerization). In some embodiments, the IPN phase of a resin comprises a first phase (i.e., first continuous phase) and second phase (i.e., second continuous phase) as described further herein. In some embodiments, a resin comprising an IPN formulation can form more than 2 phases, such as 3 phases, 4 phases, or more than 4 phases.

In some embodiments, interpenetrating polymer networks form a plurality (e.g., two or more) interpenetrating networks. In some embodiments, the interpenetrating polymer networks form a plurality of interpenetrating phases (e.g. continuous phases) upon curing. In certain embodiments, the IPNs form interpenetrating networks by a difference in reaction mechanism. For example, a resin comprising a free radically polymerizable monomer system and an ionically polymerizable monomer system can be mixed together, and upon initiation of polymerization, both systems may start to polymerize, but the free radical system reacts faster (e.g., is kinetically faster) and cures faster than the ionically polymerizable system. In some embodiments, the first polymerizable component is free-radically polymerizable (i.e., is polymerizable by free-radical polymerization). In some embodiments, the second polymerizable component is ionically polymerizable (i.e., is polymerizable by ionic polymerization). In some embodiments, the second polymerizable component is an ionically polymerizable monomer. In some embodiments, the initiation of the polymerization of the ionically polymerizable system and the radically polymerizable system occur concurrently or nearly at the same time, and the radical system is almost fully cured (e.g., at least 80% cured, at least 90% cured, at least 95% cured, or at least 99% cured) before the ionically polymerizable system is considerably cured (e.g., is less than 10% cured, or is less than 5% cured). Thus, in such embodiments, activation of polymerization may take place using two processes separated by a short period of time (e.g., milliseconds) allowing for multiple polymerization reactions to take place across the distinct phases, but the more reactive phase (e.g., radical monomers) can be substantially cured prior to considerable curing of the less reactive phase (e.g., ionic monomers). In some embodiments, greater than 70% greater than 80%, greater than 90%, greater than 95%, or greater than 99% of the radically polymerizable monomer system is polymerized prior to 10% of the ionically polymerizable system being polymerized. In some embodiments, greater than 70% greater than 80%, greater than 90%, greater than 95%, or greater than 99% of the radically polymerizable monomer system is polymerized prior to 5% of the ionically polymerizable system being polymerized. In some embodiments, the initiation of polymerization of the two phases occurs at the same time. In some embodiments, the initiation of polymerization of the two phases occurs at nearly the same time (e.g., within 10's of milliseconds). In some embodiments, the initiation of polymerization of the two phases comprises two distinct processing steps, as further described herein. In such embodiments, the free radical polymer forms its own phase from the IPN resin while the ionic system becomes its own phase as it continues to polymerize.

In certain embodiments, the IPN system comprises an acrylate component or methacrylate component mixed with ionically-cured epoxides (e.g., cationically-cured epoxides). In some embodiments, the component having the first reactivity rate comprises an acrylate monomer. In some embodiments, the component having the first reactivity rate comprises a methacrylate monomer. In some embodiments, the component having the second reactivity rate comprises an epoxide. In certain embodiments, the second polymerizable component is an epoxide. In certain embodiments, the epoxide is a cationically-curable epoxide. In certain embodiments, the epoxide is a cationically-cured epoxide.

In some embodiments, the interpenetrating network of polymers (IPN) comprises an additional system, such that three or more phases form upon curing of the resin. As a non-limiting example, an inert filler (e.g., fumed silica or talc, or another filler as further described herein) can be added to the aforementioned IPN resins, and following curing the resulting material can have a hard continuous phase, a soft continuous phase, and islands of filler material (i.e., a discontinuous phase). In some embodiments, an additional system is an additional monomer system. As a non-limiting example, an added polymer system (e.g., polystyrene) can be added to an IPN and is formulated such that it is soluble in the resin stage of the IPN system, but following polymerization, the polystyrene precipitates out as its own separate phase, thus the material would include a hard continuous phase, a soft continuous phase, and a third continuous phase comprising polystyrene. In some embodiments, the additional monomer system is interpenetrated into the IPN. As another non-limiting example, an IPN resin comprising an additional polymer system (e.g., polystyrene) and a filler can, following polymerization, comprise four phases (e.g., a hard continuous phase, a soft continuous phase, a polystyrene continuous phase, and a discontinuous filler phase). In some embodiments, the IPN resin systems described above further comprise a thermoplastic, plastic, or thermoform, as described further herein (e.g., polystyrene). In some embodiments, the IPN resin systems further comprise a filler, as further described herein.

In some embodiments, the first polymerizable component and the second polymerizable component have the same number of functional groups, and a difference in rate of reactivity comprises a difference in component size. In some embodiments, the first polymerizable component is smaller than the second polymerizable component.

In certain embodiments, the resin comprises a methacrylate component that is less reactive than an acrylate component. As a non-limiting example, an acrylate component that is smaller and/or more functionalized (e.g., difunctionalized) than a methacrylate component (e.g., larger and/or monofunctional) may tend to react faster than the methacrylate component (i.e., the acrylate is more reactive than the methacrylate). As described further herein, in some embodiments it is beneficial that the soft phase polymerizes prior to the hard phase, thus in such embodiments as described above the more-reactive component corresponds with the soft phase and the less-reactive component corresponds with the hard phase. As a non-limiting example, in some embodiments the soft phase of the resin corresponds to an acrylate component and the hard phase of the resin corresponds to a methacrylate component, such as when the acrylate component is more reactive than the methacrylate component, as described herein.

In some embodiments, the first polymerizable component is an acrylate and the second polymerizable component is a methacrylate, wherein the methacrylate is larger than the acrylate (e.g., sterically larger and/or larger based on a calculated molecular surface area). In some embodiments, it is beneficial that the component comprising acrylate polymerizes more preferentially than the component comprising methacrylate. In some embodiments, the resin comprises a methacrylate component and an acrylate component, and the methacrylate component polymerizes preferentially to the acrylate (i.e., the methacrylate is more reactive in its polymerization than the acrylate). In some embodiments, the soft phase of the resin corresponds with the methacrylate component. In certain embodiments, the soft phase of the resin is characterized by the presence of the methacrylate component. In some embodiments, the hard phase of the resin is characterized by the presence of the acrylate component. In certain embodiments, the hard phase of the resin corresponds with the acrylate component. In some embodiments, the first polymerizable component is a difunctional acrylate, the second polymerizable component is a difunctional methacrylate, and the methacrylate is larger than the acrylate. In some embodiments, the acrylate component is larger than the methacrylate component. In some embodiments, the acrylate component is more functionalized than the methacrylate component (e.g., as non-limiting examples, the acrylate component is difunctionalized and the methacrylate component is monofunctionalized, or the acrylate component is trifunctionalized and the methacrylate component is monofunctionalized or difunctionalized).

In some embodiments, the resin is a light polymerizable liquid composition. In some embodiments, the resin comprises a first polymerizable component (e.g., first component), a second polymerizable component (e.g., second component), and a photoinitiator. In some embodiments, the resin has a liquid ratio of the first polymerizable component to the second polymerizable component. In some embodiments, the liquid ratio is the same throughout the resin (e.g., a homogenous resin). In certain embodiments, the liquid ratio has localized characteristics, wherein the ratio depends on the location in the resin that the ratio is determined. As a non-limiting example, differences in density and/or immiscibility may cause separation of phases or of polymerizable components into sections, wherein one localized point of the resin can comprise a liquid ratio that is different from the liquid ratio of a different localized point within the resin.

In some embodiments, the resin is exposed to a source of light which initiates polymerization of the first and/or second polymer, thereby forming a first polymer region or second polymer region, respectively. In some embodiments the resin is exposed to a source of light which initiates polymerization of the first or second polymer, thereby forming a first polymer region or second polymer region, respectively. In some embodiments, the resin is processed separately. In certain embodiments, processing a resin separately comprises polymerization of some but not all polymerizable components. For example, in some embodiments, exposure to a source of light (e.g., for photopolymerization) polymerizes the first polymerizable component but the second polymerizable component is not (e.g., measurably) polymerized or is not substantially polymerized (e.g., less than 5% of polymerizable component polymerizes). In some embodiments, exposure to a source of light polymerizes the second polymerizable component but the first polymerizable component is not polymerized or is not substantially polymerized. In some embodiments, the first polymerizable component and the second polymerizable component have different rates of polymerization when photopolymerized at a specified wavelength of light. In some embodiments, the first polymerizable component and the second polymerizable component have different rates of polymerization when polymerized at a specified temperature. In some embodiments, the first polymer region has a first ratio of the first polymerizable component to the second polymerizable component. In certain embodiments, light exposure activates the polymerization of a first polymer. In some embodiments, the first polymerizable component can diffuse freely through the resin, the second polymerizable component can diffuse freely through the resin, both the first and the second polymerizable components can diffuse freely through the resin, the first polymerizable component can diffuse freely through the first polymer, the second polymerizable component can diffuse freely through the first polymer, and/or both the first and the second polymerizable components can diffuse freely through the first polymer.

In some embodiments, the rate of polymerization of the first polymerizable component is greater than the rate of polymerization of the second polymerizable component at a processing step. In some embodiments, the processing step is exposure to a specified wavelength of light. In some embodiments, the processing step is exposure to a specified temperature. In some embodiments, the processing step comprises exposure to a specified wavelength of light, exposure to a specified temperature, or a combination thereof. In some embodiments, the rate of polymerization of the first polymerizable component is greater than 1-times, greater than or equal to 2-times, greater than or equal to 3-times, greater than or equal to 4-times, greater than or equal to 5-times, greater than or equal to 10-times, greater than or equal to 20-times, greater than or equal to 30-times, greater than or equal to 40-times, greater than or equal to 50-times, or greater than or equal to 100-times faster than the rate of polymerization of the second polymerizable component. In some embodiments, the specified wavelength of light comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm. In some embodiments, the specified temperature is a use temperature. As used herein, the use temperature can be a temperature less than or equal to 20° C., from 20° C. to 40° C., or greater than or equal to 40° C. In preferred embodiments, the use temperature comprises a temperature from 20° C. to 40° C. In other preferred embodiments, the use temperature is between 50° C. and 100° C. In still other embodiments, the use temperature is between 100° C. and 150° C. In still other embodiments, the use temperature is above 150° C.

In some embodiments, the rate of polymerization of the second polymerizable component is greater than the rate of polymerization of the first polymerizable component at a processing step. In some embodiments, the processing step is exposure to a specified wavelength of light. In some embodiments, the processing step is exposure to a specified temperature. In some embodiments, the processing step comprises exposure to a specified wavelength of light, exposure to a specified temperature, or a combination thereof. In some embodiments, the rate of polymerization of the second polymerizable component is greater than or equal to 1-times, greater than or equal to 2-times, greater than or equal to 3-times, greater than or equal to 4-times, greater than or equal to 5-times, greater than or equal to 10-times, greater than or equal to 20-times, greater than or equal to 30-times, greater than or equal to 40-times, greater than or equal to 50-times, or greater than or equal to 100-times faster than the rate of polymerization of the first polymerizable component. In some embodiments, the specified wavelength of light comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm. In some embodiments, the specified temperature is a use temperature. In some embodiments, the use temperature is from −50° C. to 500° C., from −10° C. to 300° C., from −5° C. to 200° C., from 0° C. to 100° C., from 10° C. to 90° C., or from 20° C. to 80° C. In some embodiments, the use temperature is a temperature less than or equal to 20° C., from 20° C. to 40° C., or greater than or equal to 40° C. In preferred embodiments, the use temperature comprises a temperature from 20° C. to 40° C. In other preferred embodiments, the use temperature is between 50° C. and 100° C. In still other embodiments, the use temperature is between 100° C. and 150° C. In still other embodiments, the use temperature is above 150° C.

Photopolymerization can occur when suitable formulations (e.g., the resins disclosed herein) are exposed to radiation (e.g., UV or visible light) of sufficient power and of a wavelength capable of initiating polymerization. The wavelengths and/or power of radiation useful to initiate polymerization may depend on the photoinitiator used. "Light" as used herein includes any wavelength and power capable of initiating polymerization. Some wavelengths of light (e.g., the specified wavelength of light) include ultraviolet (UV) or visible light. UV light sources include UVA (wavelength about 400 nanometers (nm) to about 320 nm), UVB (about 320 nm to about 290 nm) or UVC (about 290 nm to about 100 nm). Any suitable source may be used, including laser sources. The source may be broadband or narrowband, or a combination thereof. The light source may provide continuous or pulsed light during the process. Both the length of time the system is exposed to UV light and the intensity of the UV light can be varied to determine the ideal reaction conditions.

In some embodiments, regions of polymerization are spatially controllable. In some embodiments, the resin is exposed to a region of light (e.g., a first exposure region), which can initiate polymerization and generate a first polymer region. In certain embodiments, the size and/or shape of the first polymer region is controlled by selective exposure to light, e.g., through use of a mask. In some embodiments, the polymerizable components can diffuse through the resin during the polymerization of the first polymer region, thus increasing or decreasing the amount of polymerizable component in the region. As a non-limiting example, the light activated polymerization of the first polymerizable component into the first polymer in the first polymer region, combined with diffusion of the components, can result in the migration of first polymerizable components into the first polymer region, thus increasing the first ratio of the first polymerizable component to the second polymerizable component within the first polymer region, while decreasing the ratio of the first polymerizable component to the second polymerizable component in a second region (e.g., the second ratio). In some embodiments, the second region is adjacent to, contacting, or overlapping with the first exposure region, and the second region is different from the first region. In certain embodiments, the resin ratio (the liquid ratio), the first region ratio, and the second region ratio of the first polymerizable component to the second polymerizable component are different.

In some embodiments, a polymerizable component is a monomer, a polymer, and/or an oligomer, which are capable of entering into polymerization through reactive groups. In some embodiments, a polymerizable component is a component of a solution or molecules in a solution that are capable of polymerizing, either with itself or with other components or molecules within the solution. In some embodiments, a first monomer, or monomer 1, is the first polymerizable component of a X,Y,Z volume that is preferentially polymerized upon initial exposure to a source of radiation (e.g., a specified wavelength of light). In some embodiments, a second monomer, or monomer 2, is a polymerizable component that is not preferentially polymerized upon initial exposure to a source of radiation. In some embodiments, the second monomer is preferentially polymerized upon initial exposure to a source of radiation (e.g., a specified wavelength of light) and the first monomer is not preferentially polymerized upon exposure to said source of radiation. In some embodiments a first polymer, or polymer 1, comprises at least a majority of monomer 1. In some embodiments a first polymer, or polymer 1, consists of monomer 1. In some embodiments a first polymer, or polymer 1, consists essentially of monomer 1. In some embodiments a second polymer, or polymer 2, comprises a majority of monomer 2. In some embodiments a second polymer, or polymer 2, consists essentially of monomer 2. In certain embodiments the first monomer comprises a first polymerizable component. In some embodiments, the second monomer comprises a second polymerizable component.

In some embodiments, oligomers and polymer mixtures can be characterized and differentiated from other mixtures of oligomers and polymers by measurements of molecular weight and molecular weight distributions. The following definitions of molecular weight can be applied for such characterization (see: L. H. Sperling, Introduction to Physical Polymer Science, $2^{nd}$ Ed., Wiley New York (1992)). The average Molecular Weight (M) is the Average Number of Repeating Units n (or dp.) x the molecular weight or molar mass (Mi) of the repeating unit. The number-average molecular weight ($M_n$) is the arithmetic mean, representing the total weight of the molecules present divided by the total number of molecules. Molecular weight may also be measured by the weight-average molecular weight (Mw) and the z-average molecular weight Mz.

In certain embodiments, this disclosure provides methods for the generation of composite polymer compositions utilizing a single resin. In some embodiments, the single resin comprises two types of monomer components, three types of monomer components, four types of monomer components, five types of monomer components, six types of monomer components, seven types of monomer components, eight types of monomer components, nine types of monomer components, ten types of monomer components, eleven types of monomer components, twelve types of monomer components, or more than twelve types of monomer components. In certain embodiments, the resin comprises 2 polymerizable components (also referred to herein as polymerizable monomers), 3 polymerizable components, 4 polymerizable components, 5 polymerizable components, 6 polymerizable components, 7 polymerizable components, 8 polymerizable components, 9 polymerizable components, 10 polymerizable components, 11 polymerizable components, 12 polymerizable components, 13 polymerizable components, 14 polymerizable components, 15 polymerizable components, or greater than 15 polymerizable components.

The monomer components may be polymerized to form a polymer (i.e., are polymerizable monomers). In some embodiments, the monomer components react only with their own type to form a homopolymer. In some embodiments, the monomer components react with other types of monomer components to form a copolymer, as described herein.

In some embodiments, the resin comprises a first component and a second component, wherein the two components have different reactivity. The reactivity is a determined value. A monomer's reactivity ratio is a value that compares the monomer's reactivity with a second monomer. Reactivity ratios of components are available in the art (see, e.g., G. Odian, Principles of Polymerization, $4^{th}$ Ed., 2004, which is incorporated herein by reference). In some embodiments, a reactivity ratio or ratio of reactivity refers to the ratio of a rate coefficient for the reaction of a monomer with itself to the rate coefficient of the monomer with that of a different monomer. In some embodiments, reactivity ratio is defined by the formula:

$$R = \frac{k_{11}}{k_{12}}$$

wherein $k_{11}$ is the rate coefficient corresponding to a reaction of monomer 1 (or a polymer with monomer 1 in a terminal position) with monomer 1 and $k_{12}$ is the rate constant coefficient to a reaction of monomer 1 (or a polymer with monomer 1 in a terminal position) with monomer 2. In certain embodiments, reactivity ratios depend on exposure to a specified temperature, concentration, functionality of the reactants, solubility parameters, exposure to a specified wavelength of light, and other physical conditions.

In certain embodiments, the reactivity ratio between the first component (e.g., first polymerizable monomer) and the second component (e.g., second polymerizable monomer) is greater than or equal to one. In some embodiments, the reactivity ratio between the first component and the second component is greater than or equal to 10, greater than or equal to 20, greater than or equal to 30, greater than or equal to 50, greater than or equal to 100, greater than or equal to 500, greater than or equal to 1000, greater than or equal to 5000, greater than or equal to 10000, greater than or equal to 50000, or greater than or equal to 100000. In some embodiments, the reactivity ratio between the first component and the second component is from 1 to 10, from 1 to 20, from 1 to 30, from 1 to 50, from 1 to 100, from 1 to 500, from 1 to 1000, from 1 to 5000, from 1 to 10000, from 1 to 50000, from 1 to 100000, from 2 to 10, from 2 to 20, from 2 to 30, from 2 to 50, from 2 to 100, from 2 to 500, from 2 to 1000, from 2 to 5000, from 2 to 10000, from 2 to 50000, or from 2 to 100000.

In some embodiments, the resin comprises the first component (e.g., first polymerizable monomer) and the second component (e.g., second polymerizable monomer), wherein one component is more reactive than the other. In some embodiments, the first component is at least 1.1-fold more reactive, at least 2-fold more reactive, at least 3-fold more reactive, at least 5-fold more reactive, at least 10-fold more reactive, at least 15-fold more reactive, at least 25-fold more reactive, at least 50-fold more reactive, at least 100-fold more reactive, at least 250-fold more reactive, at least 500-fold more reactive, at least 750-fold more reactive, at least 1000-fold more reactive, at least 1250-fold more reactive, at least 1500-fold more reactive, at least 2000-fold more reactive, at least 5000-fold more reactive, at least 10000-fold more reactive, at least 20000-fold more reactive, at least 50000-fold more reactive, or at least 100000-fold more reactive, than the second component in a polymerization reaction and under a given set of polymerization conditions. In some embodiments, the polymerization condition comprises exposure to a specified wavelength, exposure to a specified temperature, or any combination thereof. In some embodiments, the first component is infinitely more reactive than the second component in the polymerization condition.

In some embodiments, the resin comprising a first polymerizable component and the second polymerizable component undergoes polymerization to form a polymer. In some embodiments, the first polymerizable component is integrated into a first polymer. In some embodiments, the second polymerizable component is integrated into a second polymer. In certain embodiments, a polymerization activator initiates the polymerization. In some embodiments, the polymerization activator comprises a radical initiator, a photoinitiator, a thermal initiator, a catalyst, a reactive species, or any combination thereof.

In certain embodiments, the radical initiator is selected from a halogen, a chlorine, an azo compound, azobisisobutyronitrile (AIBN), 1,1'-azobis(cyclohexanecarbonitrile) (ABCN), an organic peroxide, di-tert-butyl peroxide, benzoyl peroxide, methyl ethyl ketone peroxide, acetone peroxide, an inorganic peroxide, a peroxydisulfate salt, a transition metal catalyst, or any combination thereof.

In some embodiments, the resin further comprises a photoinitiator. Photoinitiators in this disclosure include those that can be activated with light and initiate polymerization of the polymerizable components of the resin. In some embodiments, photoinitiators may be useful for various purposes, including for curing of polymers, including those that can be activated with light and initiate polymerization of the polymerizable components of the formulation. In some embodiments, the photoinitiator is a radical photoinitiator, a cationic initiator, and/or an anionic photoinitiator. In some embodiments, the photoinitiator is a Type I photoinitiator, which undergoes unimolecular bond cleavage to generate free radicals. In other embodiments the photoinitiator is a Type II photoinitiator which undergoes a bimolecular reaction to generate free radicals. Common Type I photoinitiators include, but are not limited to benzoin ethers, benzil ketals, α-dialkoxy-acetophenones, α-hydroxy-alkyl phenones and acyl-phosphine oxides. Common Type II photoinitiators include benzophenones/amines and thioxanthones/amines. Cationic initiators include aryldiazonium, diaryliodonium, and triarylsulfonium salts. In some embodiments, the initiator comprises a photobase generator.

In some embodiments the photoinitiator comprises an acetophenone, 2-benzyl-2-(dimethylamino)-4'-morpholinobutyrophenone, 4'-tert-butyl-2',6'-dimethylacetophenone, 2,2-diethyoxyacetophenone, 2,2-dimethoxy-2-phenylacetophenone, 4'-ethoxyacetophenone, 3'-hydroxyacetophenone, 4'-hydroxy-acetophenone, 1-hydroxycyclohexyl phenyl ketone, 2-hydroxy-4'-(2-hydroxyethoxy)-2-methylpropio-phenone, 2-hydroxy-2-methylpropiophenone, 2-methyl-4'-(methylthio)-2-morpholinopropiophenone, 4'-phenoxyacetophenone, a benzyl, a benzoin, benzoin ethyl ether, benzoin methyl ether, benzoin methyl ether, 4,4'-dimethoxybenzoin, 4,4'-dimethylbenzil, a benzophenone, benzophenone-3,3',4,4'-tetracarboxylic dianhydride, 4-benzobiphenyl, 4,4'-bis(diethylamino)benzophenone, 4,4'-bis[2-(1-propenyl)phenoxy]-benzophenone, 4-(diethylamino)benzophenone, 4,4'-dihydroxybenzophenone, 4-(dimethylamino)-benzophenone, 3,4-dimethylbenzophenone, 3-hydroxybenzophenone, 3-hydroxybenzophenone, 4-hydroxybenzophenone, 2-methylbenzophenone, 3-methylbenzophenone, 4-methylbenzophenone, methyl benzoylformate, Michler's ketone, a cationic initiator, an anionic initiator, bis(4-tert-butylphenyl)iodonium perfluoro-1-butanesulfonate, bis(4-tert-butylphenyl)iodonium p-toluenesulfonate, bis(4-tert-butylphenyl)-iodonium triflate, boc-methoxyphenyldiphenylsulfonium triflate, (4-tert-butylphenyl)diphenylsulfonium triflate, diphenyliodonium hexafluorophosphate, diphenyliodonium nitrate, diphenyliodonium p-toluene-sulfonate, diphenyliodonium triflate, (4-fluorophenyl)diphenylsulfonium triflate, N-hydroxynaphthalimide triflate, N-hydroxy-5-norbornene-2,3-dicarboximide perfluoro-1-butanesulfonate, (4-iodophenyl)-diphenylsulfonium triflate, (4-methoxyphenyl)

diphenylsulfonium triflate, 2-(4-methoxystyryl)-4,6-bis(trichloromethyl)-1,3,5-triazine, (4-methylthiophenyl) methyl phenyl sulfonium triflate, 1-naphthyl diphenylsulfonium triflate, (4-phenoxyphenyl)diphenylsulfonium triflate, (4-phenylthiophenyl)-diphenylsulfonium triflate, triarylsulfonium hexafluoroantimonate salt, triarylsulfonium hexafluorophosphate salt, triphenylsulfonium perfluoro-1-butanesulfonate, triphenylsulfonium triflate, tris(4-tetra-butylphenyl)-sulfonium perfluoro-1-butanesulfonate, tris(4-tert-butylphenyl)sulfonium triflate, anthraquinone-2-sulfonic acid sodium salt, 2-tert-butylanthraquinone, camphorquinone, diphenyl(2,4,6-trimethylbenzoyl)phosphine oxide, lithium phenyl-2,4,6-trimethylbenzoylphosphinate, 9,10-phenanthrenequinone, phenylbis(2,4,6-trimethylbenzoyl)phosphine oxide, a thioxanthone, 1-chloro-4-propoxy-9H-thioxanthen-9-one, 2-chloro-thioxanthen-9-one, 2,4-diethyl-9H-thioxanthen-9-one, isopropyl-9H-thioxanthen-9-one, 10-methyl-phenothiazine, thioxanthen-9-one, an Irgacure product, TPO-L, a derivative thereof, or a combination thereof.

In some embodiments, the photoinitiator initiates photopolymerization using light energy. In certain embodiments, the photoinitiator initiates photopolymerization with exposure to light energy from 800 nm to 250 nm, from 800 nm to 350 nm, from 800 nm to 450 nm, from 800 nm to 550 nm, from 800 nm to 650 nm, from 600 nm to 250 nm, from 600 nm to 350 nm, from 600 nm to 450 nm, or from 400 nm to 250 nm. In some embodiments, the photoinitiator initiates photopolymerization following absorption of two photons (either simultaneously or sequentially), which can use longer wavelengths of light to initiate the photopolymerization.

In some embodiments, the initiator is a thermal initiator. In some embodiments, the resin comprises more than one initiator (e.g., 2, 3, 4, 5, or more than 5 initiators).

In some embodiments, the resin comprises an azo compound. In some embodiments, the polymerization is initiated using an azo compound, e.g., 2,2'azobis(2-methylpropionitrile), 4,4'-azobis(4-cyanovaleric acid), 1,1'-azobis(cyclohexanecarbonitrile), azobisisobutyronitrile, benzophenone, an inorganic peroxide, ammonium persulfate, hydroxymethanesulfinic acid monosodium salt, potassium persulfate, sodium persulfate, an organic peroxide, tert-butyl hydroperoxide, tert-butyl peracetate, cumene hydroxy-peroxide, 2,5-di(tert-butyl)peroxy-2,5-dimethyl-3-hexyne, dicumyl peroxide, 2,5-bis(tert-butylperoxy)-2,5-dimethylhexane, 2,5-bis(tert-butylperoxy)-2,5-dimethylhexane, 2,4-pentanedione peroxide, 1,1-bis(tert-butylperoxide)-3,3,5-trimethylcyclohexane, 1,1-bis(tert-butylperoxy)cyclohexane, benzoyl peroxide, tert-butyl peroxide, tert-butyl peroxybenzoate, TBEC, tert-butyl hydroperoxide, a derivative thereof, or a combination thereof.

In some embodiments, a thermal cure temperature is used during polymerization. In certain embodiments, the thermal cure temperature can be from −50° C. to 500° C., from −10° C. to 300° C., from −5° C. to 200° C., from 0° C. to 100° C., from 10° C. to 90° C., or from 20° C. to 80° C. In certain embodiments the amount of time a material spends at a thermal cure temperature is controlled. In some embodiments the amount of time the material spends at the thermal cure temperature is between 1 minute and 2 weeks, between 1 minute and 1 week, between 1 minute and 6 days, between 1 minute and 5 days, between 1 minute and 4 days, between 1 minute and 3 days, between 1 minute and 2 days, between 1 minute and 24 hours, between 1 minute and 12 hours, between 1 minute and 6 hours, between 1 minute and 3 hours, between 1 minute and 2 hours, between 1 minute and 1 hour, between 5 minutes and 1 hour, between 10 minutes and 1 hour, between 15 minutes and 2 hours, or between 30 minutes and 2 hours.

In some embodiments, polymerization comprises using a source of radiation. In certain embodiments, polymerization is activated by exposure to a source of radiation (e.g., photopolymerization). In certain embodiments, the source of radiation comprises ultraviolet light, visible light, infrared light, microwave irradiation, laser exposure, holography, DLP projection, optical lithography, pulsed light, or a combination thereof. In some embodiments, polymerization comprises using more than one source of radiation (e.g., to separately process a first phase and a second phase of a resin).

In some embodiments, it is preferential that an initial intensity of exposure is low in order to favorably induce polymerization of one component (e.g., one monomer component). As a non-limiting example, in some embodiments it is preferential that a first exposure having a first specified wavelength has a relatively low intensity of exposure in order to favorably induce polymerization of a polymerizable component. In some embodiments, a first exposure of a specified wavelength of light is used to form a first polymer. In some embodiments, a first exposure of a specified wavelength of light is used to form a second polymer. In certain embodiments, the intensity (values are given in Watts/cm$^2$) of the first exposure is between 10 and 100, between 50 and 80, between 100 and 50, between 100 and 10, between 0.1 and 8, between 0.1 and 6, between 0.1 and 4, or between 0.1 Watts/cm$^2$ and 2 Watts/cm$^2$. In some embodiments, a second exposure of a specified wavelength of light is used to form a first polymer. In some embodiments, a second exposure of a specified wavelength of light is used to form a second polymer. In certain embodiments, the intensity (values are given in Watts/cm$^2$) of the second exposure is between 10 and 100, between 50 and 80, between 100 and 50, between 100 and 10, between 0.1 and 8, between 0.1 and 6, between 0.1 and 4, or between 0.1 Watts/cm$^2$ and 2 Watts/cm$^2$.

In some embodiments, it is preferential that a second exposure has high intensity of exposure in order to induce polymerization of remaining monomers that did not undergo polymerization in the first exposure. In some embodiments, the second exposure comprises a specified wavelength of light. In some embodiments, a second exposure is used to form a second polymer. In some embodiments, a second exposure is used to form a first polymer. In certain embodiments, the intensity (values are given in Watts/cm$^2$) of the second exposure is between 1 and 1000, between 5 and 500, between 5 and 100, or between 10 Watts/cm$^2$ and 100 Watts/cm$^2$. In some embodiments, the intensity of the first exposure is high intensity. In systems that use lasers as the light source, the light intensity may be greater than a 1 W/cm$^2$, especially when considering the spot size, but the dose delivered can be low enough so as not to burn the resin.

In certain embodiments, the polymerization reaction comprises step-growth polymerization, chain-growth polymerization, radical polymerization, living polymerization, cationic addition polymerization, anionic addition polymerization, emulsion polymerization, solution polymerization, precipitation polymerization, photopolymerization, or any combination thereof. In preferred embodiments, the polymerization reaction comprises photopolymerization.

In some embodiments, diffusion of all the components results in a higher concentration of the more reactive component (e.g., polymerizable monomer) in the reacting region (e.g., a first region comprising a first phase) upon spatial control of exposure of polymerization, and a higher concentration of the less reactive components in the unreactive region (e.g., a second region comprising a second phase). In some embodiments, the reactive region (the first region) is characterized by being exposed to a source of radiation during an initial exposure. In certain embodiments, the unreactive region (the second region) is not exposed to the source of radiation during an initial exposure.

In certain embodiments, diffusion of resin components takes place within the resin and/or forming polymer(s). In some embodiments, the first component (e.g., first polymerizable monomer) and the second component (e.g., second polymerizable monomer) diffuse through the first polymer during the polymerization of the first polymer. In some embodiments, as the first components are polymerized into the first polymer, diffusion of the first component slows. In certain embodiments, only the second component undergoes diffusion through the first polymer. In some embodiments, the diffusion creates regions having higher concentration of components. As described further herein, in some embodiments the polymerization reaction is regionally controlled (i.e., control of size, shape, and/or location of phase reactions), e.g., through use of a mask during photopolymerization. In certain embodiments, the polymerization is regionally controlled through use of control of temperature, size of polymers, solubility parameters, size of monomers, speed of cure, intensity of light, dose of light, presence and/or amount of catalyst, and any combination thereof.

For example, a region-specific polymerization reaction that polymerizes a first component but not a second component would produce the first polymer in the specific regions, while the second component diffused toward other regions. Accordingly, a region of the composite material (e.g., the first continuous phase) may comprise greater than 0.1% of a first component, greater than 5% of a first component, greater than 10% of a first component, greater than 20% of a first component, greater than 30% of a first component, greater than 40% of a first component, greater than 50% of a first component, greater than 60% of a first component, greater than 70% of a first component, greater than 80% of a first component, greater than 90% of a first component, or greater than 95% of a first component by weight. The first component may partially or fully undergo polymerization, and therefore a region of the composite material (e.g., the first continuous phase) may comprise greater than 50% of a first polymer, greater than 60% of a first polymer, greater than 70% of a first polymer, greater than 80% of a first polymer, greater than 90% of a first polymer, or greater than 95% of a first polymer by weight.

In some embodiments, the diffusion of a second component out of the first region results in a lowering of the amount of the second component in the first region. In some embodiments, a region of the composite material may comprise less than 100% of a second component, less than 95% of a second component, less than 90% of a second component, less than 80% of a second component, less than 70% of a second component, less than 60% of a second component, less than 50% of a second component, less than 40% of a second component, less than 30% of a second component, less than 20% of a second component, less than 10% of a second component, or less than 5% of a second component by weight. The unreactive region may be later polymerized. The second component may partially or fully undergo polymerization, and therefore a region of the composite material may comprise less than 50% of a second polymer, less than 40% of a second polymer, less than 30% of a second polymer, less than 20% of a second polymer, less than 10% of a second polymer, or less than 5% of a second polymer by weight.

In some embodiments, a composite material can undergo copolymerization in selective regions. In certain embodiments, a composite material undergoes copolymerization based on exposure to a source of radiation. In certain embodiments, diffusion of resin components takes place wherein the first component and the second component diffuse through the resin during the polymerization to form a copolymer comprising the first component and the second component. Accordingly, selective polymerization can provide regions comprising a copolymer, while regions that are not exposed to the source of radiation comprise less to no copolymer. In some embodiments, the diffusion creates regions having higher concentration of components or copolymer. For example, a region-specific polymerization reaction that polymerizes a first component and a second component would produce the copolymer in the specific regions, while other resin components diffused toward other regions. The first component and the second component may partially or fully undergo polymerization, and therefore a region of the composite material (e.g., the first continuous phase) may comprise greater than 50% of a first copolymer, greater than 60% of a first copolymer, greater than 70% of a first copolymer, greater than 80% of a first copolymer, greater than 90% of a first copolymer, or greater than 95% of a first copolymer by weight.

In some embodiments, polymerization of a region of the resin provides a change in the percentage of monomer presence, or a corresponding change in the presence of its corresponding polymer. In certain embodiments, such enrichment of polymerizable components or polymer can be provided using a source of radiation comprising a specified wavelength. In some embodiments, a higher percentage of one component is present in a region than what would be expected by bulk cure conditions. In preferred embodiments, the percentage change is greater than 10% (mole percentage) from initial resin values. In some embodiments, the percentage change is about 5% or greater than 5% from initial resin values. In certain embodiments, the percent change is greater than 20%, greater than 30%, greater than 40%, greater than 50%, greater than 60%, greater than 70%, greater than 80%, greater than 90%, greater than 95%, or greater than 98% (mole percentage) from initial resin values. As a non-limiting example, a resin comprising an initial amount of 60% Monomer A and 40% Monomer B is polymerized to provide a bulk copolymerized material having an average of a 60% Monomer A and 40% Monomer B in the bulk cured copolymer. In comparison, using the methods disclosed herein, a preferential polymerization of the same resin with a specified wavelength and/or specified temperature may produce a copolymer having an average composition of 50% Monomer A and 50% Monomer B, which would be a 17% decrease in the concentration of Monomer A in the region, while monomer B would experience a 25% increase in average regional copolymer composition. The percentage can be based on an initial and final molar percentage for monomer concentration in the starting monomer mix and for the monomer concentration incorporated into a copolymer for a defined region of space. In some embodiments, the concentration or composition of starting monomer mixtures and final polymer composition are described by weight percentages.

In some embodiments, a difference in reactivity comprises a difference in a polymerization rate coefficient, a difference in concentration, a difference in functionality (such as mono-functional, di-functional, tri-functional, etc.), a difference in solubility, a difference in diffusivity of the first component, a difference in diffusivity of the second component, a difference in polymerization activity at a specified temperature, a difference in polymerization activity when exposed to a specified wavelength of light, a difference of reactivity with a photoinitiator, or any combination thereof. In some embodiments, techniques can be used to change the composition of the first polymer in comparison to the composition of the second polymer. In certain embodiments, the composition of the first polymer is determined by differences in reactivity between the first component and the second component. In specific embodiments, a difference in reactivity comprises a difference in oxygen inhibition, a difference in light absorption, a difference in photoinitiator concentration, a difference in component concentration, temperature, component solubilities, polymer solubilities, or a combination thereof.

In some embodiments, a first continuous phase can have a first polymerization rate and a second continuous phase can have a second polymerization rate. In instances in which a first continuous phase polymerized via a radically-induced polymerization reaction and a second continuous phase polymerizes with a ionically-induced polymerization reaction, the radically-induced polymerization reaction rate can be higher than the ionically-induced polymerization reaction rate. In some cases, a first polymerization rate can be from about $1\times10^3$ $s^{-1}$ and not more than $1\times10^5$ $s^{-1}$, from about $2.5\times10^3$ $s^{-1}$ and not more than $5\times10^4$ $s^{-1}$, from about $2.5\times10^3$ $s^{-1}$ and not more than $7.5\times10^3$ $s^{-1}$, or from about $3.5\times10^3$ $s^{-1}$ and not more than $5\times10^3$ $s^{-1}$. In some cases, a second polymerization rate can be from about $1\times10^2$ $s^{-1}$ and not more than $1\times10^4$ $s^{-1}$, from about $2.5\times10^2$ $s^{-1}$ and not more than $7.5\times10^3$ $s^{-1}$, from about $1\times10^3$ $s^{-1}$ and not more than $5\times10^3$ $s^{-1}$, or from about $1.5\times10^3$ $s^{-1}$ and not more than $2.5\times10^3$ $s^{-1}$. In some embodiments, such first polymerization rate corresponds to a first continuous phase comprising an acrylate moiety, and such second polymerization rate corresponds to a second continuous phase comprising a methacrylate moiety. In some instances, a polymerization rate herein can be per mole of a monomer and thus be expressed in $M^{-1}$ $s^{-1}$.

In some embodiments, photopolymerization is used and regions are generated by a mask, a photomask, a laser path, a Digital Light Processor projector, Digital mirror devices, Liquid Crystal Displays, or cover protecting the unreactive region from a light source. In certain embodiments, the mask or cover comprises a pattern, thereby forming patterned regions of polymerization on the layer. In certain embodiments, the mask comprises a plurality of lines, a plurality of parallel lines, a plurality of brick shapes, a plurality of circular holes, a plurality of perpendicular lines forming a hatched pattern, or a combination thereof. In some embodiments, the mask comprises regions that allow unimpeded radiation, wherein the smallest axis of the region is from 5 nm to 100 microns in size, from 5 nm to 100 nm in size, from 5 nm to 200 nm in size, from 5 nm to 300 nm in size, from 5 nm to 400 nm in size, from 5 nm to 500 nm in size, from 10 nm to 200 nm in size, from 10 nm to 300 nm in size, from 10 nm to 400 nm in size, from 10 nm to 500 nm in size, from 10 nm to 1 micron in size, from 10 nm to 100 microns in size, from 20 nm to 100 microns in size, from 20 nm to 10 microns in size, from 20 nm to 1 micron in size, from 20 nm to 500 nm in size, from 20 nm to 300 nm in size, from 40 nm to 200 nm in size, from 40 nm to 300 nm in size, from 40 nm to 400 nm in size, from 40 nm to 500 nm in size, from 40 nm to 1 micron in size, from 40 nm to 100 microns in size, from 60 nm to 200 nm in size, from 60 nm to 300 nm in size, from 60 nm to 400 nm in size, from 60 nm to 500 nm in size, from 60 nm to 1 micron in size, from 60 nm to 100 microns in size, from 80 nm to 200 nm in size, from 80 nm to 300 nm in size, from 80 nm to 400 nm in size, from 80 nm to 500 nm in size, from 80 nm to 1 micron in size, from 80 nm to 100 microns in size, from 100 nm to 100 microns in size, from 100 nm to 10 microns in size, from 100 nm to 1 micron in size, from 100 nm to 500 nm in size, from 200 nm to 100 microns in size, from 200 nm to 50 microns in size, from 200 nm to 25 microns in size, from 200 nm to 5 microns in size, from 200 nm to 1 micron in size, from 500 nm to 100 microns in size, from 500 nm to 50 microns in size, from 500 nm to 25 microns in size, from 500 nm to 100 microns in size, from 500 nm to 5 microns in size, from 500 nm to 1 micron in size, from 1 micron to 100 microns in size, from 1 to 50 microns in size, from 1 to 40 microns in size, from 1 to 30 microns in size, from 1 to 20 microns in size, from 1 to 10 microns in size, from 2 to 100 microns in size, from 2 to 50 microns in size, from 2 to 25 microns in size, from 2 to 10 microns in size, from 4 to 100 microns in size, from 4 to 50 microns in size, from 4 to 40 microns in size, from 4 to 20 microns in size, form 4 to 10 microns in size, from 6 to 100 microns in size, from 6 to 50 microns in size, from 6 to 25 microns in size, from 6 to 20 microns in size, from 10 to 100 microns in size, or from 10 to 50 microns in size.

In certain embodiments, photopolymers are fabricated by "vat" processes in which light is used to selectively cure a section or portion of resin in a vat or reservoir. Each layer of the object being fabricated may be selectively exposed to light in a single exposure or by scanning a beam of light across the layer. Specific techniques include stereolithography (SLA), Digital Light Processing (DLP), holographic projection, and two photon-induced photopolymerization (TPIP).

In some embodiments, the resin is a liquid phase at a use temperature (e.g., a temperature of fabrication) and/or at an elevated temperature. Highly viscous resins may present challenges during the fabrication of objects (e.g., using 3D printing). In some embodiments, the resin is a liquid at a fabrication temperature. In some embodiments, the resin is a liquid at an elevated temperature. In certain embodiments, the fabrication temperature is the elevated temperature. In some embodiments, the elevated temperature is at or above the melting temperature ($T_m$) of the resin components (e.g., the first component and the second component). In certain embodiments, the elevated temperature is a temperature in the range from 40° C. to 100° C., from 60° C. to 100° C., from 80° C. to 100° C., from 40° C. to 150° C., or from 150° C. to 350° C. In some embodiments, the elevated temperature is a temperature above 40° C., above 60° C., above 80° C., or above 100° C. In some embodiments, the resin at the elevated temperature is a liquid with a viscosity less than 50 PaS, less than 20 PaS, less than 10 PaS, less than 5 PaS, or less than 1 PaS. In preferred embodiments, the resin at the elevated temperature is a liquid with a viscosity less than 20 PaS. In more preferred embodiments, the resin at the elevated temperature is a liquid with a viscosity less than 1 PaS.

In some embodiments, the resin has a viscosity less than 60 PaS, less than 50 PaS, less than 40 PaS, less than 30 PaS, less than 20 PaS, less than 10 PaS, less than 9 PaS, less than 8 PaS, less than 7 PaS, less than 6 PaS, less than 5 PaS, less than 4 PaS, less than 3 PaS, less than 2 PaS, less than 1 PaS, or less than 0.1 PaS at an elevated temperature. In some embodiments, the elevated temperature is a print temperature. In some embodiments, the elevated temperature is at, above, or below room temperature. In some embodiments, the elevated temperature is from 0° C. to 25° C., from 25° C. to 40° C., from 40° C. to 150° C., or from 10° C. to 40° C. In preferred embodiments, the resin has a viscosity from 0.05 PaS to 10 PaS at the print temperature (i.e., the fabricating temperature). In some embodiments, the resin has a viscosity from 1 PaS to 10 PaS at the print temperature. In some embodiments, the print temperature can include a temperature or temperatures from 20-120° C. The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2/s$. Devices for measuring viscosity include viscometers and rheometers. The viscosity of a composition described herein may be measured at 110° C. using a rheometer. For example, an MCR 301 rheometer from Anton Paar may be used for rheological measurement in rotation mode (PP-25, 50 s-1, 50-115° C., 3° C./min).

In certain embodiments, the resins disclosed herein can be used in 3D printing processes to form objects. The resins are capable of being 3D printed, and provide polymer materials having the beneficial properties disclosed further herein.

In some embodiments, the resin comprises a ratio of the first component (e.g., first polymerizable monomer) to the second component (e.g., second polymerizable monomer) (vol/vol) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the resin comprises a ratio of the first component (e.g., first polymerizable monomer) to the second component (e.g., second polymerizable monomer) (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the resin comprises a ratio of the first component (e.g., first polymerizable monomer) to the second component (e.g., second polymerizable monomer) (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, the resin comprises a ratio of the second component (e.g., second polymerizable monomer) to the first component (e.g., first polymerizable monomer) (vol/vol) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the resin comprises a ratio of the second component (e.g., second polymerizable monomer) to the first component (e.g., first polymerizable monomer) (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the resin comprises a ratio of the second component (e.g., second polymerizable monomer) to the first component (e.g., first polymerizable monomer) (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

Composite Materials

In some embodiments, polymer composites described herein have enhanced physical properties when compared with homopolymers of similar monomer species. For example, a composite material comprising a first polymer having high strength (e.g., high storage modulus) and a second polymer having high flexibility can form a composite with higher strength and flexibility than a homopolymer of either monomer species. Composite materials can provide two or more contrasting properties. For example, some embodiments of the composite materials disclosed herein have the contrasting properties of a high modulus low elasticity material to generate force to move teeth and also a low modulus high elasticity material to provide good mouth-feel for patient comfort and low breakage.

In some embodiments, the composite materials have enhanced properties relative to simple mixtures of the corresponding monomers of the resin that form homogenous mixtures. For example, composite materials herein can comprise increased modulus, increased elongation to break, increased stress to yield, increased heat deflection temperature, and decreased stress relaxation (e.g., less creep) in comparison to corresponding materials that do not have multiple continuous phases (e.g., are homogenous).

In some embodiments, the composite materials comprise a hard phase comprising an acrylate component (e.g., an acrylate polymerizable monomer polymerized to form a polymer) and a soft phase comprising a methacrylate component (e.g., a methacrylate polymerizable monomer polymerized to form a polymer). Advantageously, increased modulus is observed in embodiments applying an acrylate component in the formation of the hard phase and a methacrylate component in the formation of the soft phase when the composite material is compared to traditional materials (e.g., applying the methacrylate component in the hard phase and the acrylate component in the soft phase). Such improvement in modulus confers beneficial properties to composite materials and devices described herein.

In some embodiments, the present disclosure provides polymeric materials generated from the resins described further herein (also referred to herein as "polymeric materials" and "cured polymeric materials"). The cured polymeric materials comprise a first continuous phase (also referred to herein as a "first domain"), which is a phase of the polymeric material wherein the first component (e.g., first polymerizable monomer, incorporated into a first polymer) of the resins described herein is present, and a second continuous phase (also referred to herein as a "second domain"), which is a phase of the polymeric material wherein the second component (e.g., second polymerizable monomer, incorporated into a second polymer) is present. A continuous phase is a phase that can be traced or is connected from one side of a material to another side of the material; for instance, a closed-cell foam has material comprising the foam that can be traced across the sample, whereas the closed cells (bubbles) represent a discontinuous phase of air pockets. Discontinuous phases do not have a connected singular phase (e.g., have islands of material, such as a glass filler in a resin).

In some aspects, the present disclosure provides a composite material comprising a first continuous phase and a second continuous phase. In some embodiments, the first continuous phase comprises a first polymer region (e.g., a polymer region comprising a first polymer, such as the first polymer formed from the first component of the resin). In some embodiments, the first polymer region is a soft polymer region. In some embodiments, the second continuous phase comprises a second polymer region (e.g., a polymer region comprising a second polymer, such as the second polymer formed from the second component of the resin). In some embodiments, the second polymer region is a hard polymer region. A soft polymer region is a region comprising a polymer that has a hardness from about 60A to about 85D. Hence, in some instances, a soft polymer region can have a hardness from about 60A to about 70A, from about 70A to about 80A, from about 80A to about 90A, or from about 90A to about 100A. In other embodiments, a soft polymer region can have a hardness from about 60D to about 70D, from about 70D to about 80D, or from about 75D to about 85D. A hard polymer region is a region comprising a polymer that has a hardness from about 60A to about 85D. Hence, in some instances, a hard polymer region can have a hardness from about 60A to about 70A, from about 70A to about 80A, from about 80A to about 90A, or from about 90A to about 100A. In other embodiments, a hard polymer region can have a hardness from about 60D to about 70D, from about 70D to about 80D, or from about 75D to about 85D. A soft polymer region is a region comprising a polymer that can have a tensile modulus from about 1 MPa to about 600 MPa, from about 300 MPa to about 600 MPa, or from about 450 MPa to about 600 MPa. A hard polymer region is a region comprising a polymer that can have a tensile modulus from about 600 MPa to about 5000 MPa, from about 700 MPa to about 2000 MPa, or from about 800 MPa to about 1500 MPa.

The soft polymer region (e.g., first continuous phase formed from the first component of the resin) is softer than the hard polymer region (e.g., second continuous phase formed from the second component of the resin). In some embodiments, the hard polymer region is harder than the soft polymer region. In certain embodiments, the hard polymer region (e.g., second continuous phase) is 1.1-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, or more than 100-fold harder than the soft polymer region (e.g., first continuous phase). In some embodiments, the composite material comprises a ratio of the hardness of the hard polymer region (e.g., second continuous phase) to the hardness of the soft polymer region (e.g., first continuous phase) of greater than or equal to 1:1, greater than or equal to 1.1:1, greater than or equal to 1.2:1, greater than or equal to 1.3:1, greater than or equal to 1.4:1, greater than or equal to 1.5:1, greater than or equal to 1.6:1, greater than or equal to 1.7:1, greater than or equal to 1.8:1, greater than or equal to 1.9:1, greater than or equal to 2:1, greater than or equal to 3:1, greater than or equal to 4:1, greater than or equal to 5:1, greater than or equal to 6:1, greater than or equal to 7:1, greater than or equal to 8:1, greater than or equal to 9:1, greater than or equal to 10:1, greater than or equal to 20:1, greater than or equal to 30:1, greater than or equal to 40:1, greater than or equal to 50:1, or greater than or equal to 100:1. In some embodiments, a composite material herein comprises a hard polymer region having a first flexural modulus and a soft polymer region having a second flexural modulus, wherein the ratio between the first flexural modulus and the second flexural modulus can be greater than or equal to 1:1, greater than or equal to 1.1:1, greater than or equal to 1.2:1, greater than or equal to 1.3:1, greater than or equal to 1.4:1, greater than or equal to 1.5:1, greater than or equal to 1.6:1, greater than or equal to 1.7:1, greater than or equal to 1.8:1, greater than or equal to 1.9:1, greater than or equal to 2:1, greater than or equal to 3:1, greater than or equal to 4:1, greater than or equal to 5:1, greater than or equal to 6:1, greater than or equal to 7:1, greater than or equal to 8:1, greater than or equal to 9:1, greater than or equal to 10:1, greater than or equal to 20:1, greater than or equal to 30:1, greater than or equal to 40:1, greater than or equal to 50:1, or greater than or equal to 100:1.

In certain embodiments, the first continuous phase comprises a vertical dimension less than 100 nm. In some embodiments, the first continuous phase comprises a lateral dimension less than 100 nm. In some embodiments, the second continuous phase comprises a vertical dimension less than 100 nm. In some embodiments, the second continuous phase comprises a lateral dimension less than 100 nm. In some embodiments, the lateral and/or vertical dimension of the first and/or second phase is from 5 nm to 100 microns in size, from 5 nm to 100 nm in size, from 5 nm to 200 nm in size, from 5 nm to 300 nm in size, from 5 nm to 400 nm in size, from 5 nm to 500 nm in size, from 10 nm to 200 nm in size, from 10 nm to 300 nm in size, from 10 nm to 400 nm in size, from 10 nm to 500 nm in size, from 10 nm to 1 micron in size, from 10 nm to 100 microns in size, from 20 nm to 100 microns in size, from 20 nm to 10 microns in size, from 20 nm to 1 micron in size, from 20 nm to 500 nm in size, from 20 nm to 300 nm in size, from 40 nm to 200 nm in size, from 40 nm to 300 nm in size, from 40 nm to 400 nm in size, from 40 nm to 500 nm in size, from 40 nm to 1 micron in size, from 40 nm to 100 microns in size, from 60 nm to 200 nm in size, from 60 nm to 300 nm in size, from 60 nm to 400 nm in size, from 60 nm to 500 nm in size, from 60 nm to 1 micron in size, from 60 nm to 100 microns in size, from 80 nm to 200 nm in size, from 80 nm to 300 nm in size, from 80 nm to 400 nm in size, from 80 nm to 500 nm in size, from 80 nm to 1 micron in size, from 80 nm to 100 microns in size, from 100 nm to 100 microns in size, from 100 nm to 10 microns in size, from 100 nm to 1 micron in size, from 100 nm to 500 nm in size, from 200 nm to 100 microns in size, from 200 nm to 50 microns in size, from 200 nm to 25 microns in size, from 200 nm to 5 microns in size, from 200 nm to 1 micron in size, from 500 nm to 100 microns in size, from 500 nm to 50 microns in size, from 500 nm to 25 microns in size, from 500 nm to 100 microns in size, from 500 nm to 5 microns in size, from 500 nm to 1 micron in size, from 1 micron to 100 microns in size, from 1 to 50 microns in size, from 1 to 40 microns in size, from 1 to 30 microns in size, from 1 to 20 microns in size, from 1 to 10 microns in size, from 2 to 100 microns in size, from 2 to 50 microns in size, from 2 to 25 microns in size, from 2 to 10 microns in size, from 4 to 100 microns in size, from 4 to 50 microns in size, from 4 to 40 microns in size, from 4 to 20 microns in size, form 4 to 10 microns in size, from 6 to 100 microns in size, from 6 to 50 microns in size, from 6 to 25 microns in size, from 6 to 20 microns in size, from 10 to 100 microns in size, or from 10 to 50 microns in size.

In certain embodiments, the composite material comprises a first continuous phase comprising a soft polymer region and a second continuous phase comprising a hard polymer region, wherein the composite material comprises a gradient between the first continuous phase and the second continuous phase. In some embodiments, the first continuous phase corresponds with the polymer formed during the polymerization of the first component of the resin and the second continuous phase corresponds with the polymer formed during the polymerization of the second component of the resin. A gradient between a first continuous phase and a second continuous phase is a region wherein a border between the first continuous phase and the second continuous phase is not delineated. As a non-limiting example, a composite material comprising a first phase and a second phase wherein the phases are formed with control of exposure (e.g., by using a patterned mask) has delineated borders between the phases (e.g., regions initially exposed and regions not initially exposed). In contrast, in some embodiments described herein, such delineated borders between phases are not present.

In some embodiments, the composite materials described herein have continuous phases that form in a more randomized fashion in comparison to masked exposure, such that a gradient between phases is present. In some embodiments, the shape and/or size and/or location of at least one of the continuous phases is not controlled, thereby facilitating the formation of the gradient. In some embodiments, the shape and/or size and/or location of the first continuous phase is not controlled. In some embodiments, the shape and/or size and/or location of the second continuous phase is not controlled. In some embodiments, the gradient and/or the presence of the continuous phases is determined by Atomic Force Microscopy (AFM). As phase demand decreases, Atomic Force Microscopy can identify the presence of the first continuous phase and the second continuous phase in the composite materials described herein. In some embodiments, the AFM uses tapping mode. In some embodiments, Scanning Electron Microscopy (SEC) is used in place of AFM. In certain embodiments, wherein phase demand is larger, Differential Scanning Calorimetry (DSC) and/or Dynamic Mechanical Analysis (DMA) can observe the gradient and/or the continuous phases.

In some embodiments, factors such as temperature, size of polymers, solubility parameters, speed of cure, intensity of light, presence and/or amount of catalyst, or a combination thereof, can influence the presence and degree of gradient formation between continuous phases.

The polymeric material can be formed by curing the resins disclosed further herein. In some embodiments, the curing comprises a single curing step. In some embodiments, the curing comprises a plurality of curing steps. In preferred embodiments, the curing comprises at least one curing step exposing the resin to light. Exposing the resin to light can initiate and/or facilitate polymerization (e.g., photopolymerization) of at least one of the first or second components, especially with the presence of a photoinitiator in the resin. In some embodiments, the resin is exposed to UV (ultraviolet) light, visible light, IR (infrared) light, or any combination thereof. In some embodiments, the cured polymeric material is formed from the resin using at least one step comprising exposure to a light source, wherein the light source comprises UV light, visible light, and/or IR light. In some embodiments, the light source comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm. In some embodiments, the cured polymeric material is formed from the resin using at least a second exposure to a light source, wherein the light source comprises UV light, visible light, and/or IR light. In some embodiments, the second exposure comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm.

Discussion herein relating to the properties of the polymeric material refers to the material ready for use (e.g., a cured and cooled material to be used for its intended use, such as a cured and cooled aligner intended to provide a treatment to a patient).

In some embodiments, the polymeric material comprises a ratio of the first continuous phase (e.g., comprising the first component incorporated into a first polymer) to the second continuous phase (e.g., comprising the second component incorporated into a second polymer) (wt/wt) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the polymeric material comprises a ratio of the first continuous phase (e.g., comprising the first component incorporated into a first polymer) to the second continuous phase (e.g., comprising the second component incorporated into a second polymer) (wt/wt) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of the first continuous phase (e.g., comprising the first component incorporated into a first polymer) to the second continuous phase (e.g., comprising the second component incorporated into a second polymer) (wt/wt) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, the polymeric material comprises a ratio of the second continuous phase (e.g., comprising the second component incorporated into a second polymer) to the first continuous phase (e.g., comprising the first component incorporated into a first polymer) (wt/wt) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the polymeric material comprises a ratio of the second continuous phase (e.g., comprising the second component incorporated into a second polymer) to the first continuous phase (e.g., comprising the first component incorporated into a first polymer) (wt/wt) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of the second continuous phase (e.g., comprising the second component incorporated into a second polymer) to the first continuous phase (e.g., comprising the first component incorporated into a first polymer) (wt/wt) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, the polymeric material comprises a ratio of the first continuous phase (e.g., comprising the first component incorporated into a first polymer) to the second continuous phase (e.g., comprising the second component incorporated into a second polymer) (vol/vol) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the polymeric material comprises a ratio of the first continuous phase (e.g., comprising the first component incorporated into a first polymer) to the second continuous phase (e.g., comprising the second component incorporated into a second polymer) (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of the first continuous phase (e.g., comprising the first component incorporated into a first polymer) to the second continuous phase (e.g., comprising the second component incorporated into a second polymer) (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, the polymeric material comprises a ratio of the second continuous phase (e.g., comprising the second component incorporated into a second polymer) to the first continuous phase (e.g., comprising the first component incorporated into a first polymer) (vol/vol) of greater than 1:10, greater than 1:9, greater than 1:8, greater than 1:7, greater than 1:6, greater than 1:5, greater than 1:4, greater than 1:3, greater than 1:2, greater than 1:1, greater than 2:1, greater than 3:1, greater than 4:1, greater than 5:1, greater than 6:1, greater than 7:1, greater than 8:1, greater than 9:1, greater than 10:1, greater than 20:1, greater than 30:1, greater than 40:1, greater than 50:1, or greater than 99:1. In some embodiments, the polymeric material comprises a ratio of the second continuous phase (e.g., comprising the second component incorporated into a second polymer) to the first continuous phase (e.g., comprising the first component incorporated into a first polymer) (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of the second continuous phase (e.g., comprising the second component incorporated into a second polymer) to the first continuous phase (e.g., comprising the first component incorporated into a first polymer) (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, the polymeric material is biocompatible. Biocompatible can refer to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a human or other animal is exposed to or in contact with the biocompatible material. Alternatively, immune response may be determined histologically, wherein localized immune response is assessed by visually assessing markers, including immune cells or markers that are involved in the immune response pathway, in and adjacent to the material. In an aspect, a biocompatible material or device does not observably change immune response as determined histologically. In some embodiments, the disclosure provides biocompatible devices configured for long-term use, such as on the order of weeks to months, without invoking an adverse immune response. Biological effects may be initially evaluated by measurement of cytotoxicity, sensitization, irritation and intracutaneous reactivity, acute systemic toxicity, pyrogenicity, subacute/subchronic toxicity and/or implantation. Biological tests for supplemental evaluation include testing for chronic toxicity. In some embodiments, the polymeric material is bioinert. Bioinert refers to a material that does not elicit an immune response from a human or animal when it is disposed within an in-vivo biological environment. For example, a biological marker indicative of an immune response remains substantially constant (plus or minus 5% of a baseline value) when a human or animal is exposed to or in contact with the bioinert material. In some embodiments, the disclosure provides bioinert devices.

Evaluation of Polymeric Materials

In certain embodiments, the present disclosure provides polymeric materials formed from the resins described herein using the methods and/or systems described herein. Polymeric materials disclosed herein have properties that are favorable for numerous applications and for the production of various devices. As a non-limiting example, the polymeric materials described herein are useful for production of orthodontic appliances, such as aligners. Orthodontic appliances require toughness and resilience to move a patient's teeth, while maintaining durability for use. In some embodiments, the polymeric material has a high glass transition temperature, a low creep, and a low stress relaxation.

In some embodiments described herein, the polymeric materials have properties that are measured following placement of the material in an aqueous environment for 24 hours at 37° C. Property values of the polymeric material can be determined, for example, by using the following methods: stress relaxation properties can be assessed using an RSA-G2 instrument from TA Instruments, with a 3-point bending, according to ASTM D790; stress relaxation can be measured at 30° C. and submerged in water, and reported as the remaining load after 24 hours, or as the percent (%) of initial load; storage modulus can be measured at 37° C. and is reported in MPa; $T_g$ of the cured polymeric material can be assessed using dynamic mechanical analysis (DMA) and is provided herein as the tan δ peak when run at 1 hz with a temperature ramp of 2° C. a minute; tensile modulus, tensile strength, elongation at yield and elongation at break can be assessed according to ISO 527-2 5B; tensile strength at yield, elongation at break, tensile strength, and Young's modulus can be assessed according to ASTM D1708; and flexural stress relaxation remaining after 24 hours in wet environment at 37° C. ("flexural stress remaining") can be assessed according to ASTM E328. In some embodiments, the sample measurements are taken using a 1 mm thick sample. Other methods can be used to characterize the materials described herein, and the above methods provide exemplary methods.

As described further herein, in some embodiments polymeric materials formed using the methods and systems described herein are multiphase materials, comprising at least a first continuous phase and a second continuous phase (e.g., formed correspondingly from the first component generating the first polymer and the second component forming the second polymer). In some embodiments, such materials have more than one continuous phase, each with determinable characteristics that differ from each other. In such embodiments, the polymeric material can have more than one (e.g., 2, 3, 4, 5, or more) of the below-described polymeric material characteristics. For example, in some embodiments, a polymeric material having 2 continuous phases is a material wherein the first phase is characterized by a first tensile stress-strain curve, the second phase is characterized by a second tensile stress-strain curve, and the aggregate material (i.e., the polymer material as a combination of the phases) is characterized by a third tensile stress-strain curve. In some embodiments, the first, second, and third stress-strain curves are not identical. As described further herein, in some embodiments, the material properties of the cured polymeric material refers to the material properties of the aggregate material of multiple phases (e.g., the combination of all phases of the cured material) and the properties are determined and as described below. In some embodiments, the material properties of the cured polymeric material refer to properties of individual phases of the cured material (e.g., the first continuous phase and/or the second continuous phase) and the properties are determined and as described herein.

In some embodiments, the physical properties of a region (e.g., continuous phase) of a polymeric material are determined by forming comparable materials comprising or consisting of the phases and determining the physical properties therefrom. As a non-limiting example, a resin photopolymerized having multiple continuous regions can be formed and the material properties of the aggregate (i.e., the polymeric material comprising all phases) can be determined directly from the formed material, while samples of polymeric material formed solely comprising the first phase or the second phase can be used to determine the properties of each corresponding phase. In some embodiments, the properties of the polymeric material and the properties of at least one or at least two of the regions of the polymeric material can be determined directly from the polymeric material (e.g., can be directly measured without forming individual samples representing each region).

In some embodiments, the cured polymeric material (e.g., any one of the first continuous phase, the second continuous phase, and the aggregate polymeric material of all phases) is characterized by a tensile stress-strain curve that displays a yield point after which the test specimen continues to elongate, but there is no increase in load. Such yield point behavior can occur "near" the glass transition temperature, where the material is between the glassy and rubbery regimes and may be characterized as having viscoelastic behavior. In embodiments, viscoelastic behavior is observed in the temperature range 20° C. to 40° C. The yield stress is determined at the yield point. In some embodiments, the yield point follows an elastic region in which the slope of the stress-strain curve is constant or nearly constant. In embodiments, the modulus is determined from the initial slope of the stress-strain curve or as the secant modulus at 1% strain (e.g., when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by $\ln(l/l_0)$, which may be approximated by $(l-l_0)/l_0$ at small strains (e.g., less than approximately 10%) and the elongation is $l/l_0$, where l is the gauge length after some deformation has occurred and $l_0$ is the initial gauge length. The mechanical properties can depend on the temperature at which they are measured. The test temperature may be below the expected use temperature for a dental appliance such as 35° C. to 40° C. In some embodiments, the test temperature is 23±2° C.

In some embodiments, the cured polymeric material (e.g., any one of the first continuous phase, the second continuous phase, and the aggregate polymeric material of all phases) has a hardness from 60 Shore A to 85 Shore D. In certain embodiments, the cured polymeric material has a hardness from 60-70 Shore A, from 70-80 Shore A, from 80-90 Shore A, from 90-100 Shore A, from 0-10 Shore D, from 10-20 Shore D, from 20-30 Shore D, from 30-40 Shore D, from 40-50 Shore D, from 50-60 Shore D, from 60-70 Shore D, from 70-80 Shore D, or from 80-85 Shore D. In certain embodiments, the first continuous phase has a hardness from 60-70 Shore A, from 70-80 Shore A, from 80-90 Shore A, from 90-100 Shore A, from 0-10 Shore D, from 10-20 Shore D, from 20-30 Shore D, from 30-40 Shore D, from 40-50 Shore D, from 50-60 Shore D, from 60-70 Shore D, from 70-80 Shore D, or from 80-85 Shore D. In certain embodiments, the second continuous phase has a hardness from 60-70 Shore A, from 70-80 Shore A, from 80-90 Shore A, from 90-100 Shore A, from 0-10 Shore D, from 10-20 Shore D, from 20-30 Shore D, from 30-40 Shore D, from 40-50 Shore D, from 50-60 Shore D, from 60-70 Shore D, from 70-80 Shore D, or from 80-85 Shore D.

In some embodiments, the polymeric materials, a first region of the polymeric materials (e.g., the first continuous region), and/or a second region of the polymeric materials (e.g., the second continuous region) are characterized by one or more of: an elongation at break greater than or equal to 5%; a storage modulus greater than or equal to 500 MPa; a tensile modulus greater than or equal to 500 MPa; a stress remaining greater than or equal to 0.01 MPa; and a flexural modulus greater than or equal to 60 MPa after 24 hours soaking in water at ambient temperature (e.g., at 37° C.). In some embodiments, the polymeric materials, a first region of the polymeric materials, and/or a second region of the polymeric materials are characterized by an elongation at break greater than or equal to 5%. In some embodiments, the polymeric materials, a first region of the polymeric materials, and/or a second region of the polymeric materials are characterized by a storage modulus greater than or equal to 500 MPa. In some embodiments, the polymeric materials, a first region of the polymeric materials, and/or a second region of the polymeric materials are characterized by a tensile modulus greater than or equal to 500 MPa. In some embodiments, the polymeric materials, a first region of the polymeric materials, and/or a second region of the polymeric materials are characterized by a stress remaining greater than or equal to 0.01 MPa. In some embodiments, the polymeric materials, a first region of the polymeric materials, and/or a second region of the polymeric materials are characterized by a flexural modulus greater than or equal to 60 MPa after 24 hours soaking in water at ambient temperature (e.g., at 37° C.). In some embodiments, the polymeric materials, a first region of the polymeric materials, and/or a second region of the polymeric materials are characterized by two or more of: an elongation at break greater than or equal to 5%; a storage modulus greater than or equal to 500 MPa; a tensile modulus greater than or equal to 500 MPa; a stress remaining greater than or equal to 0.01 MPa; and a flexural modulus greater than or equal to 60 MPa after 24 hours soaking in water at ambient temperature (e.g., at 37° C.). In some embodiments, the polymeric materials, a first region of the polymeric materials, and/or a second region of the polymeric materials are characterized by: an elongation at break greater than or equal to 5%; a storage modulus greater than or equal to 500 MPa; a tensile modulus greater than or equal to 500 MPa; a stress remaining greater than or equal to 0.01 MPa; and a flexural modulus greater than or equal to 60 MPa after 24 hours soaking in water at ambient temperature (e.g., at 37° C.).

In some embodiments, the polymeric materials, a first region of the polymeric materials, and/or a second region of the polymeric materials are characterized by one or more of: a tensile modulus greater than or equal to 100 MPa after being placed in an aqueous environment for 24 hours at 37° C.; a tensile strength at yield greater than or equal to 5 MPa after being placed in an aqueous environment for 24 hours at 37° C.; a storage modulus greater than or equal to 500 MPa after being placed in an aqueous environment for 24 hours at 37° C.; a flexural stress remaining ("stress remaining") of greater than or equal to 1.5 MPa remaining after 24 hours after being placed in an aqueous environment for 24 hours at 37° C.; a hardness from 60 Shore A to 85 Shore D after being placed in an aqueous environment for 24 hours at 37° C.; and an elongation at break greater than or equal to 15% before and/or after being placed in an aqueous environment for 24 hours at 37° C. In some embodiments, the polymeric materials, a first region of the polymeric materials, and/or a second region of the polymeric materials are characterized by a tensile modulus greater than or equal to 100 MPa after being placed in an aqueous environment for 24 hours at 37° C. In some embodiments, the polymeric materials, a first region of the polymeric materials, and/or a second region of the polymeric materials are characterized by a tensile strength at yield greater than or equal to 5 MPa after being placed in an aqueous environment for 24 hours at 37° C. In some embodiments, the polymeric materials, a first region of the polymeric materials, and/or a second region of the polymeric materials are characterized by a storage modulus greater than or equal to 500 MPa after being placed in an aqueous environment for 24 hours at 37° C. In some embodiments, the polymeric materials, a first region of the polymeric materials, and/or a second region of the polymeric materials are characterized by a flexural stress remaining ("stress remaining") of greater than or equal to 1.5 MPa remaining after 24 hours after being placed in an aqueous environment for 24 hours at 37° C. In some embodiments, the polymeric materials, a first region of the polymeric materials, and/or a second region of the polymeric materials are characterized by a hardness from 60 Shore A to 85 Shore D after being placed in an aqueous environment for 24 hours at 37° C. In some embodiments, the polymeric materials, a first region of the polymeric materials, and/or a second region of the polymeric materials are characterized by an elongation at break greater than or equal to 15% before and/or after being placed in an aqueous environment for 24 hours at 37° C. In some embodiments, the polymeric materials, a first region of the polymeric materials, and/or a second region of the polymeric materials are characterized by: a tensile modulus greater than or equal to 100 MPa after being placed in an aqueous environment for 24 hours at 37° C.; a tensile strength at yield greater than or equal to 5 MPa after being placed in an aqueous environment for 24 hours at 37° C.; a storage modulus greater than or equal to 500 MPa after being placed in an aqueous environment for 24 hours at 37° C.; a flexural stress remaining ("stress remaining") of greater than or equal to 1.5 MPa remaining after 24 hours after being placed in an aqueous environment for 24 hours at 37° C.; a hardness from 60 Shore A to 85 Shore D after being placed in an aqueous environment for 24 hours at 37° C.; and an elongation at break greater than or equal to 15% before and/or after being placed in an aqueous environment for 24 hours at 37° C.

In some embodiments, the polymeric material, a first region of the polymeric material, and/or a second region of the polymeric material is characterized by a tensile modulus after 24 hours testing in a wet environment at 37° C. from 100 MPa to 3000 MPa, from 100 MPa to 2500 MPa, from 100 MPa to 2000 MPa, from 500 MPa to 3000 MPa, from 500 MPa to 2500 MPa, from 500 MPa to 2000 MPa, from 750 MPa to 3000 MPa, from 750 MPa to 2500 MPa, from 750 MPa to 2000 MPa, or from 800 MPa to 2000 MPa. In some embodiments, the polymeric material, a first region of the polymeric material, and/or a second region of the polymeric material has a tensile modulus of greater than or equal to 500 MPa after 24 hours in a wet environment at 37° C. In some embodiments, the polymeric material, a first region of the polymeric material, and/or a second region of the polymeric material is characterized by a tensile modulus greater than or equal to 800 MPa after 24 hours in a wet environment at 37° C. In some embodiments, tensile modulus is assessed according to ISO-527-2 5B.

In some embodiments, the polymeric material, a first region of the polymeric material, and/or a second region of the polymeric material has a tensile strength at yield from 1 MPa to 100 MPa, from 5 MPa to 85 MPa, from 10 MPa to 75 MPa, from 15 MPa to 65 MPa, from 20 MPa to 55 MPa, or from 25 MPa to 45 MPa. In some embodiments, the polymeric material, a first region of the polymeric material, and/or a second region of the polymeric material has a tensile strength at yield from 30 MPa to 60 MPa. In some embodiments, the polymeric material, a first region of the polymeric material, and/or a second region of the polymeric material is characterized by a tensile strength at yield greater than or equal to 0.1 MPa, greater than or equal to 0.5 MPa, greater than or equal to 1 MPa, greater than or equal to 10 MPa, greater than or equal to 30 MPa, greater than or equal to 40 MPa, greater than or equal to 50 MPa, greater than or equal to 60 MPa, greater than or equal to 70 MPa, greater than or equal to 80 MPa, greater than or equal to 90 MPa, or greater than or equal to 100 MPa. In some embodiments, the polymeric material, a first region of the polymeric material, and/or a second region of the polymeric material is characterized by a tensile strength at yield greater than or equal 30 MPa. In some embodiments, tensile strength is assessed according to ISO-527-2 5B.

In some embodiments, the polymeric material, a first region of the polymeric material, and/or a second region of the polymeric material is characterized by a storage modulus from 0.1 MPa to 4000 MPa, from 50 MPa to 2750 MPa, from 100 MPa to 2500 MPa, from 200 MPa to 2250 MPa, from 300 MPa to 3000 MPa, from 500 MPa to 3000 MPa, from 750 MPa to 3000 MPa, or from 1000 MPa to 3000 MPa after 24 hours in a wet environment at 37° C. In some embodiments, the polymeric material, a first region of the polymeric material, and/or a second region of the polymeric material is characterized by a storage modulus after 24 hours testing in a wet environment at 37° C. of 0.1 MPa to 4000 MPa, a storage modulus of 300 MPa to 3000 MPa, or a storage modulus of 750 MPa to 3000 MPa. In some embodiments, the polymeric material, a first region of the polymeric material, and/or a second region of the polymeric material is characterized by a storage modulus greater than or equal to 300 MPa, greater than or equal than 400 MPa, greater than or equal than 500 MPa, greater than or equal to 600 MPa, greater than or equal to 700 MPa, greater than or equal to 800 MPa, greater than or equal to 900 MPa, or greater than or equal to 1000 MPa. In some embodiments, storage modulus is assessed according to ASTM D790, DMA, or both. In some instances, storage modulus is assessed according to ASTM D790. In other instances, storage modulus is assessed according to DMA. In other embodiments, storage modulus is assessed according to ASTM D7028.

It may be advantageous for polymeric materials, a first region of the polymeric materials, and/or a second region of the polymeric materials to have a flexural stress remaining of 5% or greater after 24 hours testing in a wet environment at 37° C. In some embodiments, the flexural stress remaining is 5% or greater, 10% or greater, 15% or greater, 20% or greater, 25% or greater, 30% or greater, 35% or greater, 40% or greater, 50% or greater, 60% or greater, or 70% or greater. In some embodiments, the polymeric material, a first region of the polymeric material, and/or a second region of the polymeric material is characterized by a flexural stress remaining greater than 10% at 24 hours testing in a wet environment at 37° C. In some embodiments, the polymeric material, a first region of the polymeric material, and/or a second region of the polymeric material is characterized by a flexural stress remaining greater than 20% at 24 hours testing in a wet environment at 37° C. In some embodiments, the polymeric material, a first region of the polymeric material, and/or a second region of the polymeric material is characterized by a flexural stress remaining greater than 25% at 24 hours testing in a wet environment at 37° C. In some embodiments, the polymeric material, a first region of the polymeric material, and/or a second region of the polymeric material is characterized by a flexural stress remaining from 5% to 50%, from 10% to 50%, from 15% to 50%, from 20% to 50%, from 25% to 50%, or from 30% to 50% of the initial load after 24 hours in a wet environment at 37° C. In some embodiments, the polymeric material, a first region of the polymeric material, and/or a second region of the polymeric material is characterized by a flexural stress remaining from 5% to 100%, from 10% to 100%, from 15% to 100%, from 20% to 100%, from 25% to 100%, from 30% to 100%, from 40% to 100%, from 50% to 100%, from 60% to 100%, from 70% to 100%, from 80% to 100%, or from 90% to 100% of the initial load after 24 hours in a wet environment at 37° C. In some embodiments, the polymeric material, a first region of the polymeric material, and/or a second region of the polymeric material is characterized by a flexural stress remaining from 20% to 45% of the initial load after 24 hours in a wet environment at 37° C. In some embodiments, the polymeric material, a first region of the polymeric material, and/or a second region of the polymeric material is characterized by a flexural stress remaining greater than 50% of the initial load after 24 hours in a wet environment at 37° C. In some embodiments the flexural stress remaining is measured using a sample that is 1 mm thick. In some embodiments, flexural stress remaining is assessed according to ASTM E328.

In some embodiments, the polymeric material, a first region of the polymeric material, and/or a second region of the polymeric material is characterized by a flexural stress remaining from 0.01 MPa to 15 MPa, from 0.05 MPa to 15 MPa, from 0.1 MPa to 15 MPa, from 0.5 MPa to 15 MPa, from 1 MPa to 15 MPa, from 2 MPa to 15 MPa, from 3 MPa to 15 MPa, from 4 MPa to 15 MPa, from 5 MPa to 15 MPa, or from 10 MPa to 15 MPa after 24 hours in a wet environment at 37° C. In some embodiments, the polymeric material, a first region of the polymeric material, and/or a second region of the polymeric material is characterized by a flexural stress remaining from 2 MPa to 15 MPa after 24 hours in a wet environment at 37° C. In some embodiments, the polymeric material, a first region of the polymeric material, and/or a second region of the polymeric material is characterized by a flexural stress of greater than or equal to 0.1 MPa, greater than or equal to 0.5 MPa, greater than or equal to 1 MPa, greater than or equal to 1.5 MPa, greater than or equal to 2 MPa, greater than or equal to 2.5 MPa, greater than or equal to 3 MPa, greater than or equal to 4 MPa, greater than or equal to 5 MPa, greater than or equal to 6 MPa, greater than or equal to 7 MPa, greater than or equal to 8 MPa, greater than or equal to 9 MPa, greater than or equal to 10 MPa, or greater than or equal to 15 MPa remaining after 24 hours in a wet environment at 37° C. In some embodiments, the polymeric material, a first region of the polymeric material, and/or a second region of the polymeric material is characterized by a flexural stress of greater than or equal to 1.5 MPa remaining after 24 hours in a wet environment at 37° C. In some embodiments, flexural stress is assessed according to ASTM E328.

In some embodiments, the polymeric material, a first region of the polymeric material, and/or a second region of the polymeric material has a stress relaxation measurement determined by ASTM D790 with 5% deflection on a 3-point bending test. In some embodiments, the stress relaxation can be measured by monitoring the time-dependent stress resulting from a steady strain. The extent of stress relaxation can also depend on the temperature, relative humidity, and other applicable conditions (e.g., presence of water). In embodiments, the test conditions for stress relaxation are a temperature is 37±2° C. at 100% relative humidity or a temperature of 37±2° C. in water. Stress relaxation properties may be assessed using an RSA-G2 instrument from TA Instruments, with a 3-point bending, 5% strain method. The stress relaxation is typically measured at 37° C. and 100% relative humidity and reported as the remaining load after 24 hours, as either the percent (%) of initial load or in MPa). In some embodiments, the polymeric material, a first region of the polymeric material, and/or a second region of the polymeric material has a stress remaining of greater than or equal to 5% of the initial load. In some embodiments, the polymeric material, a first region of the polymeric material, and/or a second region of the polymeric material is characterized by a stress remaining of 5% to 45% of the initial load. In certain aspects, the polymeric material, a first region of the polymeric material, and/or a second region of the polymeric material is characterized by a stress remaining of 20% to 45% of the initial load. In certain embodiments, the polymeric material, a first region of the polymeric material, and/or a second region of the polymeric material is characterized by a stress remaining of greater than or equal to 20% or greater than or equal to 35% of the initial load. In some embodiments, the stress relaxation measurement of the polymeric material has a value at 24 hours in 30° C. water that is greater than 10% of the initial stress. In some embodiments, the stress relaxation measurement of the polymeric material, a first region of the polymeric material, and/or a second region of the polymeric material has a value at 24 hours in 30° C. water that is greater than 15%, greater than 20%, greater than 25%, greater than 30%, greater than 35%, greater than 40%, greater than 45%, or greater than 50% of the initial stress. In some embodiments, the polymeric material, a first region of the polymeric material, and/or a second region of the polymeric material has a stress remaining greater than or equal to 0.01 MPa. In certain embodiments, the polymeric material, a first region of the polymeric material, and/or a second region of the polymeric material is characterized by a stress remaining of 0.01 MPa to 15 MPa. In certain aspects, the polymeric material, a first region of the polymeric material, and/or a second region of the polymeric material is characterized by a stress remaining of 2 MPa to 15 MPa.

In some embodiments, the polymeric materials, a first region of the polymeric materials, and/or a second region of the polymeric materials are characterized by a stress remaining of 5% to 85% of the initial load, such as 5% to 45%, 15% to 85%, or 20% to 45% of the initial load. In some embodiments, the polymeric material, a first region of the polymeric material, and/or a second region of the polymeric material is characterized by a stress remaining of 0.01 MPa to 15 MPa, such as 2 MPa to 15 MPa. In some embodiments, the polymeric material, a first region of the polymeric material, and/or a second region of the polymeric material is characterized by a stress remaining of greater than or equal to 20% of the initial load. In some embodiments, stress remaining is assessed according to ASTM E328.

In certain embodiments, it is advantageous that the polymeric material, a first region of the polymeric material, and/or a second region of the polymeric material have a high flexural modulus, forming relatively stiff materials. In some embodiments, the polymeric material, a first region of the polymeric material, and/or a second region of the polymeric material has a flexural modulus remaining of 50 MPa or more, 60 MPa or more, 70 MPa or more, 80 MPa or more, 90 MPa or more, 100 MPa or more, 125 MPa or more, or 150 MPa or more. In some embodiments, the flexural modulus remaining is measured after 24 hours in a wet environment at a use temperature. In certain embodiments, the use temperature is 37° C. In some embodiments, flexural modulus is assessed according to ASTM D790.

In certain other embodiments, it is advantageous that the polymeric material, a first region of the polymeric material, and/or a second region of the polymeric material have a relatively low flexural stress remaining, forming materials that are not overly stiff. In some embodiments, the polymeric material, a first region of the polymeric material, and/or a second region of the polymeric material has a flexural stress remaining of 80 MPa or less, 70 MPa or less, 60 MPa or less, 55 MPa or less, 50 MPa or less, or 45 MPa or less. In some embodiments, the flexural stress remaining is measured after 24 hours in a wet environment at a use temperature. In some embodiments, the use temperature is 37° C. In some embodiments, the polymeric material, a first region of the polymeric material, and/or a second region of the polymeric material is characterized by a stress remaining after 24 hours testing in a wet environment at 37° C. of 0.01 MPa to 15 MPa, or a stress remaining of 2 MPa to 15 MPa. In some embodiments, stress remaining is assessed according to ASTM E328.

In some embodiments, a polymeric material, a first region of the polymeric material, and/or a second region of the polymeric material can have a flexural stress remaining after a certain amount of time of use. As a non-limiting example, an orthodontic appliance (e.g., an aligner) can be formed of a polymeric material having a high flexural stress, but following application of the appliance to the teeth of a patient, there can be a significant and fast decrease of flexural stress (e.g., over the course of minutes). Such decreases in flexural stress can follow an exponential curve of decrease leading towards an asymptote during the intended lifetime of the appliance (e.g., over the course of weeks for an orthodontic appliance such as an aligner). In some embodiments, the polymeric material, a first region of the polymeric material, and/or a second region of the polymeric material has a flexural stress remaining of 90 MPa or less, 85 MPa or less, 80 MPa or less, 75 MPa or less, 70 MPa or less, 65 MPa or less, 60 MPa or less, 55 MPa or less, or 50 MPa or less after a certain time period of use. In some embodiments, the polymeric material, a first region of the polymeric material, and/or a second region of the polymeric material has a flexural stress remaining of 80 MPa or less after a time period of use. In some embodiments, the time period of use is 1 minute, 5 minutes, 10 minutes, 30 minutes, 1 hour, 24 hours, 48 hours, 1 week, 2 weeks, 1 month, 2 months, 6 months, 1 year, 2 years, or more than 2 years. As a non-limiting example, an aligner composed of a polymeric material described herein and placed onto a patient's teeth is removed after 10 minutes and has a flexural stress of 70 MPa can be characterized by a flexural stress remaining of 70 MPa after the time period of use, wherein the time period is 10 minutes. In some embodiments, stress remaining is assessed according to ASTM E328.

In some embodiments, the polymeric material, a first region of the polymeric material, and/or a second region of the polymeric material is characterized by an elongation at break greater than 10%, an elongation at break greater than 20%, an elongation at break greater than 30%, an elongation at break of 5% to 250%, an elongation at break of 20% to 250%, or an elongation at break value between 40% and 250%. In certain embodiments, the elongation at break is measured in dry conditions (e.g., a dry environment). In some embodiments, the polymeric material, a first region of the polymeric material, and/or a second region of the polymeric material is characterized by an elongation at break after 24 hours testing in a wet environment at 37° C. greater than 10%, an elongation at break greater than 20%, an elongation at break greater than 30%, an elongation at break of 5% to 250%, an elongation at break of 20% to 250%, or an elongation at break value between 40% and 250%. In some embodiments, the polymeric material, a first region of the polymeric material, and/or a second region of the polymeric material is characterized by an elongation at break both in dry environment, and after 24 hours testing in a wet environment at 37° C., greater than 10%, an elongation at break greater than 20%, an elongation at break greater than 30%, an elongation at break of 5% to 250%, an elongation at break of 20% to 250%, or an elongation at break value between 40% and 250%. In some embodiments, the polymeric material, a first region of the polymeric material, and/or a second region of the polymeric material is characterized by an elongation at break greater than or equal to 5%, greater than or equal to 10%, greater than or equal to 20%, greater than or equal to 30%, greater than or equal to 40%, or greater than or equal to 50%. In some embodiments, elongation at break is assessed according to ASTM D1708-2 5B.

In some embodiments, the polymeric material, a first region of the polymeric material, and/or a second region of the polymeric material has an elongation at yield greater than 4%, greater than 5%, greater than 6%, greater than 7%, greater than 8%, greater than 9%, greater than 10%, greater than 11%, greater than 12%, greater than 13%, greater than 14%, or greater than 15%. In some embodiments, the polymeric material, a first region of the polymeric material, and/or a second region of the polymeric material has an elongation at yield of 4% to 10% or 5% to 15%. In certain embodiments, the elongation at yield is measured in dry conditions (e.g., a dry environment). In some embodiments, the polymeric material, a first region of the polymeric material, and/or a second region of the polymeric material has an elongation at yield greater than 4%, greater than 5%, greater than 6%, greater than 7%, greater than 8%, greater than 9%, greater than 10%, greater than 11%, greater than 12%, greater than 13%, greater than 14%, or greater than 15% after 24 hours testing in a wet environment at 37° C. In some embodiments, the polymeric material, a first region of the polymeric material, and/or a second region of the polymeric material has an elongation at yield of 4% to 10% or 5% to 15% after 24 hours testing in a wet environment at 37° C. In some embodiments, the polymeric material, a first region of the polymeric material, and/or a second region of the polymeric material has an elongation at yield greater than 4%, greater than 5%, greater than 6%, greater than 7%, greater than 8%, greater than 9%, greater than 10%, greater than 11%, greater than 12%, greater than 13%, greater than 14%, or greater than 15% both in dry environment, and after 24 hours testing in a wet environment at 37° C. In some embodiments, the polymeric material, a first region of the polymeric material, and/or a second region of the polymeric material has an elongation at yield of 4% to 10% or 5% to 15% both in a dry environment, and after 24 hours testing in a wet environment at 37° C. In some embodiments, elongation at yield is assessed according to ISO 527-2 5B.

In some embodiments, the polymeric material, a first region of the polymeric material, and/or a second region of the polymeric material has at least one glass transition temperature ($T_g$) from 0° C. to 150° C. In some embodiments, the polymeric material, a first region of the polymeric material, and/or a second region of the polymeric material has at least one glass transition temperature greater than 60° C. In some embodiments, the polymeric material, a first region of the polymeric material, and/or a second region of the polymeric material has at least one glass transition temperature greater than 75° C. In some embodiments, the at least one glass transition temperature is from 0° C. to 200° C., from 0° C. to 140° C., from 0° C. to 20° C., from 20° C. to 40° C., from 40° C. to 60° C., from 60° C. to 80° C., from 80° C. to 100° C., from 100° C. to 120° C., from 120° C. to 140° C., from 140° C. to 160° C., from 160° C. to 180° C., from 180° C. to 200° C., from 0° C. to 35° C., from 35° C. to 65° C., from 65° C. to 100° C., from 0° C. to 50° C., or from 50° C. to 100° C. In some embodiments, the polymeric material, a first region of the polymeric material, and/or a second region of the polymeric material has at least one glass transition temperature from 0° C. to 10° C., from 10° C. to 20° C., from 20° C. to 30° C., from 30° C. to 40° C., from 40° C. to 50° C., from 50° C. to 60° C., from 60° C. to 70° C., from 70° C. to 80° C., or from 80° C. to 90° C. In some embodiments, the polymeric material, a first region of the polymeric material, and/or a second region of the polymeric material has at least one glass transition temperature from −100° C. to 40° C., from −80° C. to 10° C., from −70° C. to 0° C., from −70° C. to −10° C., from −70° C. to −20° C., from −70° C. to −30° C., from −70° C. to −40° C., from −70° C. to −50° C., or from −80° C. to −40° C. In some embodiments, the polymeric material, a first region of the polymeric material, and/or a second region of the polymeric material has at least two glass transition temperatures. In some embodiments, the polymeric material, a first region of the polymeric material, and/or a second region of the polymeric material has a first $T_g$ less than 40° C. and a second $T_g$ greater than 60° C., a first $T_g$ less than 0° C. and a second $T_g$ greater than 60° C., a first $T_g$ less than 0° C. and a second $T_g$ greater than 75° C., or a first $T_g$ less than −20° C. and a second $T_g$ greater than 80° C. In some embodiments, glass transition temperature is assessed with dynamic mechanical analysis as the tan δ peak when run at 1 hz with a temperature ramp of 2° C. a minute. In some embodiments, the $T_g$ is measured immediately after soaking in water at 37° C. for 24 hours.

In some embodiments, the polymeric material, a first region of the polymeric material, and/or a second region of the polymeric material is clear, substantially clear, mostly clear, or opaque. In certain embodiments, the polymeric material, a first region of the polymeric material, and/or a second region of the polymeric material is clear. In certain embodiments, the polymeric material, a first region of the polymeric material, and/or a second region of the polymeric material is substantially clear. In certain embodiments, the polymeric material, a first region of the polymeric material, and/or a second region of the polymeric material is mostly clear. In some embodiments, greater than 70%, greater than 80%, greater than 90%, greater than 95%, or greater than 99% of visible light passes through the polymeric material, a first region of the polymeric material, and/or a second region of the polymeric material. Transparency can be measured using a UV-Vis spectrophotometer. In some embodiments, the transparency is measured by measuring the passage of a wavelength of transparency. In some embodiments, greater than 70%, greater than 80%, greater than 90%, greater than 95%, or greater than 99% of the wavelength of transparency can pass through the polymeric material, a first region of the polymeric material, and/or a second region of the polymeric material. In some embodiments, the wavelength of transparency is in the visible light range (i.e., from 400 nm to 800 nm), is in the infrared light range, or is in the ultraviolet light range. In some embodiments, the polymeric material, a first region of the polymeric material, and/or a second region of the polymeric material does not have color. In other embodiments, the polymeric material, a first region of the polymeric material, and/or a second region of the polymeric material appears white, off-white, or mostly transparent with white coloring, as detected by the human eye.

In some embodiments, greater than 20%, greater than 30%, greater than 40%, greater than 50%, greater than 60%, greater than 70%, greater than 80%, greater than 90%, or greater than 95% of visible light passes through the polymeric material, a first region of the polymeric material, and/or a second region of the polymeric material, after 24 hours in a wet environment at 37° C. In some embodiments, greater than 70% of visible light passes through the polymeric material, a first region of the polymeric material, and/or a second region of the polymeric material, after 24 hours in a wet environment at 37° C.

Figure 6:
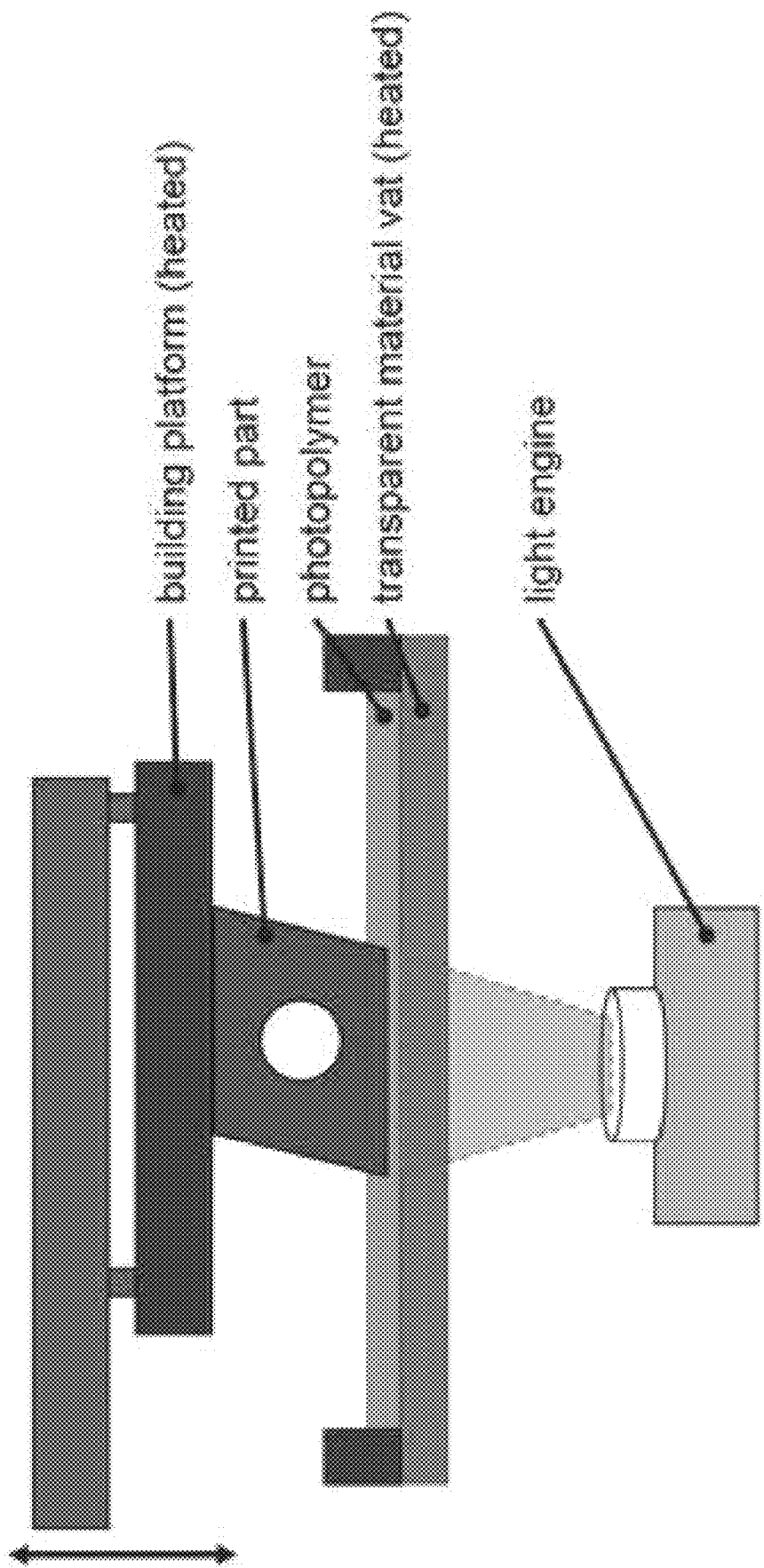
FIG. 6 shows a schematic configuration of a high temperature additive manufacturing device used for curing a curable composition of the present disclosure by using a 3D printing process.

In some embodiments, the polymeric material, a first region of the polymeric material, and/or a second region of the polymeric material is biocompatible, bioinert, or a combination thereof. In some embodiments, the polymeric material is formed using 3D printing (i.e., by additive manufacturing, FIG. 6) using photopolymerization. In some embodiments, the polymeric material can be used in coatings, molds, injection molding machines, or other manufacturing methods that use or could use light during the curing process. In some embodiments, the polymeric material, a first region of the polymeric material, and/or a second region of the polymeric material is well suited for applications that require, e.g., solvent resistance, humidity resistance, water resistance, creep resistance, or heat deflection resistance.

Methods of Making Polymeric Materials

In some aspects, the present disclosure provides a method of forming a cured polymeric material, the method comprising: providing a resin as described herein; and curing the resin, thereby forming a cured polymeric material.

In some embodiments, the present disclosure provides a method of producing polymeric materials described herein generated from printable resins as described further herein. In some embodiments, the method comprises the steps of: providing a resin, as disclosed further herein; and initiating a polymerization reaction by curing the resin, thereby forming a cured polymeric material.

In some embodiments, the method further comprises the step of fabricating a device using an additive manufacturing device, wherein said additive manufacturing device facilitates the curing. In some embodiments, the curing of the resin produces the polymeric material. In certain embodiments, the resin is cured using an additive manufacturing device to produce the polymeric material. In some embodiments, the method further comprises the step of cleaning the polymeric material. In certain embodiments, the cleaning of the polymeric material includes washing and/or rinsing the polymeric material with a solvent, which can remove monomers and undesired impurities from the polymeric material. In other embodiments, the cleaning of the polymeric materials includes the use of a centrifuge. One or more cleaning method(s) may be used to clean a polymeric material disclosed herein.

In some embodiments, the present disclosure provides a method of forming a cured polymeric material comprising: providing a resin, the resin comprising: a first continuous phase comprising a component having a first reactivity (i.e., a first component); and a second continuous phase comprising a component having a second reactivity (i.e., a second component); and polymerizing the resin, thereby forming the cured polymeric material. In some embodiments, the first reactivity is greater than the second reactivity (i.e., the first component is more reactive than the second component). In some embodiments, the resin is a 3D printable resin.

In some embodiments, polymerizing the resin is unpatterned. For example, exposure to a source of light to induce polymerization without use of a mask is unpatterned. In some embodiments, polymerizing the resin uses mask-free polymerization. In some embodiments, a material formed from unpatterned polymerization comprises smaller features in comparison to a material formed from patterned polymerization (e.g., with application of a mask).

In some embodiments, polymerizing the resin comprises processing the multiple phases with distinct steps. In some embodiments, polymerizing the resin comprises a first processing step and a separate, distinct second processing step. In some embodiments, the first processing step processes (e.g., polymerizes) the first component and the second processing step processes (e.g., polymerizes) the second component. In some embodiments, the first processing step polymerizes the first component, thereby forming a first polymer. In some embodiments, the second processing step polymerizes the second component, thereby forming a second polymer. In some embodiments, the first processing step comprises exposure to light (e.g., for photopolymerization). In some embodiments, the first processing step comprises exposure to a temperature (e.g., for thermal polymerization). In some embodiments, the second processing step comprises exposure to light (e.g., for photopolymerization). In some embodiments, the second processing step comprises exposure to a temperature (e.g., for thermal polymerization).

A separate processing step can be advantageous in controlling the rate and order of polymerization of components present in the resin. As a non-limiting example, in some embodiments, the first continuous phase is polymerized separately from the second continuous phase by controlling exposure wavelength (e.g., in photopolymerization) or exposure temperature (e.g., in thermal polymerization). In some embodiments, separate processing comprises processing the same region. In some embodiments, separate processing comprises processing the same region at different times. As a non-limiting example, a first processing step can take place 1 millisecond prior to the second processing step. As a non-limiting example, a resin can be exposed to a first wavelength of light, thereby inducing polymerization of a first component, and can thereafter be exposed to a second wavelength of light, thereby inducing polymerization of a second component.

In some embodiments, the time difference between the first processing step and the second processing step is less than 1 millisecond, less than 10 milliseconds, less than 100 milliseconds, less than 200 milliseconds, less than 300 milliseconds, less than 400 milliseconds, less than 500 milliseconds, less than 1 second, or less than or equal to 5 seconds. In certain embodiments, the time difference between the first processing step and the second processing step is greater than 5 seconds. In some embodiments, the time difference between the first processing step and the second processing step is from less than 1 millisecond to 10 milliseconds, from less than 1 millisecond to 100 milliseconds, from less than 1 millisecond to 200 milliseconds, from less than 1 millisecond to 300 milliseconds, from less than 1 millisecond to 400 milliseconds, from less than 1 millisecond to 500 milliseconds, or from less than 1 millisecond to 1 second. In some embodiments, the first processing step is processed first and the second processing step is processed second. In some embodiments, it is advantageous to have an alternate processing order. In certain embodiments, the second processing step is processed first and the first processing step is processed second. Such changes in the process step order can be especially useful during a print to obtain very different properties at different layer heights and/or different spatial locations.

In some embodiments, a hard phase is processed separately from a soft phase of the resin. In some embodiments, the first continuous phase is the soft phase and the second continuous phase is the hard phase. In some embodiments, the present disclosure provides a method of separately processing a hard phase and a soft phase of the resins described herein. In some embodiments, it is preferable that the soft phase is processed (e.g., polymerized) before the hard phase. In some embodiments, it is preferable that the soft phase comprises components having higher reactivity than the components of the hard phase (e.g., such that the soft phase is processed, or polymerized, first). In some embodiments, the soft phase is characterized by having components with higher reactivity than the components of the hard phase.

In some embodiments, curing the resin comprises photocuring the resin. In some embodiments, curing the resin comprises thermal curing the resin. In some embodiments, curing the resin comprises photocuring and thermal curing the resin. As further described herein, in some embodiments the soft phase is characterized by comprising a component having higher reactivity relative to the components of the hard phase.

In some embodiments, the phases of the resin are processed separately. In some embodiments, a first portion of the resin is cured, and a second portion of the resin is cured at a different step. As a non-limiting example, a resin comprising two phases can be selectively cured such that a first phase is cured prior to the curing of the second phase.

In some embodiments, the curing of the phases overlap spatially but differ in time (e.g., milliseconds). In certain embodiments, curing the resin comprises at least two photocuring steps. In some embodiments, curing the resin comprises two photocuring steps. In certain embodiments, curing the resin comprises two or more photocuring steps. In certain embodiments, curing the resin comprises at least two thermal curing steps. In some embodiments, curing the resin comprises two thermal curing steps. In certain embodiments, curing the resin comprises two or more thermal curing steps. In some embodiments, curing the resin comprises at least one photocuring step and at least one thermal curing step. In some embodiments, curing the resin comprises one photocuring step and one thermal curing step.

In some embodiments, the method further comprises fabricating an object with the cured polymeric material. In certain embodiments, the fabricating comprises additive manufacturing, as further described herein. In some embodiments, the fabricating comprises printing the resin with a 3D printer. In some embodiments, the fabricating comprises stereolithography, digital light processing, two photon-induced photopolymerization, inkjet printing, multijet printing, fused deposition modeling, or any combination thereof. In certain embodiments, fabricating the object occurs following the polymerizing step. In some embodiments, fabricating the object occurs following the first processing step and/or following the second processing step. In some embodiments, 3D printing provides increased control of thickness when forming an object as described further herein, and thus has improved characteristics over thermoforming.

In some embodiments, a plurality of components (e.g., first and second components and/or first and second monomers) as described further herein are incorporated into the cured polymeric material during the curing step. In some embodiments, the plurality of monomers are incorporated into the cured polymeric material following the curing step. In certain embodiments, curing the resin comprises exposure to a light source. In some embodiments, curing the resin comprises radical curing, ionic curing, or a combination thereof.

In some embodiments, curing the resin forms a polymeric material comprising an interpenetrated network comprising polymers described herein, formed from the components described herein. In certain embodiments, the method further comprises synthesizing and purifying the plurality of components (e.g., polymerizable monomers).

In some embodiments, the methods disclosed herein are part of a high temperature lithography-based photopolymerization process, wherein a curable composition (i.e., the resin) comprises at least one photopolymerization initiator and is heated, which makes high temperature lithography-based photopolymerization process more preferable as an additive manufacturing process, most preferably a 3D printing process. The method according to the present disclosure offers the possibility of quickly and facilely producing devices, such as orthodontic appliances, by additive manufacturing such as 3D printing using resins as disclosed herein.

Photopolymerization occurs when suitable formulations (e.g., the resins disclosed herein) are exposed to radiation (e.g., UV or visible light) of sufficient power and of a wavelength capable of initiating polymerization. The wavelengths and/or power of radiation useful to initiate polymerization may depend on the photoinitiator used. "Light" as used herein includes any wavelength and power capable of initiating polymerization. Some wavelengths of light include ultraviolet (UV) or visible. UV light sources include UVA (wavelength about 400 nanometers (nm) to about 320 nm), UVB (about 320 nm to about 290 nm) or UVC (about 290 nm to about 100 nm). Any suitable source may be used, including laser sources. The source may be broadband or narrowband, or a combination thereof. The light source may provide continuous or pulsed light during the process. Both the length of time the system is exposed to UV light and the intensity of the UV light can be varied to determine the ideal reaction conditions.

In some embodiments, the methods disclosed herein use additive manufacturing to produce a device comprising or consisting of the cured polymeric material. In certain embodiments, the methods disclosed herein use additive manufacturing to produce a device consisting essentially of the cured polymeric material. Additive manufacturing includes a variety of technologies which fabricate three-dimensional objects directly from digital models through an additive process. In some aspects, successive layers of material are deposited and "cured in place". A variety of techniques are known to the art for additive manufacturing, including selective laser sintering (SLS), fused deposition modeling (FDM) and jetting or extrusion. In many embodiments, selective laser sintering involves using a laser beam to selectively melt and fuse a layer of powdered material according to a desired cross-sectional shape in order to build up the object geometry. In many embodiments, fused deposition modeling involves melting and selectively depositing a thin filament of thermoplastic polymer in a layer-by-layer manner in order to form an object. In yet another example, 3D printing can be used to fabricate the appliances herein. In many embodiments, 3D printing involves jetting or extruding one or more materials (e.g., the resins disclosed herein) onto a build surface to form successive layers of the object geometry. In some embodiments, the resins described herein can be used in inkjet or coating applications. Cured polymeric materials may also be fabricated by "vat" processes in which light is used to selectively cure a vat or reservoir of the curable resin (e.g., the resins disclosed herein). Each layer of curable resin may be selectively exposed to light in a single exposure or by scanning a beam of light across the layer. Specific techniques include stereolithography (SLA), Digital Light Processing (DLP) and two photon-induced photopolymerization (TPIP).

In some embodiments, the methods disclosed herein use continuous direct fabrication to produce a device comprising the cured polymeric material. In certain embodiments, the methods disclosed herein use continuous direct fabrication to produce a device consisting essentially of the cured polymeric material. A non-limiting exemplary direct fabrication process can achieve continuous build-up of an object geometry by continuous movement of a build platform (e.g., along the vertical or Z-direction) during an irradiation phase, such that the hardening depth of the irradiated photopolymer (e.g., the irradiated resin, hardening during the formation of the cured polymeric material) is controlled by the movement speed. Accordingly, continuous polymerization of material (e.g., polymerization of the resin into the cured polymeric material) on the build surface can be achieved. Such methods are described in U.S. Pat. No. 7,892,474, the disclosure of which is incorporated herein by reference in its entirety. In yet another example, a continuous direct fabrication method utilizes a "heliolithography" approach in which the liquid resin (e.g., the resin) is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety. Continuous liquid interface production of 3D objects has also been reported (J. Tumbleston et al., Science, 2015, 347 (6228), pp 1349-1352) hereby incorporated by reference in its entirety for description of the process. Another example of continuous direct fabrication method can involve extruding a material composed of a curable liquid material surrounding a solid strand. The material can be extruded along a continuous three-dimensional path in order to form the object. Such methods are described in U.S. Patent Publication No. 2014/0061974, the disclosure of which is incorporated herein by reference in its entirety.

In some embodiments, the methods disclosed herein use high temperature lithography to produce a device comprising the cured polymeric material. In certain embodiments, the methods disclosed herein use high temperature lithography to produce a device consisting essentially of the cured polymeric material. "High temperature lithography," as used herein, may refer to any lithography-based photopolymerization processes that involve heating photopolymerizable material(s) (e.g., curable resins disclosed herein). The heating may lower the viscosity of the photopolymerizable material(s) before and/or during curing. Non-limiting examples of high-temperature lithography processes include those processes described in WO 2015/075094, WO 2016/078838 and WO 2018/032022. In some implementations, high-temperature lithography may involve applying heat to material to temperatures between 50° C.-120° C., such as 90° C.-120° C., 100° C.-120° C., 105° C.-115° C., 108° C.-110° C., etc. The material may be heated to temperatures greater than 120° C. It is noted other ranges may be used without departing from the scope and substance of the inventive concepts described herein.

In another embodiment, the methods disclosed herein comprise a continuous direct fabrication step. The continuous direct fabrication step can involve extruding a material composed of a curable liquid material (e.g., the resin) surrounding a solid strand. The liquid material can be extruded along a continuous three-dimensional path in order to form an object or device. Such methods are described in U.S. Patent Publication No. 2014/0061974, the disclosure of which is incorporated herein by reference in its entirety. Other related 3D printing technologies that can be used for continuous direct fabrication include volume printing techniques such as xolography and tomographic printing.

In some embodiments, the methods disclosed herein further comprises fabricating an object with the polymeric material. In certain embodiments, fabricating the object comprises additive manufacturing. In some embodiments, fabricating the object with the polymeric material comprises printing with a 3D printer. In some embodiments, fabricating the object with the polymeric material comprises digital light projection. In certain embodiments, fabricating the object with the polymeric material comprises using hot lithography.

In some embodiments, the object is an orthodontic appliance. In some embodiments, the orthodontic appliance is an aligner, expander (e.g., a rapid palatal expander), or spacer. In some embodiments, the orthodontic appliance is an aligner. In some embodiments, the aligner comprises at least one mandibular advancement component. In some embodiments, the aligner comprises at least one attachment formation template. In some embodiments, the orthodontic appliance comprises a plurality of tooth receiving cavities configured to reposition teeth from a first configuration toward a second configuration. In some embodiments, the orthodontic appliance is one of a plurality of orthodontic appliances configured to reposition the teeth from an initial configuration toward a target configuration. In some embodiments, the orthodontic appliance is one of a plurality of orthodontic appliances configured to reposition the teeth from an initial configuration toward a target configuration according to a treatment plan. In some embodiments wherein the orthodontic appliance is an aligner.

Devices Comprising Polymeric Materials of the Present Disclosure

As described further herein, the polymeric materials described herein can provide contrasting properties. A non-limiting example of such contrasting properties is a material having a phase providing high modulus and low elasticity to generate force necessary to, e.g., move teeth, as well as a phase providing low modulus and high elasticity to provide patient comfort, giving a good mouth feel and affording low breakage. Such contrasting properties are favorable in the design of some devices, such as the devices comprising a first and second continuous phase described further herein. A non-limiting example of a device that benefits from contrasting properties includes a rapid palatal expander, which includes a relatively rigid center portion that exerts expansion forces, and relatively flexible side portions, which facilitate insertion and removal of the device to a patient's teeth. Another non-limiting example of a device that benefits from contrasting properties includes an aligner with mandibular advancement features, wherein the mandibular advancement features are denser and/or more rigid than the portion of the aligner that moves teeth of a patient. Another non-limiting example of a device that benefits from contrasting properties includes a prefabricated attachment formation template, which in some embodiments requires areas or regions to be more rigid and other areas or regions to be less rigid.

In some embodiments, the present disclosure provides devices comprising the polymeric materials generated from the resins as described further herein. In some embodiments, the present disclosure provides devices formed from the processes and systems described further herein. In some embodiments, the disclosures are used to create a device intended to be placed in the intraoral cavity of a human. Such devices can be, for example, aligners that help to move teeth to new positions. In some embodiments, the devices can be retainers that help to keep teeth from moving to a new position. In some embodiments, the device can be used to expand the palate, move the location of the jaw, or prevent snoring of a human.

In some embodiments, the present disclosure provides methods for producing the devices described herein, said devices comprising a polymeric material. In some embodiments, the method comprises a step of shaping a resin into a desirable shape prior to a step of curing the resin, thereby generating the polymeric material having said desirable shape. In some embodiments, the method comprises a step of shaping a resin into a desirable shape during a step of curing the resin, thereby generating the polymeric material having the desirable shape. In some embodiments, the method comprises a step of curing the resin, thereby forming the polymeric material, then shaping the polymeric material into a desirable shape. In some embodiments, the desirable shape is an orthodontic appliance. In some embodiments, the desirable shape is a device and/or object as disclosed herein. In some embodiments, the shaping step comprises extrusion, production of a sheet, production of a film, melt spinning, coating, injection molding, compression and transfer molding, blow molding, rotational blow molding, thermoforming, casting, or a combination thereof. In some embodiments, the polymeric materials described herein are thermoplastic or thermoset. In certain embodiments, the thermoplastic(s) tend to perform better with molding techniques, though the properties of the materials disclosed herein allow for thermosets to be molded. In some embodiments, the materials disclosed herein are shape memory materials.

Exemplary embodiments of devices that can be cured using the materials disclosed herein include dental appliances for use in humans. In some embodiments, such devices can be used as treatment systems for providing an orthodontic treatment.

In certain aspects, the present disclosure provides a method of making an orthodontic appliance comprising a polymeric material as described herein, the method comprising providing a resin as further described herein; and fabricating the polymeric material by a direct or additive fabrication process. The resin may be exposed to light in said direct or additive fabrication process. The process may further comprise an additional curing step following fabrication of the polymeric material.

In certain aspects, the present disclosure provides an orthodontic appliance comprising a polymeric material as further described herein. The orthodontic appliance may be an aligner, expander or spacer. In some embodiments, the orthodontic appliance comprises a plurality of tooth receiving cavities configured to reposition teeth from a first configuration toward a second configuration. In some embodiments, the orthodontic appliance is one of a plurality of orthodontic appliances configured to reposition the teeth from an initial configuration toward a target configuration, optionally according to a treatment plan. As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

The curable resins and cured polymeric materials according to the present disclosure exhibit favorable thermomechanical properties for use as orthodontic appliances, for example, for moving one or more teeth.

The embodiments disclosed herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. In some cases, the reinforced composites can comprise a polymer matrix reinforced with ceramic or metallic particles, for example. The appliance can be shaped in many ways, such as with thermoforming or direct fabrication as described herein, for example. Alternatively, or in combination, the appliance can be fabricated with machining such as an appliance fabricated from a block of material with computer numeric control machining. Preferably, the appliance is fabricated using a curable resin according to the present disclosure.

Turning now to the drawings, in which like numbers designate like elements in the various figures, FIG. 1A illustrates an exemplary tooth repositioning appliance or aligner (100) that can be worn by a patient in order to achieve an incremental repositioning of individual teeth (102) in the jaw, and comprises the cured polymeric material disclosed herein. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements (104) on teeth (102) with corresponding receptacles or apertures (106) in the appliance (100) so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
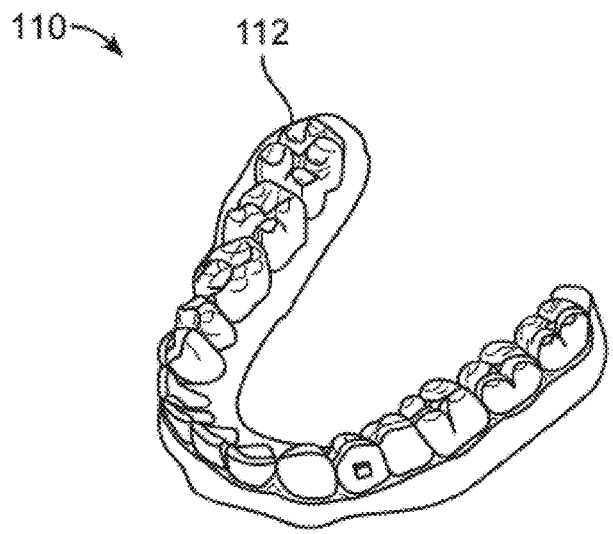
FIG. 1B illustrates a tooth repositioning system, in accordance with embodiments.
Figure 1B:
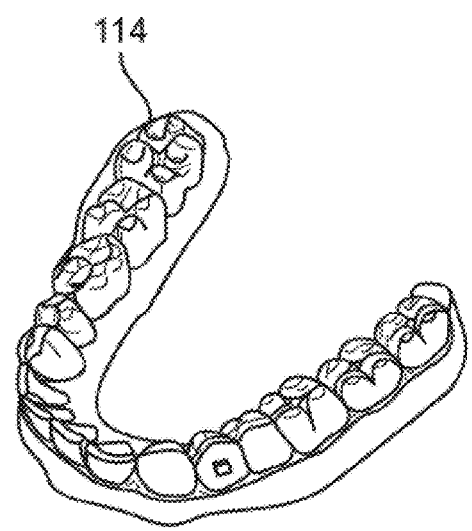
Figure 1B:
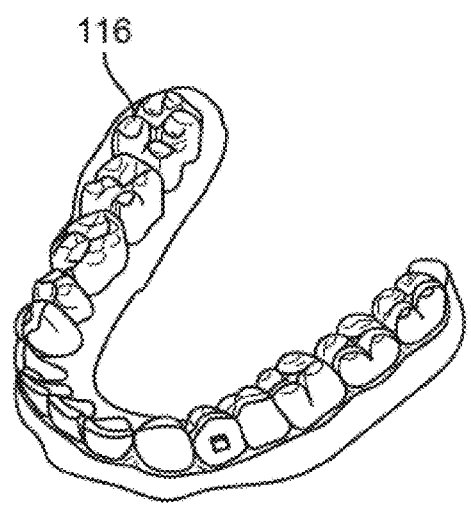

FIG. 1B illustrates a tooth repositioning system (110) including a plurality of appliances (112), (114), (116). Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system (110) can include a first appliance (112) corresponding to an initial tooth arrangement, one or more intermediate appliances (114) corresponding to one or more intermediate arrangements, and a final appliance (116) corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

FIG. 1C illustrates a method (150) of orthodontic treatment using a plurality of appliances, in accordance with embodiments. The method (150) can be practiced using any of the appliances or appliance sets described herein. In step (160), a first orthodontic appliance is applied to a patient's teeth in order to reposition the teeth from a first tooth arrangement to a second tooth arrangement. In step (170), a second orthodontic appliance is applied to the patient's teeth in order to reposition the teeth from the second tooth arrangement to a third tooth arrangement. The method (150) can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively, or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively, or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. In some embodiments, the direct fabrication techniques described herein can be used to produce appliances with substantially anisotropic material properties (e.g., having substantially different strengths along all directions). In some embodiments, the direct fabrication techniques described herein can produce an orthodontic appliance having a strength that varies by more than 10%, more than 15%, more than 20%, or more than 25% along all directions, but in a controlled manner. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, sunlight, or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 2:
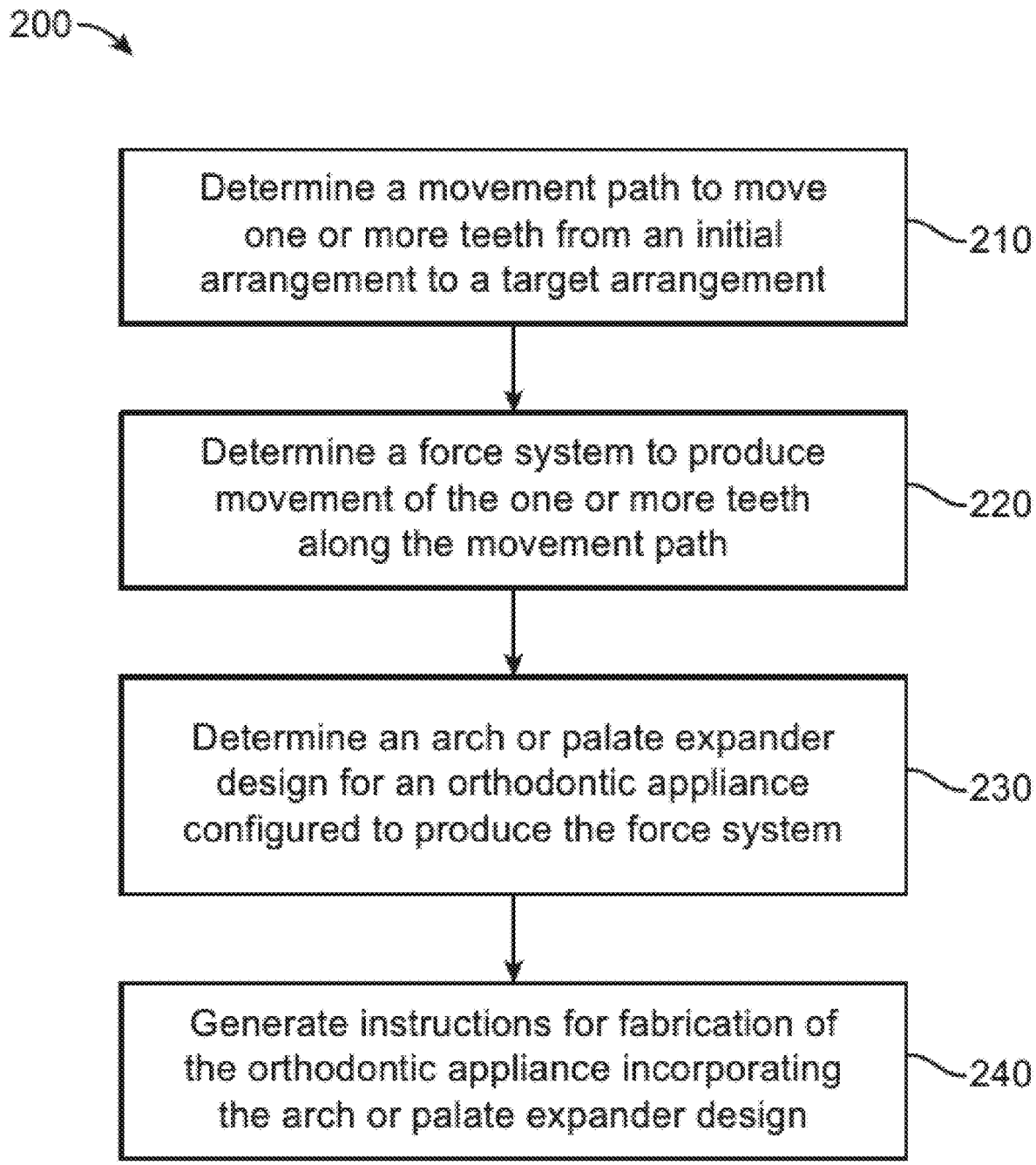
FIG. 2 illustrates a method for designing an orthodontic appliance, in accordance with embodiments.

FIG. 2 illustrates a method (200) for designing an orthodontic appliance to be produced by direct fabrication, in accordance with embodiments. The method (200) can be applied to any embodiment of the orthodontic appliances described herein. Some or all of the steps of the method (200) can be performed by any suitable data processing system or device, e.g., one or more processors configured with suitable instructions.

In step (210), a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step (220), a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step (230), an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA For creating finite element models and analyzing them, program products from a number of vendors can be used, including finite element analysis packages from ANSYS, Inc., of Canonsburg, PA, and SIMULIA(Abaqus) software products from Dassault Systèmes of Waltham, MA.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step (240), instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method (200) may comprise additional steps: 1) The upper arch and palate of the patient is scanned intraorally to generate three-dimensional data of the palate and upper arch; 2) The three-dimensional shape profile of the appliance is determined to provide a gap and teeth engagement structures as described herein.

Although the above steps show a method (200) of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method (200) may be performed with any suitable fabrication system or device, such as the embodiments described herein. Some of the steps may be optional, and the order of the steps can be varied as desired.

Figure 3:
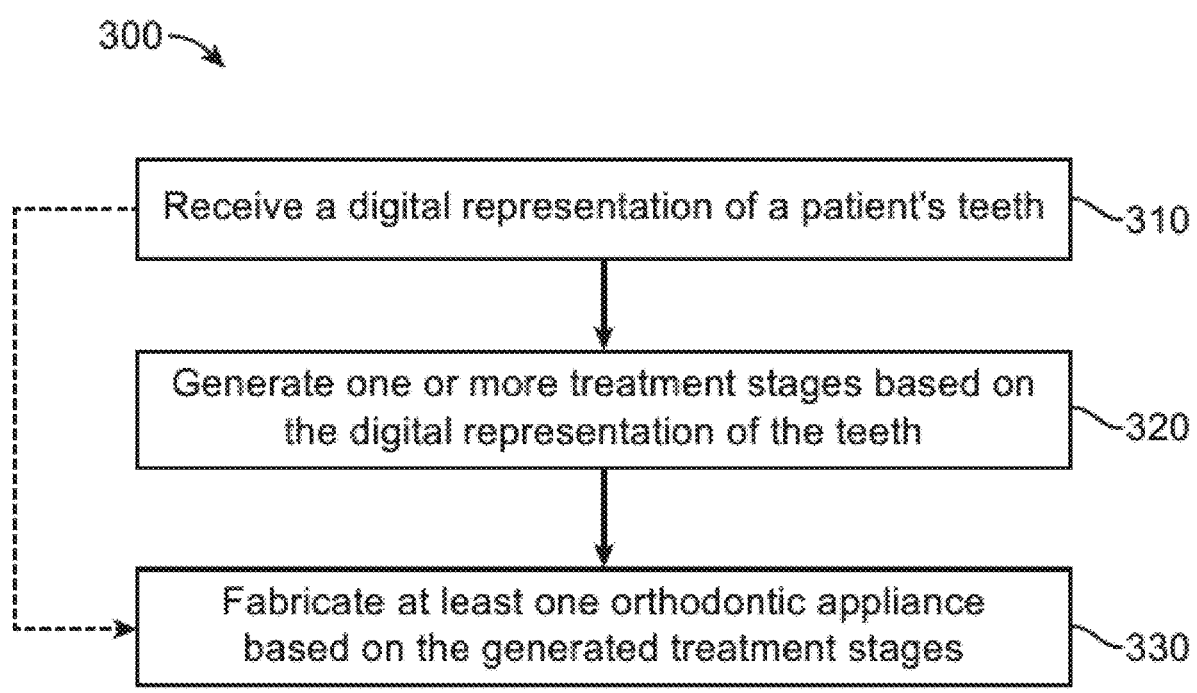
FIG. 3 illustrates a method for digitally planning an orthodontic treatment, in accordance with embodiments.

FIG. 3 illustrates a method (300) for digitally planning an orthodontic treatment and/or design or fabrication of an appliance, in accordance with embodiments. The method (300) can be applied to any of the treatment procedures described herein and can be performed by any suitable data processing system.

In step (310), a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step (320), one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step (330), at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth (310)), followed by design and/or fabrication of an orthodontic appliance based on a representation of the patient's teeth in the arrangement represented by the received representation.

On-Track Treatment

In some embodiments, this disclosure provides a method for repositioning a patient's teeth, the method comprising applying an orthodontic appliance disclosed herein to at least one of a patient's teeth, and moving at least one of the patient's teeth toward an intermediate arrangement or a final tooth arrangement.

In some embodiments, this disclosure provides a method of repositioning a patient's teeth, the method comprising: generating a treatment plan for a patient, the plan comprising a plurality of intermediate tooth arrangements for moving teeth along a treatment path from an initial arrangement toward a final arrangement; producing a 3D printed orthodontic appliance comprising a material as further described herein; and moving on-track, with the orthodontic appliance, at least one of the patient's teeth toward an intermediate arrangement or a final tooth arrangement.

Figure 4:
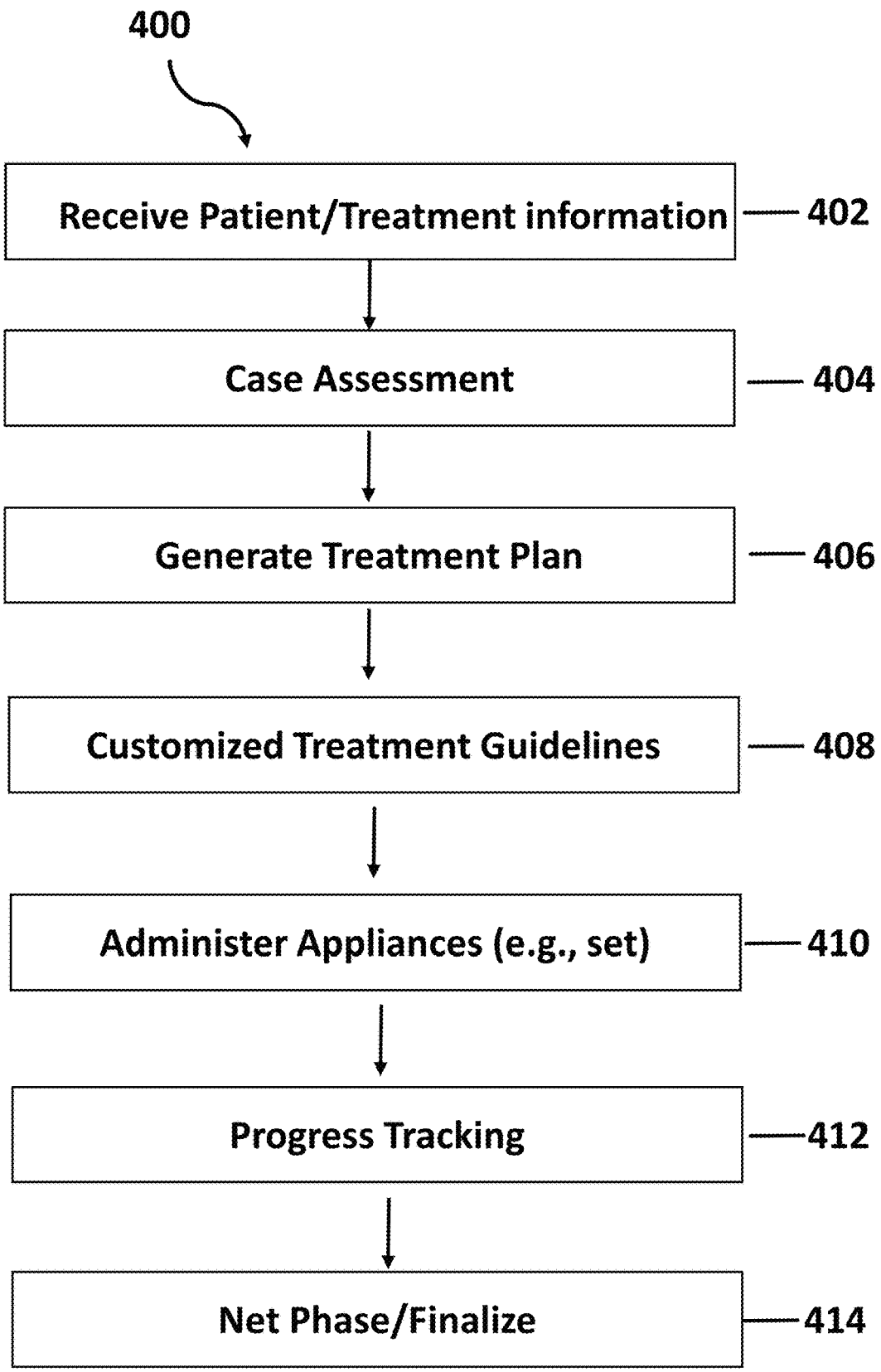
FIG. 4 shows generating and administering treatment according to an embodiment of the present invention.
Figure 5:
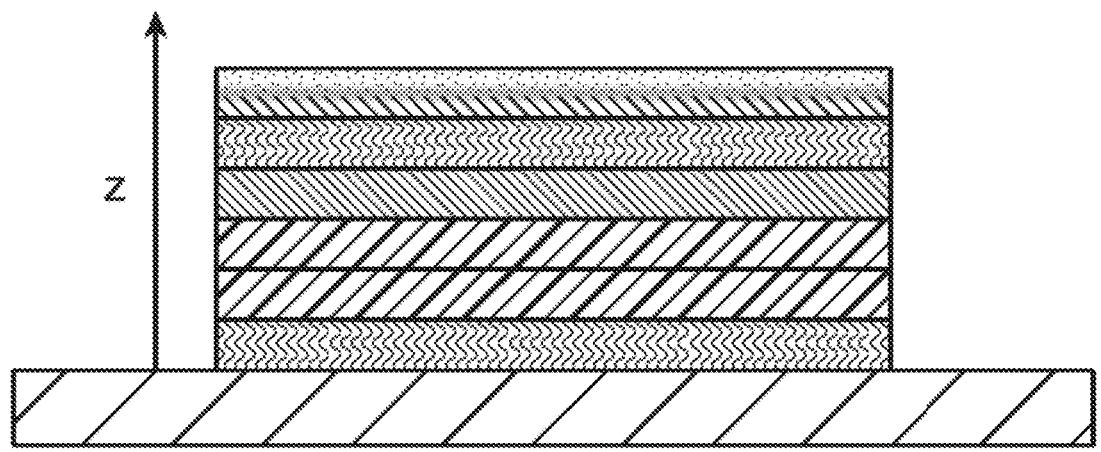
FIG. 5 illustrates the lateral dimensions and vertical dimension as used herein.
Figure 5:
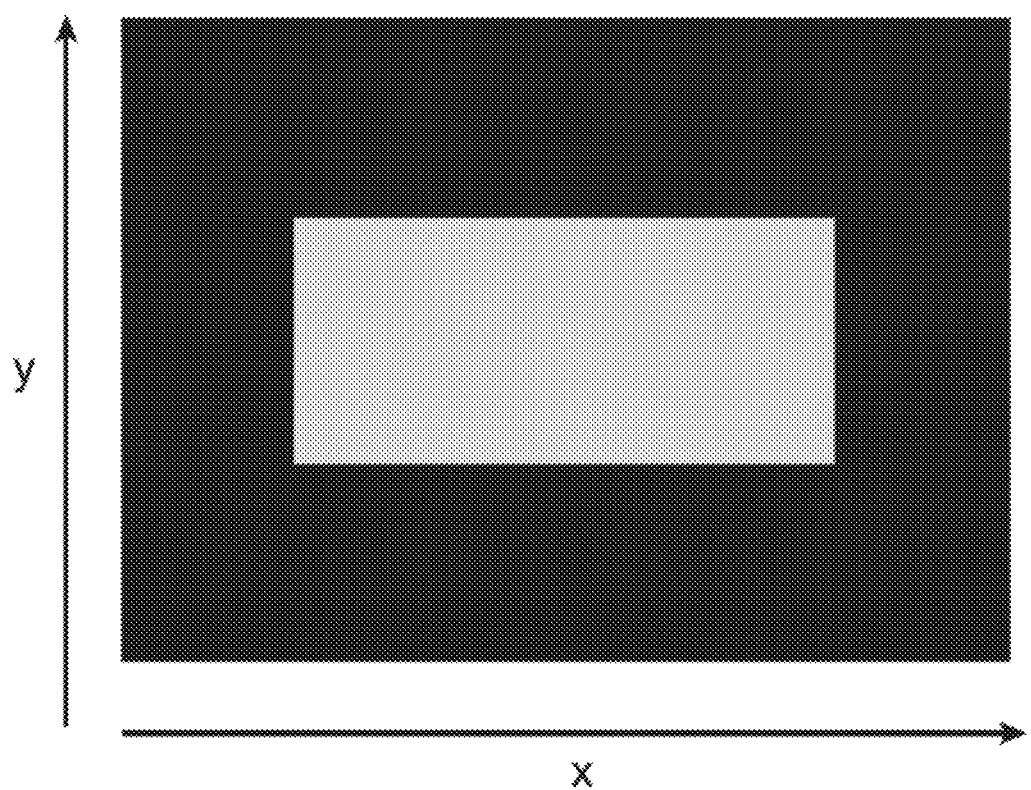

Referring to FIG. 4, a process (400) according to the present disclosure is illustrated. Individual aspects of the process are discussed in further detail below. The process includes receiving information regarding the orthodontic condition of the patient and/or treatment information (402), generating an assessment of the case (404), and generating a treatment plan for repositioning a patient's teeth (406). Briefly, a patient/treatment information will include obtaining data comprising an initial arrangement of the patient's teeth, which typically includes obtaining an impression or scan of the patient's teeth prior to the onset of treatment and can further include identification of one or more treatment goals selected by the practitioner and/or patient. A case assessment can be generated (404) so as to assess the complexity or difficulty of moving the particular patient's teeth in general or specifically corresponding to identified treatment goals, and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (408). The treatment plan typically includes multiple phases of treatment, with a customized set of treatment guidelines generated that correspond to a phase of the treatment plan. The guidelines will include detailed information on timing and/or content (e.g., specific tasks) to be completed during a given phase of treatment, and will be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines are said to be customized. The customized treatment guidelines are then provided to the practitioner so as to help instruct the practitioner as how to deliver a given phase of treatment. As set forth above, appliances can be generated based on the planned arrangements and will be provided to the practitioner and ultimately administered to the patient (410). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (412). If the patient's teeth are determined to be "on-track" and progressing according to the treatment plan, then treatment progresses as planned and treatment progresses to the next stage of treatment (414). If the patient's teeth have substantially reached the initially planned final arrangement, then treatment progresses to the final stages of treatment (414). Where the patient's teeth are determined to be tracking according to the treatment plan, but have not yet reached the final arrangement, the next set of appliances can be administered to the patient.

The threshold difference values of a planned position of teeth to actual positions selected as indicating that a patient's teeth have progressed on-track are provided below in Table 1. If a patient's teeth have progressed at or within the threshold values, the progress is considered to be on-track. If a patient's teeth have progressed beyond the threshold values, the progress is considered to be off-track.

TABLE 1

| Type Movement | Difference Actual/Planned |
|---|---|
| Rotations | |
| Upper Central Incisors | 9 degrees |
| Upper Lateral Incisors | 11 degrees |
| Lower Incisors | 11 degrees |
| Upper Cuspids | 11 degrees |
| Lower Cuspids | 9.25 degrees |
| Upper Bicuspids | 7.25 degrees |
| Lower First Bicuspid | 7.25 degrees |
| Lower Second Bicuspid | 7.25 degrees |
| Molars | 6 degrees |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 degrees |
| Posterior | 3.7 degrees |
| Inclination | |
| Anterior | 5.5 degrees |
| Posterior | 3.7 degrees |
| Translation | |
| BL Anterior | 0.7 mm |
| BL Posterior Cuspids | 0.9 mm |
| MD Anterior | 0.45 mm |

TABLE 1-continued

| Type Movement | Difference Actual/Planned |
|---|---|
| MD Cuspids | 0.45 mm |
| MD Posterior | 0.5 mm |

The patient's teeth are determined to be on track by comparison of the teeth in their current positions with teeth in their expected or planned positions, and by confirming the teeth are within the parameter variance disclosed in Table 1. If the patient's teeth are determined to be on track, then treatment can progress according to the existing or original treatment plan. For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether a patient's teeth are progressing as planned or if the teeth are off track.

In some embodiments, as further disclosed herein, this disclosure provides methods of treating a patient using a 3D printed orthodontic appliance. In certain embodiments, the method of repositioning a patient's teeth (or, in some embodiments, a singular tooth) comprises: generating a treatment plan for the patient, the plan comprising tooth arrangements for moving teeth along a treatment path from an initial arrangement toward a final arrangement; producing a 3D printed orthodontic appliance; and moving on-track, with the orthodontic appliance, at least one of the patient's teeth toward an intermediate arrangement or a final tooth arrangement. In some embodiments, producing the 3D printed orthodontic appliance uses the resins disclosed further herein. On-track performance can be determined, e.g., from Table 1, above.

In some embodiments, the method further comprises tracking the progression of the patient's teeth along the treatment path after administration of the orthodontic appliance. In certain embodiments, the tracking comprises comparing a current arrangement of the patient's teeth to a planned arrangement of the teeth. As a non-limiting example, following the initial administration of the orthodontic appliance, a period of time passes (e.g., two weeks), a comparison of the now-current arrangement of the patient's teeth (i.e., at two weeks of treatment) can be compared with the teeth arrangement of the treatment plan. In some embodiments, the progression can also be tracked by comparing the current arrangement of the patient's teeth with the initial configuration of the patient's teeth. The period of time can be, for example, greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 2 weeks, greater than 3 weeks, greater than 4 weeks, or greater than 2 months. In some embodiments, the period of time can be from at least 3 days to at most 4 weeks, from at least 3 days to at most 3 weeks, from at least 3 days to at most 2 weeks, from at least 4 days to at most 4 weeks, from at least 4 days to at most 3 weeks, or from at least 4 days to at most 2 weeks. In certain embodiments, the period of time can restart following the administration of a new orthodontic appliance.

In some embodiments, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% of the patient's teeth are on track with the treatment plan after a period of time of using an orthodontic appliance as disclosed further herein. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

Device Properties

In some embodiments of the method disclosed above, the 3D printed orthodontic appliance has a retained repositioning force (i.e., the repositioning force after the orthodontic appliance has been applied to or worn by the patient over a period of time), and the retained repositioning force to at least one of the patient's teeth after the period of time is at least 10%, at least 20%, at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, or at least 99% of the repositioning force initially provided to the at least one of the patient's teeth (i.e., with initial application of the orthodontic appliance). In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In some embodiments, the orthodontic appliances disclosed herein can provide on-track movement of at least one of the patient's teeth. On-track movement has been described further herein, e.g., at Table 1. In some embodiments, the orthodontic appliances disclosed herein can be used to achieve on-track movement of at least one of the patient's teeth to an intermediate tooth arrangement. In some embodiments, the orthodontic appliances disclosed herein can be used to achieve on-track movement of at least one of the patient's teeth to a final tooth arrangement.

In some embodiments, prior to moving on-track, with the orthodontic appliance, at least one of the patient's teeth toward the intermediate arrangement or the final tooth arrangement, the orthodontic appliance comprises a first flexural stress; and after achieving on-track the movement of the at least one of the patient's teeth to the intermediate arrangement or the final tooth arrangement, the orthodontic appliance comprises a second flexural stress. In some embodiments, the second flexural stress is from 80 MPa to 0.5 MPa, from 70 MPa to 0.5 MPa, from 60 MPa to 1 MPa, from 50 MPa to 1 MPa, from 40 MPa to 1 MPa, from 30 MPa to 2 MPa, from 25 MPa to 2 MPa, from 20 MPa to 2 MPa, from 15 MPa to 2 MPa, or from 15 MPa to 0.01 MPa. In some embodiments, flexural stress is assessed according to ASTM E328. In some embodiments, the time period between an initial placement of the orthodontic appliance to the patient's teeth and achieving on-track the movement is 3 days, 4 days, 5 days, 6 days, 7 days, 8 days, 9 days, 10 days, 11 days, 12 days, 13 days, two weeks, or less than two weeks.

In some embodiments, prior to moving, with the orthodontic appliance, at least one of the patient's teeth toward an intermediate arrangement or a final tooth arrangement, the orthodontic appliance has characteristics which are retained following the use of the orthodontic appliance.

As provided herein, the methods disclosed can use the orthodontic appliances further disclosed herein. Said orthodontic appliances can be directly fabricated using, e.g., the resins disclosed herein. In certain embodiments, the direct fabrication comprises cross-linking the resin.

The appliances formed from the resins disclosed herein provide improved durability, strength, and flexibility, which in turn improve the rate of on-track progression in treatment plans. In some embodiments, greater than 60%, greater than 70%, greater than 80%, greater than 90%, or greater than 95% of patients treated with the orthodontic appliances disclosed herein (e.g., an aligner) are classified as on-track in a given treatment stage. In certain embodiments, greater than 60%, greater than 70%, greater than 80%, greater than 90%, or greater than 95% of patients treated with the orthodontic appliances disclosed herein (e.g., an aligner) have greater than 50%, greater than 55%, greater than 60%, greater than 65%, greater than 70%, greater than 75%, greater than 80%, greater than 85%, greater than 90%, or greater than 95% of their tooth movements classified as on-track.

As disclosed further herein, the cured polymeric material contains favorable characteristics that, at least in part, stem from the presence of the first and second continuous phases. These cured polymeric materials can have increased resilience to damage and can be tough when compared to similar polymeric materials. The cured polymeric materials can be used for devices within the field of orthodontics, as well as outside the field of orthodontics.

EXAMPLES

The specific compositions, synthesis, formulations, and descriptions of any of the materials, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Example 1

Comparative Properties of Formulations

This example describes the formation of a material using a formulation including methacrylate as a hard phase and compares it to the formation of a material using a formulation including acrylate as a hard phase. This example also compares the properties of each formed material.

A methacrylate-hard-phased resin (Resin 1) was prepared by combining 15 wt % TGM1-RD1 (TGM1 with RD1), 35 wt % tetramethylxylene diisocyanate methacrylate ((TMX)-methacrylate), and 50 wt % 2-isopropyl-5-methylcyclohexyl 2-(methacryloxy)benzoate (menthyl salicylate methacrylate or MSMA). The TMX-methacrylate served as the soft continuous phase and the MSMA served as the hard (methacrylate) phase while the TGM1-RD1 served as a cross-linker. To the resulting resin was added 1 wt % TPO-L (photoinitiator).

An acrylate-hard-phased resin (Resin 2) was prepared by combining 15 wt % TGM1-RD1 (TGM1 with RD1), 35 wt % (TMX)-methacrylate, and 50 wt % 2-isopropyl-5-methylcyclohexyl 2-(acryloxy)benzoate (MSA). The TMX-methacrylate served as the soft continuous phase and the MSA served as the hard (acrylate) phase while the TGM1-RD1 served as a crosslinker. To the resulting resin was added 1 wt % TPO-L (photoinitiator).

Example 2

Treatment Using an Orthodontic Appliance

This example describes the use of a directly 3D printed orthodontic appliance to move a patient's teeth according to a treatment plan. This example also describes the characteristics that the orthodontic appliance can have following its use, in contrast to its characteristics prior to use.

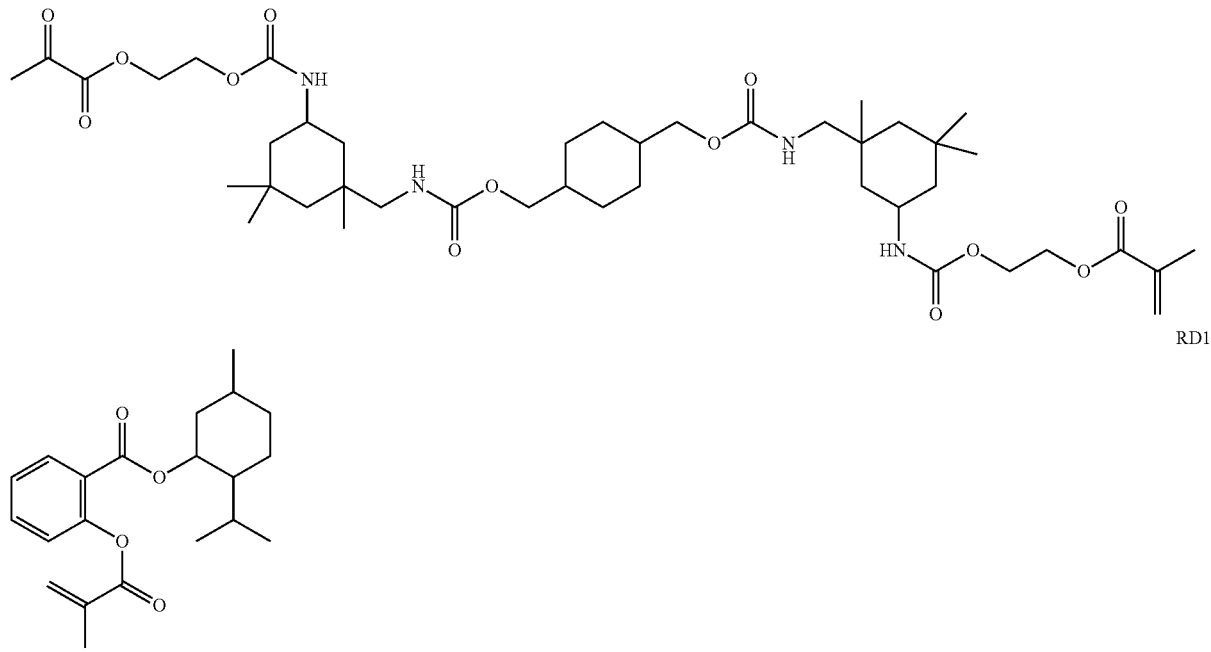

Each of the resins was cured. Resin 1 was cured, thereby forming Material 1 and Resin 2 was cured, thereby forming Material 2. The material properties from each of Material 1 and Material 2 were tested, as displayed below in Table 2:

TABLE 2

| Material Property | Material 1 | Material 2 |
|---|---|---|
| c (24 hours, 37° C.) | 0.47 | 0.60 |
| Stress Relaxation (24 hours) | 4.78% | 14.09% |
| Yield Strength | 15 MPa | 26 MPa |
| Maximum Tensile Strength | 20 MPa | 35 MPa |
| Maximum Elongation | 105.0% | 119.6% |
| Tensile Modulus | 574.0 MPa | 826.0 MPa |

Wherein "c" corresponds to the water uptake within 24 h at 37° C. in % for the material samples above and with dimensions of 50 mm×21 mm×0.78 mm. The data showed that Material 2 (comprising the acrylate hard phase) showed overall superior material properties over Material 1 (comprising the methacrylate hard phase). This demonstrates that relatively soft materials (e.g., acrylates) can provide favorable properties, including increased overall hardness due to the formation of hard and soft phases in the polymer network, and their interconnection with one another. Hence, the acrylate material had increased hardness while retaining increased elongation properties.

A patient in need of, or desirous of, a therapeutic treatment to rearrange at least one tooth has their teeth arrangement assessed. An orthodontic treatment plan is generated for the patient. The orthodontic treatment plan comprises a plurality of intermediate tooth arrangements for moving teeth along a treatment path, from the initial arrangement (e.g., that which was initially assessed) toward a final arrangement. The treatment plan includes the use of an orthodontic appliance, fabricated using the resins and methods disclosed further herein, to provide orthodontic appliances having a plurality of polymer phases. In some embodiments, a plurality of orthodontic appliances are used, each of which can be fabricated using the resins and methods disclosed further herein.

The orthodontic appliances are provided, and iteratively applied to the patient's teeth to move the teeth through each of the intermediate tooth arrangements toward the final arrangement. The patient's tooth movement is tracked. A comparison is made between the patient's actual teeth arrangement and the planned intermediate arrangement. Where the patient's teeth are determined to be tracking according to the treatment plan, but have not yet reached the final arrangement, the next set of appliances can be administered to the patient. The threshold difference values of a planned position of teeth to actual positions selected as indicating that a patient's teeth have progressed on-track are provided above in Table 1. If a patient's teeth have progressed at or within the threshold values, the progress is considered to be on-track. Favorably, the use of the appliances disclosed herein increases the probability of on-track tooth movement.

The assessment and determination of whether treatment is on-track can be conducted, for example, 1 week (7 days) following the initial application of an orthodontic appliance. Following this period of application, additional parameters relating to assessing the durability of the orthodontic appliance can also be conducted. For example, relative repositioning force (compared to that which was initially provided by the appliance), intactness of polymer chains (e.g., the percent of polymer chains that are not broken), relative flexural modulus, and relative elongation at break can be determined.

What is claimed is:

1. A curable resin, comprising:
   a first continuous phase comprising a first polymerizable component having a first polymerization rate; and
   a second continuous phase comprising a second polymerizable component having a second polymerization rate, wherein the first polymerization rate is higher than the second polymerization rate,
   wherein the first polymerization rate and the second polymerization rate are determined at conditions sufficient for 3D printing and are selected such that greater than 90% of the first polymerizable component is polymerized prior to 15% or less of the second polymerizable component being polymerized, and
   wherein the first continuous phase, upon curing, comprises a first polymer region having a first hardness and the second continuous phase, upon curing, comprises a second polymer region having a second hardness, wherein the first hardness is less than the second hardness as determined after 24 hours in an aqueous environment at 37° C.

2. The curable resin of claim 1, wherein
   the first continuous phase further comprises
      the second polymerizable component, wherein the first polymerizable component is present at a higher concentration than the second polymerizable component; and
   wherein the second continuous phase comprises
      the first polymerizable component, wherein the first polymerizable component is present at a lower concentration than the second polymerizable component.

3. The curable resin of claim 1, further comprising
   a third continuous phase comprising a third polymerizable component having a third polymerization rate, wherein the third polymerization rate is determined at the conditions sufficient for 3D printing.

4. The curable resin of claim 1, wherein
   the first polymerizable component is free-radically polymerizable; and the second polymerizable component is ionically polymerizable.

5. The curable resin of claim 1, wherein:
   the first hardness is from 60 Shore A to 85 Shore D; and
   the second hardness from 60 Shore A to 85 Shore D.

6. The curable resin of claim 1, wherein:
   (i) the first polymerizable component comprises a methacrylate moiety and the second polymerizable component comprises an acrylate moiety;
   (ii) the first polymerizable component comprises a polymer and the second polymerizable component comprises a polymerizable monomer; or
   (iii) the first polymerizable component comprises a polymerizable monomer and the second polymerizable component comprises a polymer.

7. The curable resin of claim 1, wherein the first polymerization rate has a rate constant of at least $3.5 \times 10^3$ s$^{-1}$ and not more than $5 \times 10^3$ s$^{-1}$, and the second polymerization rate has a rate constant of at least $1.8 \times 10^3$ s$^{-1}$ and not more than $2.5 \times 10^3$ s$^{-1}$.

8. The curable resin of claim 1, wherein the first polymerizable component comprises an acrylate or a methacrylate and the second polymerizable component:
   (i) comprises a vinyl ester, or
   (ii) comprises an epoxide.

9. The curable resin of claim 1, further comprising a third phase, a fourth phase, or more than four phases.

10. The curable resin of claim 9, wherein the third phase comprises a filler, a polymer, an unreactive component, or a combination thereof.

11. The curable resin of claim 10, wherein the polymer is a thermoplastic polymer comprising polyolefin, polyester, polyacrylate, polymethacrylate, polystyrene, polypropylene, polyethylene, polyethylene terephthalate, poly lactic acid, polyurethane, epoxide polymer, polyether, poly(vinyl chloride), polysiloxane, polycarbonate, polyamide, polyacrylonitrile, polybutadiene, poly(cycloolefin), a copolymer thereof, or any combination thereof.

12. The curable resin of claim 6, wherein:
   the polymer comprises one or more reactive functional groups.

13. The curable resin of claim 1, further comprising a filler, wherein:
   (i) the filler is comprised within a discontinuous phase of the curable resin;
   (ii) the filler is comprised within a continuous phase of the curable resin;
   (iii) the filler is functionalized;
   (iv) the filler comprises a fiber;
   (v) the filler comprises calcium carbonate, kaolin, metakaolinite, a kaolinite derivative, magnesium hydroxide, calcium silicate, glass, a nanofiller, nanoplates, nanofibers, nanoparticles, a silica filler, a mica, silica gel, fumed silica, precipitated silica, carbon black, dolomite, barium sulfate, ATH Al(OH)3, MDH Mg(OH)2, diatomaceous earth, magnetite, halloysite, zinc oxide, titanium dioxide, cellulose, lignin, a carbon filler, chopped carbon fiber, carbon fiber, a derivative thereof, or a combination thereof; or
   (vi) any combination of (i)-(v).

14. The curable resin of claim 1, wherein the curable resin comprises a plurality of first continuous phases and a plurality of second continuous phases.

15. A method of producing a composite polymer composition, the method comprising:
   providing a resin of claim 1; and
   initiating a polymerization reaction by curing the resin.

16. A composite material comprising:
   a first continuous phase comprising a first polymer region, comprising, a first polymerizable component in a polymerized form, and having a first hardness from 60 Shore A to 85 Shore D; and
   a second continuous phase comprising a second polymer region, comprising a second polymerizable component in a polymerized form, and having a second hardness from 60 Shore A to 85 Shore D,
   wherein the first polymerizable component polymerized faster than the second polymerizable component, and wherein the first hardness is less than the second hardness as determined after 24 hours in an aqueous environment at 37° C.

17. The curable resin of claim 1, further comprising a thermal initiator, wherein the thermal initiator comprises an azo compound, an inorganic peroxide, an organic peroxide, a thermal acid generator, a thermal base generator, tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis(tert-butylperoxy-2,5-dimethylhexane, 2,5-bis(tert-butylperoxy)-2,5-dimethyl-3-hexyne, bis(1-(tert-butylperoxy)-3,3,5-trimethylcyclohexane, tert-butyl hydroxyperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, potassium persulfate, a derivative thereof, or any combination thereof.

18. The curable resin of claim 1, further comprising a polymerization catalyst, wherein the polymerization catalyst comprises a tin catalyst, a platinum catalyst, a rhodium catalyst, a titanium catalyst, a silicon catalyst, a palladium catalyst, a metal triflate catalyst, a boron catalyst, a bismuth catalyst, or any combination thereof.

19. The curable resin of claim 1, further comprising a polymerization inhibitor, wherein the polymerization inhibitor comprises a photopolymerization inhibitor, a phenolic compound, a stable radical, a radical scavenger, an antioxidant, a hindered amine light stabilizer (HAL), a hindered phenol, a deactivated radical, 4-tert-butylpyrocatechol, tert-butylhydroquinone, 1, 4-benzoquinone, 6-tert-butyl-2,4-xylenol, 2-tert-butyl-1,4-benzoquinone, 2,6-di-tert-butyl-p-cresol, 2,6-di-tert-butylphenol, 1,1-diphenyl-2-picrylhydrazyl free radical, hydroquinone, 4-methoxyphenol, phenothiazine, any derivative thereof, or any combination thereof.

20. The curable resin of claim 1, further comprising a light blocker, wherein the light blocker comprises a UV light absorber, a pigment, a color concentrate, or an IR light absorber a benzotriazole, a hydroxyphenyltriazine, an oxanilide, a benzophenone, or any combination thereof.

21. The curable resin of claim 1, further comprising a surface energy modifier, wherein the surface energy modifier comprises a defoaming agent, a deairation agent, a hydrophobization agent, a leveling agent, a wetting agent, an emulsion stabilizer, an emulsion destabilizer, an agent to adjust the flow properties of the curable resin, an aloxylated surfactant, a silicone surfactant, a sulfosuccinate, a fluorinated polyacrylate, a fluoropolymer, a silicone, a star-shaped polymer, an organomodified silicone, or any combination thereof.

22. The curable resin of claim 1, further comprising a plasticizer, wherein the plasticizer comprises a dicarboxylic ester plasticizer, a tricarboxylic ester plasticizer, a trimellitate, an adipate, a sebacate, a maleate, or a bio-based plasticizer.

23. The curable resin of claim 1, further comprising a solvent, wherein the solvent comprises a nonpolar solvent, a polar aprotic solvent, a polar protic solvent, pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, DMSO, propylene carbonate, formic acid, n-butanol, isopropyl alcohol, n-propanol, t-butanol, ethanol, methanol, acetic acid, water, a derivative thereof, or any combination thereof.

24. The curable resin of claim 1, wherein the first polymerization rate and the second polymerization rate are selected such that greater than 90% of the first polymerizable component is polymerized prior to 10% or less of the second polymerizable component being polymerized.

25. The curable resin of claim 1, wherein the first polymerization rate and the second polymerization rate are selected such that greater than 90% of the first polymerizable component is polymerized prior to 5% or less of the second polymerizable component being polymerized.

* * * * *